US010576063B2

(12) United States Patent
Seward

(10) Patent No.: US 10,576,063 B2
(45) Date of Patent: Mar. 3, 2020

(54) COMBINATION THERAPY FOR TREATMENT OF RESTENOSIS

(71) Applicant: Mercator MedSystems, Inc., Emeryville, CA (US)

(72) Inventor: Kirk Patrick Seward, San Francisco, CA (US)

(73) Assignee: Mercator MedSystems, Inc., Emeryville, CA (US)

( * ) Notice: Subject to any disclaimer, the term of this patent is extended or adjusted under 35 U.S.C. 154(b) by 0 days.

(21) Appl. No.: 15/990,167

(22) Filed: May 25, 2018

(65) Prior Publication Data

US 2018/0353488 A1 Dec. 13, 2018

Related U.S. Application Data

(60) Provisional application No. 62/624,528, filed on Jan. 31, 2018, provisional application No. 62/511,797, filed on May 26, 2017.

(51) Int. Cl.
*A61K 31/436* (2006.01)
*A61P 9/14* (2006.01)
*A61P 9/04* (2006.01)
*A61K 9/00* (2006.01)
*A61P 9/10* (2006.01)
*A61K 31/573* (2006.01)

(52) U.S. Cl.
CPC .......... *A61K 31/436* (2013.01); *A61K 9/0019* (2013.01); *A61P 9/04* (2018.01); *A61P 9/10* (2018.01); *A61P 9/14* (2018.01); *A61K 31/573* (2013.01); *A61K 2300/00* (2013.01)

(58) Field of Classification Search
CPC .................................................. A61K 31/436
USPC ......................................................... 514/171
See application file for complete search history.

(56) References Cited

U.S. PATENT DOCUMENTS

| | | | |
|---|---|---|---|
| 5,112,305 A | 5/1992 | Barath et al. | |
| 5,196,024 A | 3/1993 | Barath | |
| 5,270,047 A | 12/1993 | Kauffman et al. | |
| 5,354,279 A | 10/1994 | Hoefling | |
| 5,362,718 A * | 11/1994 | Skotnicki | C07D 498/18 514/291 |
| 5,527,532 A | 6/1996 | Edelman et al. | |
| 5,538,504 A | 7/1996 | Linden et al. | |
| 5,645,564 A | 7/1997 | Northrup et al. | |
| 5,681,281 A | 10/1997 | Vigil et al. | |
| 5,693,029 A | 12/1997 | Leonhardt | |
| 5,722,989 A | 3/1998 | Fitch et al. | |
| 5,866,561 A | 2/1999 | Ungs | |
| 5,900,246 A | 5/1999 | Lambert | |
| 6,009,877 A | 1/2000 | Edwards | |
| 6,059,815 A | 5/2000 | Lee et al. | |
| 6,102,933 A | 8/2000 | Lee et al. | |
| 6,210,392 B1 | 4/2001 | Vigil et al. | |
| 6,283,947 B1 | 9/2001 | Mirzaee | |
| 6,302,870 B1 | 10/2001 | Jacobsen et al. | |
| 6,334,856 B1 | 1/2002 | Allen et al. | |
| 6,494,862 B1 | 12/2002 | Ray et al. | |
| 6,547,303 B1 | 4/2003 | Anderson | |
| 6,547,803 B2 | 4/2003 | Seward et al. | |
| 6,625,486 B2 | 9/2003 | Lundkvist et al. | |
| 6,860,867 B2 | 3/2005 | Seward et al. | |
| 7,008,411 B1 | 3/2006 | Mandrusov et al. | |
| 7,094,765 B1 | 8/2006 | Iversen et al. | |
| 7,247,149 B2 | 7/2007 | Beyerlein | |
| 7,744,584 B2 | 6/2010 | Seward et al. | |
| 8,708,995 B2 | 4/2014 | Seward et al. | |
| 9,884,013 B2 | 2/2018 | Seward et al. | |
| 2002/0001581 A1 | 1/2002 | Lynch et al. | |
| 2002/0052404 A1 | 5/2002 | Hunter et al. | |
| 2002/0156000 A1 | 10/2002 | May et al. | |
| 2002/0188310 A1 | 12/2002 | Seward et al. | |
| 2003/0040712 A1 | 2/2003 | Ray et al. | |
| 2003/0078562 A1 | 4/2003 | Makower et al. | |
| 2003/0120297 A1 | 6/2003 | Beyerlein | |
| 2003/0170287 A1 | 9/2003 | Prescott | |
| 2003/0171734 A1 | 9/2003 | Seward et al. | |
| 2004/0067197 A1 | 4/2004 | Leclerc et al. | |
| 2004/0138643 A1 | 7/2004 | Seward et al. | |
| 2004/0162542 A1 | 8/2004 | Wilber et al. | |

(Continued)

FOREIGN PATENT DOCUMENTS

| | | |
|---|---|---|
| WO | WO-0121157 A2 | 3/2001 |
| WO | WO-0121157 A3 | 12/2001 |

(Continued)

OTHER PUBLICATIONS

Zhang et al., "Synergistic activity of rapamycin and dexamethasone in vitro and in vivo in acute lymphoblastic leukemia via cell-cycle arrest and apoptosis", Leukemia Research, vol. 36, No. 3, pp. 342-349 (2012).*
International Application No. PCT/US17/52790 International Search Report and Written Opinion dated Dec. 8, 2017.
Siablis, D. et al. Sirolimus-Eluting Versus Bare Stents After Suboptimal Ingrapopliteal Angioplastry for Critical Limb Ischemia: Enduring 1-Year Angiographic and Clinical Benefit, J. Endovasc. Ther. 14:241-250 (2007).
U.S. Appl. No. 15/890,857 Non-Final Office Action dated May 30, 2018.

(Continued)

*Primary Examiner* — Kevin E Weddington
(74) *Attorney, Agent, or Firm* — Wilson Sonsini Goodrich & Rosati

(57) ABSTRACT

Described herein are methods for distributing a combination of a cell division inhibitor (e.g., temsirolimus or paclitaxel) and dexamethasone to a tissue surrounding a blood vessel for treating vascular diseases. Also disclosed are injectable compositions of a cell division inhibitor (e.g., temsirolimus or paclitaxel) and dexamethasone for delivery into the tissue surrounding a blood vessel for treating vascular diseases.

26 Claims, 23 Drawing Sheets

(56) References Cited

U.S. PATENT DOCUMENTS

| | | | |
|---|---|---|---|
| 2004/0167152 | A1 | 8/2004 | Rubino et al. |
| 2004/0260240 | A1 | 12/2004 | Beyerlein |
| 2004/0260268 | A1 | 12/2004 | Falotico et al. |
| 2005/0090714 | A1 | 4/2005 | Greff |
| 2005/0158361 | A1 | 7/2005 | Dhondt et al. |
| 2005/0163711 | A1 | 7/2005 | Nycz et al. |
| 2005/0182071 | A1 | 8/2005 | Seward et al. |
| 2005/0232965 | A1 | 10/2005 | Falotico |
| 2006/0069349 | A1 | 3/2006 | Ganz et al. |
| 2006/0115903 | A1 | 6/2006 | Ridker et al. |
| 2006/0122684 | A1 | 6/2006 | Lye et al. |
| 2006/0189941 | A1* | 8/2006 | Seward ............... A61M 25/10 604/164.03 |
| 2007/0078620 | A1 | 4/2007 | Seward et al. |
| 2007/0100318 | A1 | 5/2007 | Seward et al. |
| 2007/0100319 | A1 | 5/2007 | Seward et al. |
| 2007/0100320 | A1 | 5/2007 | Seward et al. |
| 2007/0106248 | A1 | 5/2007 | Seward et al. |
| 2007/0106249 | A1 | 5/2007 | Seward et al. |
| 2007/0106250 | A1 | 5/2007 | Seward et al. |
| 2007/0106251 | A1 | 5/2007 | Seward et al. |
| 2007/0106252 | A1 | 5/2007 | Seward et al. |
| 2007/0106253 | A1 | 5/2007 | Seward et al. |
| 2007/0106254 | A1 | 5/2007 | Seward et al. |
| 2007/0106255 | A1 | 5/2007 | Seward et al. |
| 2007/0106256 | A1 | 5/2007 | Seward et al. |
| 2007/0106257 | A1 | 5/2007 | Seward et al. |
| 2007/0129789 | A1 | 6/2007 | Cottone, Jr. et al. |
| 2007/0269385 | A1 | 11/2007 | Yun et al. |
| 2008/0038316 | A1 | 2/2008 | Wong et al. |
| 2009/0204104 | A1 | 8/2009 | Tremble et al. |
| 2010/0082095 | A1 | 4/2010 | Pacetti et al. |
| 2010/0305546 | A1 | 12/2010 | Seward et al. |
| 2013/0029950 | A1 | 1/2013 | Bischoff et al. |
| 2013/0035665 | A1 | 2/2013 | Chu et al. |
| 2013/0224255 | A1 | 8/2013 | Hossainy et al. |
| 2014/0296279 | A1 | 10/2014 | Seward et al. |
| 2014/0303569 | A1 | 10/2014 | Seward et al. |
| 2015/0141959 | A1 | 5/2015 | Kirk |
| 2018/0169075 | A1 | 6/2018 | Seward et al. |

FOREIGN PATENT DOCUMENTS

| | | |
|---|---|---|
| WO | WO-2010104584 A2 | 9/2010 |
| WO | WO-2014118696 A2 | 8/2014 |
| WO | WO-2017078405 A1 | 5/2017 |
| WO | WO-2018218182 A1 | 11/2018 |

OTHER PUBLICATIONS

Altman et al. Exploring heart lymphatics in local drug delivery, Lymph. Res. Biol., (2003) 1:47-54.

Ayers et al. Amiodarone instilled into the canine pericardial sac migrates transmurally to produce electrophysiologic effects and suppress atrial fibrillation.

Barath et al. "Infiltrator Angioplasty Balloon Catheter: a device for combined angioplasty and intramural site-specific treatment," Cathet Cardiovasc Diagn. Jul. 1997;41(3):333-341.

Chandrasekar et al. "Coronary Artery Endothelial. Protection After Local Delivery of 17Il-Estradiol During Balloon Angioplasty in a Porcine Model : A Potential New Pharmacologic Approach to Improve Endothelial Function," J. Am. Col. Cardiol. (2001), 38(5):1570-1576.

Chandrasekar et al. "Local Delivery of 17-Beta-Estradiol Decreases Neointimal Hyperplasia After Coronary Angioplasty in a Porcine Model," J. Am. Col. Cardiol. (2000), 36(6):1972-1978.

ClinicalTrials.gov. Identifier: NCT01507558. Dexamethasone Infusion to the Adventitia to Enhance Clinical Efficacy After Femoropopliteal Revascularization (DANCE). https://clinicaltrials.gov/ct2/show/NCT01507558?term=nct01507558&rank=1. Last updated Aug. 15, 2014. Accessed on Mar. 4, 2015. 4 pages.

Co-pending U.S. Appl. No. 16/058,690, filed Aug. 8, 2018.

Creel, "Arterial Paclitaxel Distribution and Deposition," Circulation Research. Apr. 2000;86:879-884.

Dai-Do et al., "17 beta-estradiol inhibits proliferation and migration of human vascular smooth muscle cells: similar effects in cells from postmenopausal females and in males," Cardiovasc Res. Nov. 1996;32(5):980-985.

Daschner et al., Penetration of gentamicin into heart valves, subcutaneous and muscular tissue of patients undergoing open heart surgery, J. Cardiovasc. Surg., (1986) 581-584.

European Application No. 16743927.2-1109 Extended European Search Report dated Aug. 17, 2018.

Gaspardone, et al. C-Reactive protein, clinical outcome, and restenosis rates after implantation of different drug-eluting stents. Am J Cardiol. May 1, 2006;97(9):1311-6. Epub Mar. 20, 2006.

Gasper, W. et al. Adventitial Nab-Rapamycin Injection Reduces Porcine Femoral Artery Luminal Stenosis Induced by Balloon Angioplasty via Inhibition of Medial Proliferation and Adventitial Inflammation. Circulation: Cardiovascular Interventions. 6(6):701-709 (Dec. 1, 2013).

Han, et al. The favorable clinical and angiographic outcomes of a high-dose dexamethasone-eluting stent: randomized controlled prospective study. Am Heart J. Nov. 2006;152(5):887.e1-7.

Ikeno et al., "Novel percutaneous adventitial drug delivery system for regional vascular treatment," Catheter Cardiovasc. interv., (2004) 63: 220-230.

International Application No. PCT/US18/34713 International Search Report and Written Opinion dated Oct. 19, 2018.

International Application No. PCT/US18/34713 Search Report and Written Opinion dated Oct. 19, 2018.

International search report and written opinion dated Mar. 17, 2016 for PCT/US2016/014819.

International search report dated Apr. 21, 2004 for PCT/US2003/002130.

Konig, et al. Randomized comparison of dexamethasone-eluting stents with bare metal stent implantation in patients with acute coronary syndrome: serial angiographic and sonographic analysis. Am Heart J. Jun. 2007;153(6):979.e1-8.

Laham et al., Intracoronary and intravenous administration of basic fibroblast growth factor: myocardial and tissue distribution, Drug Met. Disp., (1999) 27:821-826.

Laham et al., Intrapericardial administration of basic fibroblast growth factor: myocardial and tissue distribution and comparison with intracoronary and intravenous administration, Cath Cardio. Interv., (2003) 58:375-381.

Nikol et al., "Needle Injection Catheter Delivery of the Gene for an Antibacterial Agent Inhibits Neointimal Formation," Gene Therapy, May 1999, vol. 6, No. 5, pp. 737-748.

Notice of allowance dated Feb. 23, 2010 for U.S. Appl. No. 10/691,119.

Notice of allowance dated Apr. 23, 2015 for U.S. Appl. No. 14/203,942.

Notice of allowance dated Dec. 26, 2013 for U.S. Appl. No. 12/790,541.

Office action dated Jan. 9, 2015 for U.S. Appl. No. 14/203,942.
Office action dated Jan. 30, 2007 for U.S. Appl. No. 10/350,314.
Office action dated Feb. 2, 2011 for U.S. Appl. No. 12/790,541.
Office action dated Feb. 26, 2009 for U.S. Appl. No. 10/691,119.
Office action dated Apr. 16, 2008 for U.S. Appl. No. 10/691,119.
Office action dated May 15, 2008 for U.S. Appl. No. 10/350,314.
Office action dated May 16, 2007 for U.S. Appl. No. 10/350,314.
Office action dated Jun. 25, 2007 for U.S. Appl. No. 11/601,290.
Office action dated Jun. 25, 2007 for U.S. Appl. No. 11/607,177.
Office action dated Jun. 27, 2007 for U.S. Appl. No. 11/607,168.
Office action dated Jun. 27, 2007 for U.S. Appl. No. 11/607,170.
Office action dated Jun. 27, 2007 for U.S. Appl. No. 11/607,172.
Office action dated Jun. 27, 2007 for U.S. Appl. No. 11/607,175.
Office action dated Jun. 27, 2007 for U.S. Appl. No. 11/607,176.
Office action dated Jun. 27, 2007 for U.S. Appl. No. 11/607,356.
Office action dated Jul. 2, 2007 for U.S. Appl. No. 11/607,355.
Office action dated Jul. 14, 2006 for U.S. Appl. No. 10/350,314.
Office action dated Jul. 16, 2007 for U.S. Appl. No. 11/607,166.
Office action dated Jul. 16, 2007 for U.S. Appl. No. 11/607,167.
Office action dated Jul. 16, 2007 for U.S. Appl. No. 11/607,178.

(56) References Cited

OTHER PUBLICATIONS

Office action dated Jul. 16, 2007 for U.S. Appl. No. 11/607,658.
Office action dated Jul. 17, 2007 for U.S. Appl. No. 11/607,169.
Office action dated Aug. 20, 2008 for U.S. Appl. No. 10/350,314.
Office action dated Aug. 20, 2008 for U.S. Appl. No. 10/691,119.
Office action dated Aug. 24, 2007 for U.S. Appl. No. 10/350,314.
Office action dated Sep. 15, 2009 for U.S. Appl. No. 10/691,119.
Office action dated Oct. 11, 2011 for U.S. Appl. No. 12/790,541.
Office action dated Dec. 12, 2006 for U.S. Appl. No. 10/691,119.
Owens, Christopher D. et al. Safety and feasibility of adjunctive dexamethasone infusion into the adventitia of the femoropopliteal artery following endovascular revascularization. Journal of Vascular Surgery 59(4):1016-1024 (Apr. 2014).
Owens, Christopher D., MD. Pilot Results from DANCE: Dexamethasone to the Adventitia to eNhance Clinical Efficacy in PAD. pp. 1-19 (2012).
Pharmacia & Upjohn Company, "Depo-Estradiol," Product/Prescription Information [pamphlet], (Aug. 2000), 6 pages total.
Schillinger, et al. Balloon angioplasty and stent implantation induce a vascular inflammatory reaction. J Endovasc Ther. Feb. 2002;9(1):59-66.
Solmon et al. "Amiodarone versus a [3-blocker to prevent atrial fibrillation after cardiovascular surgery," AHJ, Nov. 2001; 142(5):811-815.
U.S. Appl. No. 14/605,865 Final Office Action dated Aug. 31, 2017.
U.S. Appl. No. 14/605,865 Non-Final Office Action dated Dec. 28, 2017.
U.S. Appl. No. 14/605,865 Non-Final Office Action dated Sep. 17, 2018.
U.S. Appl. No. 14/605,865 Notice of Allowance dated Jul. 6, 2018.
U.S. Appl. No. 14/605,865 Office Action dated Sep. 22, 2016.
U.S. Appl. No. 15/890,857 Final Office Action dated Nov. 14, 2018.
U.S. Appl. No. 09/961,079, filed Sep. 20, 2001.
U.S. Appl. No. 60/356,670, filed Feb. 13, 2002.
U.S. Appl. No. 15/890,857 Office Action dated Jul. 1, 2019.
U.S. Appl. No. 16/058,690 Office Action dated Aug. 7, 2019.

\* cited by examiner

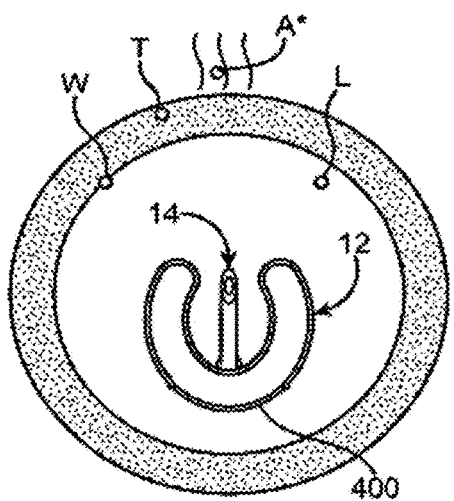
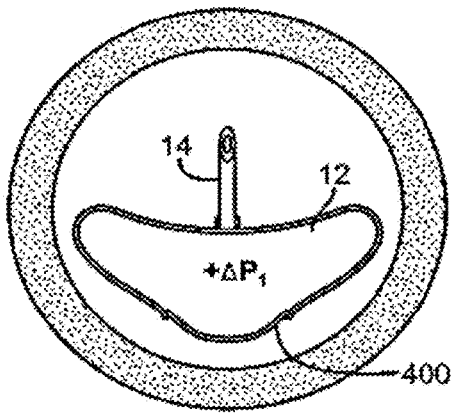
FIG. 10A  FIG. 10B
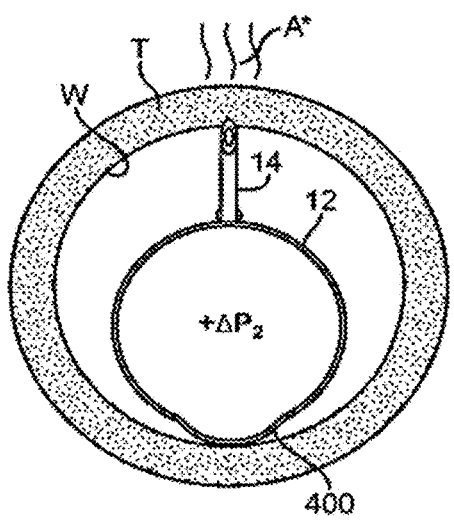
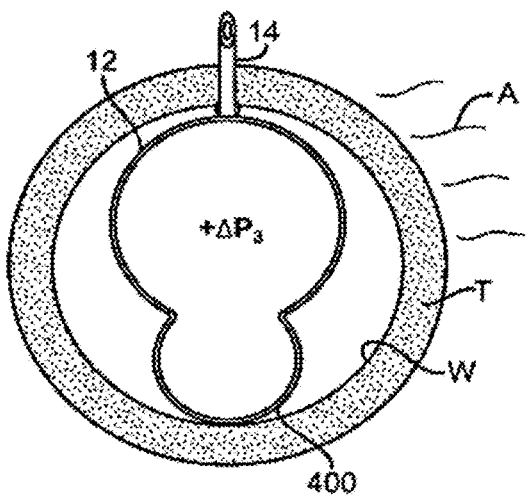
FIG. 10C  FIG. 10D

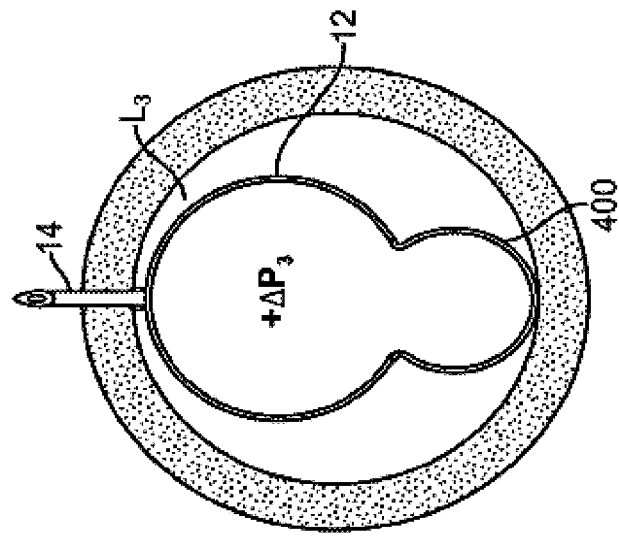
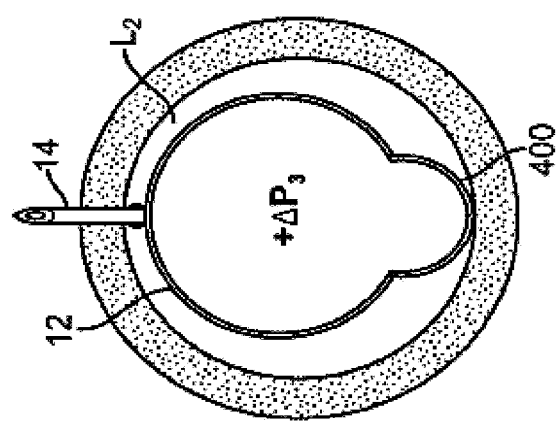
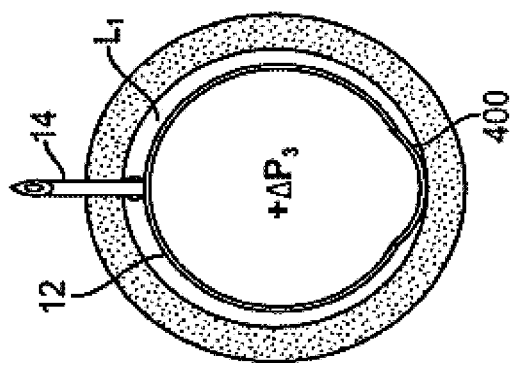
FIG. 11C
FIG. 11B
FIG. 11A

COMBINATION THERAPY FOR TREATMENT OF RESTENOSIS

CROSS-REFERENCE

This application claims the benefit of U.S. provisional patent application No. 62/511,797, filed on May 26, 2017, and U.S. provisional patent application No. 62/624,528, filed on Jan. 31, 2018, which are all hereby incorporated by reference in their entirety.

BACKGROUND

The present disclosure relates generally to medical methods and devices. More particularly, the present disclosure relates to medical methods and kits for distributing temsirolimus in the tissue surrounding a blood vessel. Further, the present disclosure relates to medical methods and kits for distributing temsirolimus in combination with a glucocorticoid in the tissue surrounding a blood vessel.

Blockages can form in blood vessels under various disease conditions. In atherosclerosis, the narrowing of arteries in the body, particularly in the heart, legs, carotid and renal anatomy, can lead to tissue ischemia from lack of blood flow. Mechanical revascularization methods, such as balloon angioplasty, atherectomy, stenting, or surgical endarterectomy, are used to open the blood vessel and to improve blood flow to downstream tissues. Unfortunately, mechanical revascularization can lead to an injury cascade that causes the blood vessel to stiffen and vessel walls to thicken with a scar-like tissue, which can reduce the blood flow and necessitate another revascularization procedure. There is a great desire to reduce the vessel stiffening and thickening following mechanical revascularization to maintain or improve the patency of the blood vessel.

SUMMARY OF THE INVENTION

The present disclosure provides methods, devices, and compositions for distributing a combination of a cell division inhibitor and a glucocorticoid into a tissue surrounding a blood vessel for treating vascular diseases.

Provided herein are pharmaceutical compositions comprising temsirolimus and a glucocorticoid, or their pharmaceutically acceptable salts thereof. Further provided herein are pharmaceutical compositions wherein the glucocorticoid is dexamethasone or a pharmaceutically acceptable salt thereof. Further provided herein are pharmaceutical compositions wherein the ratio (by weight) of temsirolimus to the glucocorticoid, or vice versa, is between 10:1 to 1:1. Further provided herein are pharmaceutical compositions wherein the composition is in an injectable dosage form. Further provided herein are pharmaceutical compositions wherein the composition further comprises at least one pharmaceutically acceptable excipient. Further provided herein are pharmaceutical compositions wherein the concentration of dexamethasone is 1.0-8.0 mg/mL. Further provided herein are pharmaceutical compositions wherein the concentration of dexamethasone is about 3.2 mg/mL. Further provided herein are pharmaceutical compositions wherein the concentration of dexamethasone is less than 4.0 mg/mL. Further provided herein are pharmaceutical compositions wherein the concentration of temsirolimus is 0.01-2.0 mg/mL. Further provided herein are pharmaceutical compositions wherein the concentration of temsirolimus is 0.05-0.5 mg/mL. Further provided herein are pharmaceutical compositions wherein the concentration of temsirolimus is about 0.1 mg/mL. Further provided herein are pharmaceutical compositions wherein the concentration of temsirolimus is about 0.4 mg/mL. Further provided herein are pharmaceutical compositions for use in treating restenosis. Further provided herein are pharmaceutical compositions for use in treating restenosis below the knee. Further provided herein are pharmaceutical compositions for use in treating restenosis above the knee. Further provided herein are pharmaceutical compositions for use in treating restenosis in a below-knee popliteal vessel or tibial vessel.

Provided herein are injectable compositions comprising temsirolimus or a pharmaceutically acceptable salt thereof, dexamethasone or a pharmaceutically acceptable salt thereof, and a pharmaceutically acceptable excipient. Further provided herein are injectable compositions wherein the composition is suitable for adventitial delivery. Further provided herein are injectable compositions wherein the composition is suitable for adventitial delivery to a coronary vessel. Further provided herein are injectable compositions wherein the composition is suitable for adventitial delivery to a coronary artery. Further provided herein are injectable compositions wherein the composition is suitable for adventitial delivery below the knee. Further provided herein are injectable compositions wherein the composition is suitable for adventitial delivery above the knee. Further provided herein are injectable compositions wherein the composition is suitable for adventitial delivery to a below-knee popliteal or tibial vessel. Further provided herein are injectable compositions wherein the composition is suitable for adventitial delivery to a femoral vessel. Further provided herein are injectable compositions wherein the therapeutically effective amount of temsirolimus is about 1 µg to 50 mg. Further provided herein are injectable compositions wherein the therapeutically effective amount of temsirolimus is about 10 µg to 20 mg. Further provided herein are injectable compositions wherein the therapeutically effective amount of temsirolimus is about 100 µg to 15 mg. Further provided herein are injectable compositions wherein the therapeutically effective amount of temsirolimus is about 100 µg to 5 mg. Further provided herein are injectable compositions wherein the therapeutically effective amount is determined by a longitudinal length of a target diseased artery. Further provided herein are injectable compositions wherein the therapeutically effective amount of dexamethasone is about 0.8 mg to 8 mg per cm of longitudinal length of a disease site in the blood vessel. Further provided herein are injectable compositions wherein the therapeutically effective amount of dexamethasone is about 0.05 mg to 10 mg per cm of longitudinal length of a disease site in the blood vessel and the therapeutically effective amount of temsirolimus is about 0.005 mg to 5 mg per cm of longitudinal length of a disease site in the blood vessel. Further provided herein are injectable compositions wherein the therapeutically effective amount of dexamethasone is about 0.1 mg to 2 mg per cm of longitudinal length of a disease site in the blood vessel and the therapeutically effective amount of temsirolimus is about 0.025 mg to 1 mg per cm of longitudinal length of the disease site in the blood vessel. Further provided herein are injectable compositions wherein the injection volume of the composition is about 0.01 mL to about 50 mL. Further provided herein are injectable compositions wherein the injection volume of the composition is about 0.5 mL to about 20 mL. Further provided herein are injectable compositions wherein the injection concentration of temsirolimus is about 0.01 mg/mL to about 2.0 mg/mL. Further provided herein are injectable compositions wherein the injection concentration of temsirolimus is about 0.1 mg/mL to about 0.5 mg/mL. Further provided herein are injectable compositions wherein the injection concentration of temsirolimus is about 0.4 mg/mL. Further provided herein are injectable compositions wherein the pharmaceutically acceptable excipient is 0.9% sodium chloride injection USP, dehydrated alcohol, dl-alpha tocopherol, anhydrous citric acid, polysorbate 80, polyethylene glycol 400, propylene glycol, or a combination thereof. Further provided herein are injectable compositions for use in treating restenosis. Further provided herein are injectable compositions for use in treating restenosis below the knee. Further provided herein are injectable compositions for use in treating restenosis above the knee. Further provided herein are injectable compositions for use in treating restenosis in a below-knee popliteal vessel or tibial vessel.

Provided herein are methods of treating a vascular disease in a subject in need thereof, the method comprising administering to the subject a therapeutically effective amount of a pharmaceutical composition described herein, wherein the composition is administered by direct injection to a disease site. Further provided herein are methods of treating a vascular disease wherein the composition is injected though a catheter with a needle. Further provided herein are methods of treating a vascular disease wherein the composition is injected distal or proximal to the disease site. Further provided herein are methods of treating a vascular disease wherein the composition is injected at least about 2 cm away from the disease site. Further provided herein are methods of treating a vascular disease wherein the composition is injected at or adjacent to the disease site. Further provided herein are methods of treating a vascular disease wherein the composition is administered by injection into the blood vessel. Further provided herein are methods of treating a vascular disease wherein the composition is injected into an adventitial tissue surrounding a blood vessel. Further provided herein are methods of treating a vascular disease wherein the composition is injected into a perivascular tissue surrounding the blood vessel. Further provided herein are methods of treating a vascular disease wherein the blood vessel is an artery. Further provided herein are methods of treating a vascular disease wherein the blood vessel is a vein. Further provided herein are methods of treating a vascular disease wherein the artery is a coronary artery or a peripheral artery. Further provided herein are methods of treating a vascular disease wherein the artery is selected from the group consisting of renal artery, cerebral artery, pulmonary artery, and artery in the leg. Further provided herein are methods of treating a vascular disease wherein the artery is below the knee. Further provided herein are methods of treating a vascular disease wherein the blood vessel is below-knee popliteal vessel or tibial vessel. Further provided herein are methods of treating a vascular disease wherein the composition is injected into a blood vessel wall. Further provided herein are methods of treating a vascular disease wherein the composition is injected into a tissue surrounding the blood vessel wall. Further provided herein are methods of treating a vascular disease wherein the therapeutically effective amount of temsirolimus is about 1 µg to 50 mg. Further provided herein are methods of treating a vascular disease wherein the therapeutically effective amount of temsirolimus is about 10 µg to 20 mg. Further provided herein are methods of treating a vascular disease wherein the therapeutically effective amount of temsirolimus is about 100 µg to 15 mg. Further provided herein are methods of treating a vascular disease wherein the therapeutically effective amount of temsirolimus is about 100 µg to 5 mg. Further provided herein are methods of treating a vascular disease wherein the therapeutically effective amount of dexamethasone is about 0.8 mg to 8 mg per cm of longitudinal length of the disease site in the blood vessel. Further provided herein are methods of treating a vascular disease wherein the therapeutically effective amount of dexamethasone is about 0.05 mg to 10 mg per cm of longitudinal length of the disease site in the blood vessel and the therapeutically effective amount of temsirolimus is about 0.005 mg to 5 mg per cm of longitudinal length of the disease site in the blood vessel. Further provided herein are methods of treating a vascular disease wherein the therapeutically effective amount of dexamethasone is about 0.1 mg to 2 mg per cm of longitudinal length of the disease site in the blood vessel and the therapeutically effective amount of temsirolimus is about 0.025 mg to 1 mg per cm of longitudinal length of the disease site in the blood vessel. Further provided herein are methods of treating a vascular disease wherein the injection volume of the composition is about 0.01 mL to about 50 mL. Further provided herein are methods of treating a vascular disease wherein the injection volume of the composition is about 0.5 mL to about 20 mL. Further provided herein are methods of treating a vascular disease wherein the injection concentration of temsirolimus is about 0.01 mg/mL to about 2.0 mg/mL. Further provided herein are methods of treating a vascular disease wherein the injection concentration of temsirolimus is about 0.1 mg/mL to about 0.4 mg/mL. Further provided herein are methods of treating a vascular disease wherein the injection concentration of temsirolimus is about 0.4 mg/mL. Further provided herein are methods of treating a vascular disease wherein the injection concentration of temsirolimus is about 0.1 mg/mL. Further provided herein are methods of treating a vascular disease wherein 12 months after administration of the pharmaceutical composition, vessel cross-sectional area at the disease site has decreased no more than 60%, when compared to vessel cross-sectional area at the disease site at the time of administration. Further provided herein are methods of treating a vascular disease wherein 12 months after administration of the pharmaceutical composition, vessel cross-sectional area at the disease site has decreased no more than 50%, when compared to vessel cross-sectional area at the disease site at the time of administration. Further provided herein are methods of treating a vascular disease wherein 12 months after administration of the pharmaceutical composition, vessel cross-sectional area at the disease site has decreased no more than 30%, when compared to vessel cross-sectional area at the disease site at the time of administration. Further provided herein are methods of treating a vascular disease wherein the subject is human. Further provided herein are methods of treating a vascular disease wherein the vascular disease is angina, myocardial infarction, congestive heart failure, cardiac arrhythmia, peripheral artery disease, claudication, or critical limb ischemia. Further provided herein are methods of treating a vascular disease wherein the vascular disease is atherosclerosis, bypass graft failure, transplant vasculopathy, vascular restenosis, or in-stent restenosis. Further provided herein are methods of treating a vascular disease wherein treating using the pharmaceutical composition results in a decrease in apoptosis at the disease site relative to treating using a pharmaceutical composition comprising either temsirolimus or a glucocorticoid. Further provided herein are methods of treating a vascular disease wherein treating using the pharmaceutical composition results in a decrease in necrosis at the disease site relative to treating using a pharmaceutical composition comprising either temsirolimus or a glucocorticoid.

Provided herein are methods of treating a vascular disease in an individual in need thereof, the method comprising administering to the subject a therapeutically effective amount of a first pharmaceutical composition and a second pharmaceutical composition, wherein the first pharmaceutical composition comprises temsirolimus, and the second pharmaceutical composition comprises a glucocorticoid, wherein the first composition and the second composition are each administered by injection.

Provided herein are methods of treating a peripheral artery disease in a human subject in need thereof, the method comprising administering to the human subject a therapeutically effective amount of a pharmaceutical composition comprising temsirolimus or pharmaceutically acceptable salt thereof, and a glucocorticoid or pharmaceutically acceptable salt thereof, and a pharmaceutically acceptable excipient, wherein the composition is administered by direct injection to or near a disease site in a wall of a peripheral artery via a laterally extending injection needle of a catheter advanced through vasculature of the human subject. Further provided herein are methods wherein the composition further comprises a contrast medium for visualizing the injection.

Provided herein are injectable compositions comprising temsirolimus and a glucocorticoid, or pharmaceutically acceptable salts thereof, and a pharmaceutically acceptable excipient for use in treating a vascular disease of a human subject, wherein the composition is suitable for adventitial delivery to a peripheral artery, wherein the composition is suitable for direct injection to a vascular disease site in a wall of the peripheral artery via a laterally extending needle from a catheter advanced through vasculature of the human subject. Further provided herein are methods wherein the composition further comprises a contrast medium for visualizing the injection.

Provided herein are pharmaceutical compositions comprising a cell division inhibitor and a glucocorticoid, or their pharmaceutically acceptable salts thereof. Further provided herein are pharmaceutical compositions wherein the glucocorticoid is dexamethasone or a pharmaceutically acceptable salt thereof. Further provided herein are pharmaceutical compositions wherein the ratio (by weight) of a cell division inhibitor to the glucocorticoid, or vice versa, is between 10:1 to 1:1. Further provided herein are pharmaceutical compositions wherein the composition is in an injectable dosage form. Further provided herein are pharmaceutical compositions wherein the composition further comprises at least one pharmaceutically acceptable excipient. Further provided herein are pharmaceutical compositions wherein the concentration of dexamethasone is 1.0-8.0 mg/mL. Further provided herein are pharmaceutical compositions wherein the concentration of dexamethasone is about 3.2 mg/mL. Further provided herein are pharmaceutical compositions wherein the concentration of dexamethasone is less than 4.0 mg/mL. Further provided herein are pharmaceutical compositions wherein the concentration of a cell division inhibitor is 0.01-2.0 mg/mL. Further provided herein are pharmaceutical compositions wherein the concentration of a cell division inhibitor is 0.05-0.5 mg/mL. Further provided herein are pharmaceutical compositions wherein the concentration of a cell division inhibitor is about 0.1 mg/mL. Further provided herein are pharmaceutical compositions wherein the concentration of a cell division inhibitor is about 0.4 mg/mL. Further provided herein are pharmaceutical compositions for use in treating restenosis. Further provided herein are pharmaceutical compositions for use in treating restenosis below the knee. Further provided herein are pharmaceutical compositions for use in treating restenosis above the knee. Further provided herein are pharmaceutical compositions for use in treating restenosis in a below-knee popliteal vessel or tibial vessel. Further provided herein are pharmaceutical compositions wherein the cell division inhibitor is paclitaxel.

Provided herein are injectable compositions comprising a cell division inhibitor or a pharmaceutically acceptable salt thereof, dexamethasone or a pharmaceutically acceptable salt thereof, and a pharmaceutically acceptable excipient. Further provided herein are injectable compositions wherein the composition is suitable for adventitial delivery. Further provided herein are injectable compositions wherein the composition is suitable for adventitial delivery to a coronary vessel. Further provided herein are injectable compositions wherein the composition is suitable for adventitial delivery to a coronary artery. Further provided herein are injectable compositions wherein the composition is suitable for adventitial delivery below the knee. Further provided herein are injectable compositions wherein the composition is suitable for adventitial delivery above the knee. Further provided herein are injectable compositions wherein the composition is suitable for adventitial delivery to a below-knee popliteal or tibial vessel. Further provided herein are injectable compositions wherein the composition is suitable for adventitial delivery to a femoral vessel. Further provided herein are injectable compositions wherein the therapeutically effective amount of a cell division inhibitor is about 1 µg to 50 mg. Further provided herein are injectable compositions wherein the therapeutically effective amount of a cell division inhibitor is about 10 µg to 20 mg. Further provided herein are injectable compositions wherein the therapeutically effective amount of a cell division inhibitor is about 100 µg to 15 mg. Further provided herein are injectable compositions wherein the therapeutically effective amount of a cell division inhibitor is about 100 µg to 5 mg. Further provided herein are injectable compositions wherein the therapeutically effective amount is determined by a longitudinal length of a target diseased artery. Further provided herein are injectable compositions wherein the therapeutically effective amount of dexamethasone is about 0.8 mg to 8 mg per cm of longitudinal length of a disease site in the blood vessel. Further provided herein are injectable compositions wherein the therapeutically effective amount of dexamethasone is about 0.05 mg to 10 mg per cm of longitudinal length of a disease site in the blood vessel and the therapeutically effective amount of a cell division inhibitor is about 0.005 mg to 5 mg per cm of longitudinal length of a disease site in the blood vessel. Further provided herein are injectable compositions wherein the therapeutically effective amount of dexamethasone is about 0.1 mg to 2 mg per cm of longitudinal length of a disease site in the blood vessel and the therapeutically effective amount of a cell division inhibitor is about 0.025 mg to 1 mg per cm of longitudinal length of the disease site in the blood vessel. Further provided herein are injectable compositions wherein the injection volume of the composition is about 0.01 mL to about 50 mL. Further provided herein are injectable compositions wherein the injection volume of the composition is about 0.5 mL to about 20 mL. Further provided herein are injectable compositions wherein the injection concentration of a cell division inhibitor is about 0.01 mg/mL to about 2.0 mg/mL. Further provided herein are injectable compositions wherein the injection concentration of a cell division inhibitor is about 0.1 mg/mL to about 0.5 mg/mL. Further provided herein are injectable compositions wherein the injection concentration of a cell division inhibitor is about 0.4 mg/mL. Further provided herein are injectable compositions wherein the pharmaceutically acceptable excipient is 0.9% sodium chloride injection USP, dehydrated alcohol, dl-alpha tocopherol, anhydrous citric acid, polysorbate 80, polyethylene glycol 400, propylene glycol, or a combination thereof. Further provided herein are injectable compositions for use in treating restenosis. Further provided herein are injectable compositions for use in treating restenosis below the knee. Further provided herein are injectable compositions for use in treating restenosis above the knee. Further provided herein are injectable compositions for use in treating restenosis in a below-knee popliteal vessel or tibial vessel. Further provided herein are injectable compositions wherein the cell division inhibitor is paclitaxel.

Provided herein are methods of treating a vascular disease in a subject in need thereof, the method comprising administering to the subject a therapeutically effective amount of a pharmaceutical composition described herein, wherein the composition is administered by direct injection to a disease site. Further provided herein are methods of treating a vascular disease wherein the composition is injected though a catheter with a needle. Further provided herein are methods of treating a vascular disease wherein the composition is injected distal or proximal to the disease site. Further provided herein are methods of treating a vascular disease wherein the composition is injected at least about 2 cm away from the disease site. Further provided herein are methods of treating a vascular disease wherein the composition is injected at or adjacent to the disease site. Further provided herein are methods of treating a vascular disease wherein the composition is administered by injection into a blood vessel. Further provided herein are methods of treating a vascular disease wherein the composition is injected into an adventitial tissue surrounding a blood vessel. Further provided herein are methods of treating a vascular disease wherein the composition is injected into a perivascular tissue surrounding the blood vessel. Further provided herein are methods of treating a vascular disease wherein the blood vessel is an artery. Further provided herein are methods of treating a vascular disease wherein the blood vessel is a vein. Further provided herein are methods of treating a vascular disease wherein the artery is a coronary artery or a peripheral artery. Further provided herein are methods of treating a vascular disease wherein the artery is selected from the group consisting of renal artery, cerebral artery, pulmonary artery, and artery in the leg. Further provided herein are methods of treating a vascular disease wherein the artery is below the knee. Further provided herein are methods of treating a vascular disease wherein the blood vessel is below-knee popliteal vessel or tibial vessel. Further provided herein are methods of treating a vascular disease wherein the composition is injected into a blood vessel wall. Further provided herein are methods of treating a vascular disease wherein the composition is injected into a tissue surrounding the blood vessel wall. Further provided herein are methods of treating a vascular disease wherein the therapeutically effective amount of a cell division inhibitor is about 1 µg to 50 mg. Further provided herein are methods of treating a vascular disease wherein the therapeutically effective amount of a cell division inhibitor is about 10 µg to 20 mg. Further provided herein are methods of treating a vascular disease wherein the therapeutically effective amount of a cell division inhibitor is about 100 µg to 15 mg. Further provided herein are methods of treating a vascular disease wherein the therapeutically effective amount of a cell division inhibitor is about 100 µg to 5 mg. Further provided herein are methods of treating a vascular disease wherein the therapeutically effective amount of dexamethasone is about 0.8 mg to 8 mg per cm of longitudinal length of the disease site in the blood vessel. Further provided herein are methods of treating a vascular disease wherein the therapeutically effective amount of dexamethasone is about 0.05 mg to 10 mg per cm of longitudinal length of the disease site in the blood vessel and the therapeutically effective amount of a cell division inhibitor is about 0.005 mg to 5 mg per cm of longitudinal length of the disease site in the blood vessel. Further provided herein are methods of treating a vascular disease wherein the therapeutically effective amount of dexamethasone is about 0.1 mg to 2 mg per cm of longitudinal length of the disease site in the blood vessel and the therapeutically effective amount of a cell division inhibitor is about 0.025 mg to 1 mg per cm of longitudinal length of the disease site in the blood vessel. Further provided herein are methods of treating a vascular disease wherein the injection volume of the composition is about 0.01 mL to about 50 mL. Further provided herein are methods of treating a vascular disease wherein the injection volume of the composition is about 0.5 mL to about 20 mL. Further provided herein are methods of treating a vascular disease wherein the injection concentration of a cell division inhibitor is about 0.01 mg/mL to about 2.0 mg/mL. Further provided herein are methods of treating a vascular disease wherein the injection concentration of a cell division inhibitor is about 0.1 mg/mL to about 0.4 mg/mL. Further provided herein are methods of treating a vascular disease wherein the injection concentration of a cell division inhibitor is about 0.4 mg/mL. Further provided herein are methods of treating a vascular disease wherein the injection concentration of a cell division inhibitor is about 0.1 mg/mL. Further provided herein are methods of treating a vascular disease wherein 12 months after administration of the pharmaceutical composition, vessel cross-sectional area at the disease site has decreased no more than 60%, when compared to vessel cross-sectional area at the disease site at the time of administration. Further provided herein are methods of treating a vascular disease wherein 12 months after administration of the pharmaceutical composition, vessel cross-sectional area at the disease site has decreased no more than 50%, when compared to vessel cross-sectional area at the disease site at the time of administration. Further provided herein are methods of treating a vascular disease wherein 12 months after administration of the pharmaceutical composition, vessel cross-sectional area at the disease site has decreased no more than 30%, when compared to vessel cross-sectional area at the disease site at the time of administration. Further provided herein are methods of treating a vascular disease wherein the subject is human. Further provided herein are methods of treating a vascular disease wherein the vascular disease is angina, myocardial infarction, congestive heart failure, cardiac arrhythmia, peripheral artery disease, claudication, or critical limb ischemia. Further provided herein are methods of treating a vascular disease wherein the vascular disease is atherosclerosis, bypass graft failure, transplant vasculopathy, vascular restenosis, or in-stent restenosis. Further provided herein are methods of treating a vascular disease wherein treating using the pharmaceutical composition results in a decrease in apoptosis at the disease site relative to treating using a pharmaceutical composition comprising either a cell division inhibitor or a glucocorticoid. Further provided herein are methods of treating a vascular disease wherein treating using the pharmaceutical composition results in a decrease in necrosis at the disease site relative to treating using a pharmaceutical composition comprising either a cell division inhibitor or a glucocorticoid. Further provided herein are methods wherein the cell division inhibitor is paclitaxel.

Provided herein are methods of treating a vascular disease in an individual in need thereof, the method comprising administering to the subject a therapeutically effective amount of a first pharmaceutical composition and a second pharmaceutical composition, wherein the first pharmaceutical composition comprises a cell division inhibitor, and the second pharmaceutical composition comprises a glucocorticoid, wherein the first composition and the second composition are each administered by injection. Further provided herein are methods wherein the cell division inhibitor is paclitaxel.

Provided herein are methods of treating a peripheral artery disease in a human subject in need thereof, the method comprising administering to the human subject a therapeutically effective amount of a pharmaceutical composition comprising a cell division inhibitor or pharmaceutically acceptable salt thereof, and a glucocorticoid or pharmaceutically acceptable salt thereof, and a pharmaceutically acceptable excipient, wherein the composition is administered by direct injection to or near a disease site in a wall of a peripheral artery via a laterally extending injection needle of a catheter advanced through vasculature of the human subject. Further provided herein are methods wherein the composition further comprises a contrast medium for visualizing the injection. Further provided herein are methods wherein the cell division inhibitor is paclitaxel.

Provided herein are injectable compositions comprising a cell division inhibitor and a glucocorticoid, or pharmaceutically acceptable salts thereof, and a pharmaceutically acceptable excipient for use in treating a vascular disease of a human subject, wherein the composition is suitable for adventitial delivery to a peripheral artery, wherein the composition is suitable for direct injection to a vascular disease site in a wall of the peripheral artery via a laterally extending needle from a catheter advanced through vasculature of the human subject. Further provided herein are methods wherein the composition further comprises a contrast medium for visualizing the injection. Further provided herein are injectable compositions wherein the cell division inhibitor is paclitaxel.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 10A is a cross-sectional view of a step in the inflation process of an intraluminal injection catheter useful in the methods of the present disclosure.

FIG. 10B is a cross-sectional view of a step in the inflation process of an intraluminal injection catheter useful in the methods of the present disclosure.

FIG. 10C is a cross-sectional view of a step in the inflation process of an intraluminal injection catheter useful in the methods of the present disclosure.

FIG. 10D is a cross-sectional view of a step in the inflation process of an intraluminal injection catheter useful in the methods of the present disclosure.

FIG. 11A is a cross-sectional view of the inflated intraluminal injection catheter useful in the methods of the present disclosure, illustrating the ability to treat multiple lumen diameters.

FIG. 11B is a cross-sectional view of the inflated intraluminal injection catheter useful in the methods of the present disclosure, illustrating the ability to treat multiple lumen diameters.

FIG. 11C is a cross-sectional view of the inflated intraluminal injection catheter useful in the methods of the present disclosure, illustrating the ability to treat multiple lumen diameters.

DETAILED DESCRIPTION

Figure 1A:
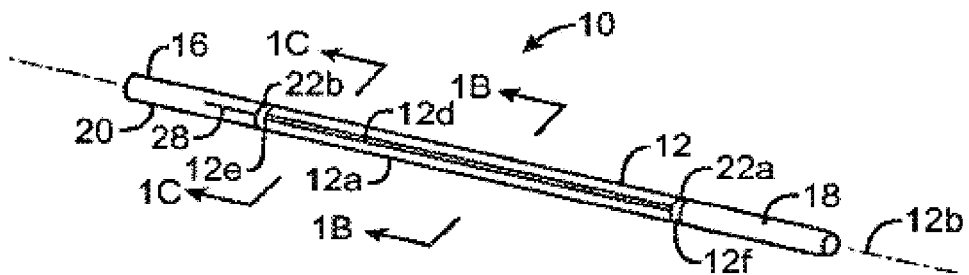
FIG. 1A is a schematic, perspective view of an intraluminal injection catheter suitable for use in the methods and systems of the present disclosure.

Provided herein are methods, devices, and compositions for the treatment of cardiovascular diseases, such as restenosis. Various aspects of the methods, devices, and compositions comprise combinations of an mTOR inhibitor (such as temsirolimus) or a cell division inhibitor (such as paclitaxel) and a glucocorticoid (such as dexamethasone), or their pharmaceutically acceptable salts. In some cases, the compositions are administered by direct injection to the disease site.

Diseases and Conditions

Blockages form in blood vessels under various disease conditions. Atherosclerosis, which causes the narrowing, or stenosis, of arteries in the body, particularly in the heart, legs, carotid, and renal anatomy, leads to tissue ischemia from lack of blood flow. In some instances, atherosclerosis in the coronary arteries causes myocardial infarction, commonly referred to as a heart attack, which can be immediately fatal, or even if survived, causes damage to the heart which can incapacitate the patient. Other coronary diseases include congestive heart failure, vulnerable or unstable plaque, and cardiac arrhythmias, which cause death and incapacitation. In addition, peripheral artery disease (PAD), where the arteries in peripheral tissues narrow, most commonly affects the leg, renal, and carotid arteries. In some instances, blood clots and thrombus in the peripheral vasculature occlude peripheral blood flow, leading to tissue and organ necrosis. Some patients with PAD experience critical limb ischemia that results in ulcers and some instances requires amputation in the worst cases. In some instances, PAD in a renal artery causes renovascular hypertension, and clots in the carotid artery embolize and travel to the brain, potentially causing ischemic stroke.

To improve blood flow to downstream tissues, various revascularization methods are used to bypass or open the artery. In some instances, artery bypass surgery is an effective treatment for stenosed, or narrowed, arteries resulting from atherosclerosis and other causes, but it is a highly invasive procedure, expensive, requires substantial hospital and recovery time. In some instances, mechanical revascularization methods with balloon angioplasty, atherectomy, stenting, or surgical endarterectomy are used to open, or dilate, the artery. For example, percutaneous transluminal angioplasty (PTA), commonly referred to as balloon angioplasty, is less invasive, less traumatic, and significantly less expensive than bypass surgery. In addition, the effectiveness of balloon angioplasty has improved with the introduction of stenting which involves the placement of a scaffold structure within the artery which has been treated by balloon angioplasty. The stent inhibits abrupt re-closure of the artery and has some benefit in reducing subsequent restenosis resulting from hyperplasia. By salvaging blood vessels rather than bypassing them, more options are left available to physicians in the further treatment of the disease.

Unfortunately, in some instances, mechanical revascularization procedures lead to an injury cascade that causes the artery to stiffen and arterial walls to thicken with a scar-like tissue, known as neointimal hyperplasia. In some instances, not only does the inner wall of the artery (i.e., the intima) thicken and stiffen in response to the injury cascade, but the media (i.e., the middle tissue layer of the wall) and the adventitia (i.e., the outer layer of the wall) can thicken and stiffen as well. The thickening (or hyperplasia) and the stiffening (or sclerosis), reduces the blood flow to tissues distal to the affected site. As a result, patients who have undergone mechanical revascularization procedures in some instances suffer from a high incidence of restenosis resulting from hyperplasia. Restenosis, or recurrence of stenosis or narrowing, of the blood vessel may necessitate another revascularization procedure to the affected area again.

Inflammatory restenosis and reocclusion in some cases occurs due to hyperplasia and sclerosis. The resolution of an inflammatory impetus in some instances leads to a stiff, narrow vessel or a functioning artery with vasomotor actions (including the ability to dilate or constrict based on signals received from the body's endocrine system. In order to maintain long-term vascular patency, the vessel must be allowed to heal without sclerosis or hyperplasia.

Some embodiments herein describe compositions and methods for reducing the buildup of sclerosis and hyperplasia following mechanical revascularization.

In some embodiments, implanting stents coated with anti-proliferative drugs reduces the occurrence of hyperplasia. For example, mechanical endovascular revascularization alone leads to patency (the binary measure of vessel openness, typically greater than 50% in diameter compared to adjacent non-diseased vessel) rates of 33-55% at one year and 20-50% at two years, while drug-coated balloons and adventitial drug delivery have shown an ability to improve patency to better than 80% at one year and 65-70% at 2 years.

Pharmaceutical Compositions

Cell Division Inhibitors

Described herein are pharmaceutical compositions comprising a cell division inhibitor, a glucocorticoid (such as dexamethasone or a pharmaceutically acceptable salt thereof), and a pharmaceutically acceptable excipient. Some embodiments herein describe a pharmaceutical composition comprising a microtubule stabilizer (such as a taxane or a pharmaceutically acceptable salt thereof), a glucocorticoid (such as dexamethasone or a pharmaceutically acceptable salt thereof), and a pharmaceutically acceptable excipient. Some embodiments herein describe a pharmaceutical composition comprising an mTOR inhibitor (such as temsirolimus or a pharmaceutically acceptable salt thereof), a glucocorticoid (such as dexamethasone or a pharmaceutically acceptable salt thereof), and a pharmaceutically acceptable excipient. Other embodiments herein describe a pharmaceutical composition comprising a taxane (such as paclitaxel or a pharmaceutically acceptable salt thereof), a glucocorticoid (such as dexamethasone or a pharmaceutically acceptable salt thereof), and a pharmaceutically acceptable excipient. In some embodiments, the pharmaceutical compositions are useful for treating the diseases and condition described herein (e.g., reducing the buildup of sclerosis and hyperplasia following mechanical revascularization).

mTOR Inhibitors

In certain embodiments, the pharmaceutical compositions described herein comprise an mTOR inhibitor, such as a -limus drug. In some cases, the mTOR inhibitor is sirolimus, everolimus, zotarolimus, deforolimus, biolimus, temsirolimus, or combinations thereof. The pharmaceutical compositions disclosed herein in some instances comprise temsirolimus or its pharmaceutically acceptable salts thereof. In some embodiments, the mTOR inhibitor is Torisel®.

The pharmaceutical compositions disclosed herein in some instances comprise temsirolimus or its pharmaceutically acceptable salts thereof. In some instances, the pharmaceutical compositions comprise pharmaceutically acceptable excipients. In some instances, the pharmaceutical compositions further comprise excipients including 0.9% sodium chloride injection USP, dehydrated alcohol, dl-alpha tocopherol, anhydrous citric acid, polysorbate 80, polyethylene glycol 400, propylene glycol, or a combination thereof. In some instances, the pharmaceutical compositions comprise nanoparticle formulations. In some instances, the pharmaceutical compositions further comprise excipients including albumin. In some instances, the pharmaceutical compositions comprise other excipients commonly used in injectable compositions. In some instances, the pharmaceutical compositions comprise a contrast agent to aid in visualization of the delivery of the pharmaceutical composition. In some instances, the pharmaceutical compositions comprising temsirolimus are injectable. In some instances, the pharmaceutical composition is a liquid, a suspension, a solution, or a gel.

Taxanes

In certain embodiments, the pharmaceutical compositions described herein comprise a cell division inhibitor, such as a taxane drug. In some cases, the cell division inhibitor is paclitaxel, docetaxel, cabazitaxel, or combinations thereof. The pharmaceutical compositions disclosed herein in some instances comprise paclitaxel or its pharmaceutically acceptable salts thereof. In some embodiments, the cell division inhibitor is Abraxane®.

The pharmaceutical compositions disclosed herein in some instances comprise paclitaxel or its pharmaceutically acceptable salts thereof. In some instances, the pharmaceutical compositions comprise pharmaceutically acceptable excipients. In some instances, the pharmaceutical compositions further comprise excipients including cremophor EL, ethanol, or a combination thereof. In some instances, the pharmaceutical compositions comprise nanoparticle formulations. In some instances, the pharmaceutical compositions further comprise excipients including albumin. In some instances, the pharmaceutical compositions comprise other excipients commonly used in injectable compositions. In some instances, the pharmaceutical compositions comprise a contrast agent to aid in visualization of the delivery of the pharmaceutical composition. In some instances, the pharmaceutical compositions comprising paclitaxel are injectable. In some instances, the pharmaceutical composition is a liquid, a suspension, a solution, or a gel. In some instances, pharmaceutical compositions comprise an antihistamine. In some instances, pharmaceutical compositions comprise solubilizing agents, such as polyols, glycols, or glycerols. In some instances, pharmaceutical compositions comprise macrogolglycerol ricinoleate.

Glucocorticoids

In some instances, the pharmaceutical compositions disclosed herein comprise one or more glucocorticoids, such as dexamethasone, prenisolone, prednisone, triamcinoclone, hydrocortisone, methylpredinisolone, budesonide, betamethasone, deflazacort, beclomethasone, cortisone, or any other compound that targets the glucocorticoid receptor (GR). In some embodiments, the glucocorticoid is dexamethasone.

The pharmaceutical compositions disclosed herein in some instances comprise dexamethasone or its pharmaceutically acceptable salts thereof. In some instances, dexamethasone is dexamethasone sodium phosphate injection. In some instances, the pharmaceutical compositions further comprise anhydrous citric acid, sodium sulfite, benzyl alcohol, sodium citrate, water for injection, or a combination thereof. In some instances, the pharmaceutical compositions comprise pharmaceutically acceptable excipients. In some instances, the pharmaceutical compositions comprise other excipients commonly used in injectable compositions. In some instances, the pharmaceutical compositions comprise a contrast agent to aid in visualization of the delivery of the pharmaceutical composition. In some instances, the pharmaceutical composition is injectable. In some instances, the pharmaceutical composition is a liquid, a suspension, a solution, or a gel.

Combination of Cell Division Inhibitors and Glucocorticoids mTOR Inhibitors and Glucocorticoids In certain embodiments, a cell division inhibitor, such as an mTOR inhibitor and/or a glucocorticoid (such as dexamethasone) as described herein is administered as a pure chemical. In other embodiments, the combination of mTOR inhibitor and a glucocorticoid described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)). In some embodiments, an mTOR inhibitor (such as temsirolimus) and a glucocorticoid (e.g., dexamethasone) are each administered as individual compositions. In some embodiments, individual compositions of an mTOR inhibitor or a glucocorticoid are combined with a suitable or acceptable excipient.

In some embodiments, mTOR inhibitor (such as temsirolimus) and a glucocorticoid (e.g., dexamethasone) are administered as a single, combined composition.

Provided herein are pharmaceutical compositions comprising an mTOR inhibitor, and a glucocorticoid together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

In certain embodiments, an mTOR inhibitor and/or a glucocorticoid as described herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

In some instances, the pharmaceutical compositions comprise an mTOR inhibitor and a glucocorticoid, and one or more pharmaceutically acceptable excipients. In some instances, pharmaceutical compositions comprising an mTOR inhibitor, glucocorticoid, or combination thereof comprise (by way of non-limiting example) excipients such as 0.9% sodium chloride injection USP, dehydrated alcohol, dl-alpha tocopherol, anhydrous citric acid, polysorbate 80, polyethylene glycol 400, propylene glycol, benzyl alcohol, sodium citrate, sodium sulfite, albumin, or any combination thereof. In some instances, the pharmaceutical compositions comprise nanoparticles. In some instances, the pharmaceutical compositions comprise other excipients commonly used in injectable compositions. In some instances, the pharmaceutical compositions comprise a contrast agent to aid in visualization of the delivery of the pharmaceutical composition. In some instances, the pharmaceutical compositions a liquid, a suspension, a solution, or a gel. In some instances, the pharmaceutical compositions comprising an mTOR inhibitor, a glucocorticoid, or combination thereof are injectable. In some instances, pharmaceutical compositions comprise excipients that solubilize an mTOR inhibitor, a glucocorticoid, or a combination thereof. In another embodiment, the pharmaceutical compositions comprising an mTOR inhibitor and a glucocorticoid are provided in a dosage form for parenteral administration, which comprises one or more pharmaceutically acceptable excipients or carriers. In some instances, the pharmaceutical compositions comprising an mTOR inhibitor, a glucocorticoid, or combination thereof are injectable. Where pharmaceutical compositions are formulated for intravenous, cutaneous or subcutaneous injection, the active ingredient is in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, excipients, buffers, antioxidants, and/or other additives are included.

In some instances, a pharmaceutical composition comprising an mTOR inhibitor (such as temsirolimus) and a glucocorticoid (such as dexamethasone) is administered as a formulation comprising both drugs. In some instances, the percent by weight of temsirolimus to the glucocorticoid or vice versa is between 10:1 to 1:1. In some instances, the percent by weight of temsirolimus to the glucocorticoid or vice versa is between 7:1 to 2:1. In some instances, the percent by weight of temsirolimus to the glucocorticoid or vice versa is between 5:1 to 1:1. In some instances, the percent by weight of temsirolimus to the glucocorticoid or vice versa is between 3:1 to 1:1 In some instances, the percent by weight of temsirolimus to the glucocorticoid or vice versa is about 10:1, or about 9:1, about 8:1, about 7:1, about 6:1, about 5:1, about 4:1, about 3:1, about 2:1, or about 1:1. In some instances, the percent by weight of temsirolimus to the glucocorticoid or vice versa is 10:1 to 1:1, 7:1 to 2:1, 5:1 to 1:1, or 3:1 to 1:1.

Taxanes and Glucocorticoids

In certain embodiments, the combination of a cell division inhibitor (such as paclitaxel) and/or a glucocorticoid (such as dexamethasone) as described herein is administered as a pure chemical. In other embodiments, the combination of cell division inhibitor and a glucocorticoid described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)). In some embodiments, a cell division inhibitor (such as paclitaxel) and a glucocorticoid (e.g., dexamethasone) are each administered as individual compositions. In some embodiments, individual compositions of a cell division inhibitor or a glucocorticoid are combined with a suitable or acceptable excipient.

In some embodiments, a cell division inhibitor (such as paclitaxel) and a glucocorticoid (e.g., dexamethasone) are administered as a single, combined composition.

Provided herein are pharmaceutical compositions comprising a cell division inhibitor, and a glucocorticoid together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

In certain embodiments, a cell division inhibitor and/or a glucocorticoid as described herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

In some instances, the pharmaceutical compositions comprise a cell division inhibitor and a glucocorticoid, and one or more pharmaceutically acceptable excipients. In some instances, pharmaceutical compositions comprising a cell division inhibitor, glucocorticoid, or combination thereof comprise (by way of non-limiting example) excipients such as 0.9% sodium chloride injection USP, dehydrated alcohol, dl-alpha tocopherol, anhydrous citric acid, polysorbate 80, polyethylene glycol 400, propylene glycol, benzyl alcohol, sodium citrate, sodium sulfite, cremophor EL, albumin, or any combination thereof. In some instances, the pharmaceutical compositions comprise nanoparticles. In some instances, the pharmaceutical compositions comprise other excipients commonly used in injectable compositions. In some instances, the pharmaceutical compositions comprise a contrast agent to aid in visualization of the delivery of the pharmaceutical composition. In some instances, the pharmaceutical compositions comprise a liquid, a suspension, a solution, or a gel. In some instances, the pharmaceutical compositions comprising a cell division inhibitor, a glucocorticoid, or combination thereof are injectable. In some instances, pharmaceutical compositions comprise excipients that solubilize a cell division inhibitor, a glucocorticoid, or a combination thereof. In another embodiment, the pharmaceutical compositions comprising a cell division inhibitor and a glucocorticoid are provided in a dosage form for parenteral administration, which comprises one or more pharmaceutically acceptable excipients or carriers. In some instances, the pharmaceutical compositions comprising a cell division inhibitor, a glucocorticoid, or combination thereof are injectable. Where pharmaceutical compositions are formulated for intravenous, cutaneous or subcutaneous injection, the active ingredient is in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, excipients, buffers, antioxidants, and/or other additives are included.

In some instances, a pharmaceutical composition comprising a cell division inhibitor (such as paclitaxel) and a glucocorticoid (such as dexamethasone) is administered as a formulation comprising both drugs. In some instances, the percent by weight of paclitaxel to the glucocorticoid or vice versa is between 10:1 to 1:1. In some instances, the percent by weight of paclitaxel to the glucocorticoid or vice versa is between 7:1 to 2:1. In some instances, the percent by weight of paclitaxel to the glucocorticoid or vice versa is between 5:1 to 1:1. In some instances, the percent by weight of paclitaxel to the glucocorticoid or vice versa is between 3:1 to 1:1 In some instances, the percent by weight of paclitaxel to the glucocorticoid or vice versa is about 10:1, or about 9:1, about 8:1, about 7:1, about 6:1, about 5:1, about 4:1, about 3:1, about 2:1, or about 1:1. In some instances, the percent by weight of paclitaxel to the glucocorticoid or vice versa is 10:1 to 1:1, 7:1 to 2:1, 5:1 to 1:1, or 3:1 to 1:1.

Methods of Treatment

In atherosclerosis, bypass graft failure, transplant vasculopathy, and in-stent restenosis, the activation and proliferation of vascular smooth muscle cells (VSMCs) located in the vessel wall are linked to inflammation, apoptosis, and matrix alterations observed in these pathophysiologic diseases. An established strategy for the treatment of these conditions is to inhibit cellular proliferation through the use of paclitaxel. Paclitaxel has cytotoxic effects and may not provide the most durable solution for vascular pathologies. Some embodiments herein describe the use of mTOR inhibitors combined with glucocorticoids to provide a safer and more superior approach to the regulation of activated VSMCs compared to anti-proliferatives such as paclitaxel. Other embodiments herein describe the use of cell division inhibitors such as paclitaxel combined with glucocorticoids to provide safer and more superior approaches to the regulation of activated VSMCs compared to anti-proliferatives such as paclitaxel used alone.

Mechanistic target of rapamycin (mTOR) inhibitors have been identified drugs for treating vascular disease. A member of phosphatidylinositol-3 kinase-related kinase (PI3K) family, mTOR is involved in regulating cell growth, proliferation, cell survival and angiogenesis. In response to physical insult of revascularization procedure, smooth muscle and endothelial cells in blood vessels activate stress response pathways, which lead to cell proliferation, secretion of pro-inflammatory mediators and extracellular matrix components, and ultimately to restenosis. In some instances, drugs successful in blocking one or more of the stress response pathways decrease the degree of restenosis. In certain instances, mTOR inhibitors reduce cellular proliferation and inflammation and have been used successfully in graft-versus-host disease, in organ transplant and in some cancers by blocking mTOR activation in response to insulin, growth factors and amino acids.

mTOR inhibitors include the original mTOR inhibitor, sirolimus, also known as rapamycin, and the analogs of sirolimus. These analogs include everolimus, zotarolimus, deforolimus, biolimus and temsirolimus.

Temsirolimus is approved for the treatment of renal cell carcinoma (RCC), but it is not approved for the treatment of vascular restenosis. Temsirolimus has been described as a prodrug for sirolimus (i.e., temsirolimus is metabolized to the active agent sirolimus). As there are fewer metabolic reactions in the vascular tissue compared to the liver (where systemic drugs are generally metabolized), one would not expect temsirolimus to be efficacious when administered directly to vascular and other luminal walls. Some embodiments provided herein describe temsirolimus as an active agent useful for inhibiting mTOR and disrupting the mitosis of cells. In some embodiments, temsirolimus is useful for the treatment of vascular disease. In further or additional embodiments, temsirolimus is useful for the treatment of vascular disease via direct injection into vascular or other luminal walls. In further or additional embodiments, temsirolimus in combination with a glucocorticoid (e.g., dexamethasone) is useful for the treatment of vascular disease via direct injection into vascular or other luminal walls.

Also described herein are methods, devices, and compositions wherein in some embodiments a synergistic effect is observed for the combination of -limus analogs (such as temsirolimus) with corticosteroids (such as dexamethasone) for their ability to reduce the signals causing hyperplasia and sclerosis and to further reduce the cellular activities which apparently cause hyperplasia and sclerosis. Further described herein are methods wherein, in an attempt to influence the healing process, the combination of dexamethasone and temsirolimus, exemplary agents chosen from the category of corticosteroids (such as glucocorticoids) and mTOR inhibitors, respectively, target the disease process. In other methods described herein, the combination of dexamethasone and paclitaxel, exemplary agents chosen from the category of corticosteroids (such as glucocorticoids) and cell division inhibitors, respectively, target the disease process. In other methods described herein, the combination of dexamethasone and paclitaxel, exemplary agents chosen from the category of corticosteroids (such as glucocorticoids) and cell division inhibitors, respectively, influences the healing process. In some embodiments, the deployment or delivery of the drug takes place from the luminal side via drug-coated balloons or pressurized catheters, or from within the vessel wall (the media, the adventitia, or the perivascular tissues) with the use of needle injection catheters that deploy a needle from the inside to the outside of the artery. In some embodiments, drug delivery is accomplished using ultrasound guidance and penetration of a needle through the skin and surrounding tissues to the perivascular area in order to bathe the target tissues in the combination drug.

Subjects treated by the methods disclosed herein can exhibit a vascular disease. In one example, the vascular disease is atherosclerosis in the heart, legs, carotid, or renal blood vessels. In another example, the vascular disease is peripheral artery disease (PAD). In another example, the vascular disease is angina, myocardial infarction, congestive heart failure, cardiac arrhythmia, peripheral artery disease, claudication, or critical limb ischemia. In another example, the vascular disease is atherosclerosis, bypass graft failure, transplant vasculopathy, in-stent restenosis, or restenosis. In one example, the vascular disease is blood clots, thrombus, or other blockages in a blood vessel that may occlude peripheral blood flow, leading to tissue and organ necrosis. In one example, the vascular disease is PAD in renal artery or carotid artery. In some examples, the subject with restenosis had a procedure to improve the patency of the blood vessel or a revascularization procedure previously. In some instances, the vascular disease is restenosis.

In some cases, the disease site of the vascular disease includes blood vessels and the tissues surrounding the blood vessel. The vasculature of a subject refers to the circulatory system and in some instances comprises the arterial system, venous systems, or both arterial and venous systems and the blood vessels within those systems. In some examples, the blood vessel is an artery, arteriole, or other blood vessels of the arterial system. In some examples, the blood vessel is a vein, venule, or other blood vessels of the venous system. In one example, the artery is a coronary artery or a peripheral artery. In one example, the artery is below the knee. In another example, the artery is in the leg above the knee. In another example, the blood vessel is below-knee popliteal vessel or tibial vessel. In some examples, the blood vessel is a femoral vessel. In some examples, the artery is renal artery, carotid artery, cerebral artery, pulmonary artery, or artery in the leg. In some examples, the artery is a femoral artery.

Restenosis is in various tissues and blood vessels in the body. In some instances, the restenosis is in a coronary vessel. In some instances, the restenosis is in a coronary artery. In some instances, the restenosis is in a peripheral artery. In some instances, the restenosis is in the leg. In other instances, the restenosis is below the knee or in the leg above the knee. In some instances, the restenosis is in a below-knee popliteal vessel or tibial vessel. In some instances, the restenosis is in a femoral vessel. In other instances, the restenosis is in a femoral artery.

In some instances, the tissue surrounding a blood vessel refers to any tissues outside the endothelial cell wall of the blood vessel that is radially away from the lumen of the blood vessel in a cross section and includes plaque and calcification. In some instances, the tissue surrounding a blood vessel comprises adventitial tissue, perivascular tissue, or any tissue surrounding the endothelial wall of a blood vessel. In some instances, adventitial tissue is also known as adventitia or tunica adventitia or tunica externa. In some instances, adventitial tissue is outside of the external elastic membrane. In some instances, the tissue surrounding a blood vessel is tissues outside the tunica intima of the blood vessel. In some instances, the tissue surrounding a blood vessel is tissues outside the tunica media of the blood vessel. In some instances, the tissue surrounding a blood vessel is tissues outside the internal elastic membrane. In some instances, the tissue is a connective tissue. In some instances, the tissue is diseased tissue such as plaque, fibrosis, calcification, or combinations of diseased and healthy tissues.

In some instances, "patency" refers to blood vessel openness. In some instances, patency at the disease site refers to patency of the blood vessel, or blood vessel openness, at the disease site. In some instances, vessel cross-sectional area at the disease site refers to patency of the blood vessel at the disease site. In some instances, vessel cross-sectional area is determined by angiography. In some instances, the angiography is quantitative vascular angiography (QVA). In other instances, vessel cross-sectional area is determined by intravascular ultrasound (IVUS). In some instances, patency is described as percent of diameter of the lumen of the blood vessel that is open and unobstructed. In some instances, patency is described as percent of cross sectional area of the lumen of the blood vessel, or vessel cross-sectional area, that is open and unobstructed. In other instances, patency is the percent of luminal volume that is open and unobstructed. In some instances, patency requires determination of the boundaries of the endothelial wall of the blood vessel. In some instances, a blood vessel that is completely open and unobstructed has 100% patency; i.e., the blood vessel has a cross-sectional area that is healthy and typical of a normal, healthy blood vessel in the same part of the body. In some instances, a blood vessel that is completely blocked and obstructed has 0% patency. In some instances, patency is the binary measure of openness greater than 50% in diameter compared to adjacent non-diseased vessel. In some instances, patency is the binary measure of openness greater than 50% in cross-sectional area compared to adjacent non-diseased vessel. In some instances, patency is the binary measure of openness greater than 50% in luminal volume compared to adjacent non-diseased vessel.

Dosages/Administration

In some instances, a "therapeutically effective amount" refers to an amount of drug (e.g., temsirolimus or dexamethasone) that increases vessel cross-sectional area at the disease site. In some instances, therapeutically effective refers to increasing the vessel cross-sectional area at the disease site after administration of a pharmaceutical composition. In some instances, therapeutically effective refers to minimally decreasing the vessel cross-sectional area at the disease site after administration when compared to the vessel cross-sectional area at the disease site at the time of administration. In some instances, therapeutically effective refers to increasing the vessel cross-sectional area at the disease site. In some instances, therapeutically effective refers to increasing minimally the vessel cross-sectional area at the disease site after administration when compared to the vessel cross-sectional area at the disease site at the time of administration. In some instances, therapeutically effective refers to decreasing the vessel cross-sectional area at the disease site no more than 30%, 20%, 10%, or 0% when compared to the vessel cross-sectional area at the disease site at the time of administration; in other words the patency decreases no more than 30%, 20%, 10%, or 0% when compared to the patency at the disease site at the time of administration. In some instances, the vessel cross-sectional area at the disease site decreases no more than 60%, 50%, 40%, 30%, 20%, or 10% when compared to vessel cross-sectional area at the disease site at the time of administration. In some instances, the vessel cross-sectional area at the disease site increases at least 60%, 50%, 40%, 30%, 20%, or 10% when compared to vessel cross-sectional area at the disease site at the time of administration.

In some instances, the pharmaceutical composition is injected at various locations at or near the disease site. In some instances, the disease site refers to a blood vessel affected by a vascular disease. In some instances, the disease site refers to a blood vessel with a partial or complete blockage of the lumen. In some instances, the disease site refers to a blood vessel with a vessel cross-sectional area of less than 100%, 90%, 80%, 70%, 60%, 50%, 40%, 30%, 20%, 10%, or 0% of vessel cross-sectional area of an unobstructed vessel as determined from the vessel wall. In some instances, the pharmaceutical composition is injected distal or proximal to the disease site. In some instances, the pharmaceutical composition is injected at least about 2 cm away from the disease site. In some instances, the pharmaceutical composition is injected at or adjacent to the disease site. In some instances, the pharmaceutical composition is injected into a blood vessel. In some instances, the pharmaceutical composition is injected into an adventitial tissue surrounding a blood vessel. In some instances, the pharmaceutical composition is injected into a perivascular tissue surrounding a blood vessel.

Temsirolimus administered as part of a combination therapy with a glucocorticoid in some instances has a range of doses that are therapeutically effective for treating the vascular disease. In some instances, the therapeutically effective amount of temsirolimus is about 1 µg to 50 mg, about 10 µg to 20 mg, about 25 µg to 10 mg, about 1 µg to 2 mg, about 10 µg to 500 µg, about 100 µg to about 2 mg or about 100 µg to 500 µg. In some instances, the therapeutically effective amount of temsirolimus is about 100 µg to 5 mg. In some instances, the therapeutically effective amount of temsirolimus is about 100 µg to 15 mg. In some instances, the therapeutically effective amount of temsirolimus is about 10 µg, about 25 µg, about 50 µg, about 100 µg, about 500 µg, about 1.0 mg, about 5.0 mg, about 10.0 mg, or about 15.0 mg. In some instances, the therapeutically effective volume of temsirolimus is about 0.01 ml to about 50 ml, about 0.5 ml to about 20 ml, about 0.5 ml to about 25 ml, about 0.5 ml to about 5 ml, or about 1 ml to about 5 ml. In some instances, the therapeutically effective concentration of temsirolimus is about 0.1 mg/mL to about 0.4 mg/mL, about 0.1 mg/mL to about 0.5 mg/mL, or about 0.01 mg/mL to about 2.0 mg/mL. In some instances, the therapeutically effective concentration of temsirolimus is about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, or 3.0 mg/ml. In some instances, the therapeutically effective amount of temsirolimus is about 0.005 mg to 5 mg per cm of longitudinal length of the disease site in the blood vessel, about 0.025 mg to 1 mg per cm of longitudinal length of the disease site in the blood vessel, about 0.05 mg to 2 mg per cm of longitudinal length of the disease site in the blood vessel, or about 0.1 mg to 1 mg per cm of longitudinal length of the disease site in the blood vessel. In some instances, the therapeutically effective amount of temsirolimus is about 0.025 mg to 1 mg per cm of longitudinal length of the blood vessel. The longitudinal length of the disease site in the blood vessel, also known as the longitudinal length of the lesion, is about 1 cm, 5 cm, 10 cm, 20 cm, 30 cm, 40 cm, or 50 cm.

Paclitaxel administered as part of a combination therapy with a glucocorticoid in some instances has a range of doses that are therapeutically effective for treating the vascular disease. In some instances, the therapeutically effective amount of paclitaxel is about 1 μg to 50 mg, about 10 μg to 20 mg, about 25 μg to 10 mg, about 1 μg to 2 mg, about 10 μg to 500 μg, about 100 μg to about 2 mg or about 100 μg to 500 μg. In some instances, the therapeutically effective amount of paclitaxel is about 10 μg, about 25 μg, about 50 μg, about 100 μg, about 500 μg, about 1.0 mg, about 5.0 mg, about 10.0 mg, or about 15.0 mg. In some instances, the therapeutically effective volume of paclitaxel is about 0.01 ml to about 50 ml, about 0.5 ml to about 20 ml, about 0.5 ml to about 25 ml, about 0.5 ml to about 5 ml, or about 1 ml to about 5 ml. In some instances, the therapeutically effective concentration of paclitaxel is about 0.1 mg/mL to about 0.4 mg/mL, about 0.1 mg/mL to about 0.5 mg/mL, or about 0.01 mg/mL to about 2.0 mg/mL. In some instances, the therapeutically effective concentration of paclitaxel is about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, or 3.0 mg/ml. In some instances, the therapeutically effective amount of paclitaxel is about 0.005 mg to 5 mg per cm of longitudinal length of the disease site in the blood vessel, about 0.025 mg to 1 mg per cm of longitudinal length of the disease site in the blood vessel, about 0.05 mg to 2 mg per cm of longitudinal length of the disease site in the blood vessel, or about 0.1 mg to 1 mg per cm of longitudinal length of the disease site in the blood vessel. In some instances, the therapeutically effective amount of paclitaxel is about 0.025 mg to 1 mg per cm of longitudinal length of the blood vessel. The longitudinal length of the disease site in the blood vessel, also known as the longitudinal length of the lesion, is about 1 cm, 5 cm, 10 cm, 20 cm, 30 cm, 40 cm, or 50 cm.

A glucocorticoid administered in combination with temsirolimus comprises a range of dosages that are therapeutically effective for treating the vascular disease. In some instances, the glucocorticoid is dexamethasone. In some instances, the therapeutically effective amount of dexamethasone is about 1 μg to 50 mg, about 10 μg to 20 mg, about 25 μg to 10 mg, about 1 μg to 2 mg, about 10 μg to 500 μg, about 100 μg to 50 mg, about 100 μg to 20 mg, about 100 μg to 10 mg, about 100 μg to 1 mg, or about 100 μg to 500 μg. In some instances, the therapeutically effective amount of dexamethasone is about 10 μg, about 25 μg, about 50 μg, about 100 μg, about 500 μg, about 1.0 mg, about 5.0 mg, about 10.0 mg, about 20.0 mg, about 30.0 mg, about 40.0 mg, or about 50.0 mg. In some instances, the therapeutically effective volume of dexamethasone is about 0.01 mL to about 50 mL, about 0.5 mL to about 20 mL, about 0.5 mL to about 25 mL, about 0.5 mL to about 5 mL, 1 mL to 10 mL, or about 1 mL to about 5 mL. In some instances, the therapeutically effective concentration of dexamethasone is about 0.1 mg/mL to about 0.4 mg/mL, about 0.1 mg/mL to about 0.5 mg/mL, about 0.01 mg/mL to about 2.0 mg/mL, or about 1.0 mg/mL to about 10.0 mg/mL. In some instances, the therapeutically effective concentration of dexamethasone is about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, about 3.0 mg/ml, about 4.0 mg/ml, about 6.0 mg/mL, about 8.0 mg/mL or about 10.0 mg/mL. In some instances, the therapeutically effective amount of dexamethasone is about 0.05 mg to 10 mg per cm of longitudinal length of the disease site in the blood vessel, about 0.05 mg to 7 mg per cm of longitudinal length of the disease site in the blood vessel, about 0.1 mg to 4 mg per cm of longitudinal length of the disease site in the blood vessel, or about 0.1 mg to 2 mg per cm of longitudinal length of the disease site in the blood vessel. In some instances, the therapeutically effective amount of dexamethasone is about 0.8 mg to 8 mg per cm of longitudinal length of the disease site in the blood vessel. In some instances, the therapeutically effective amount of dexamethasone is about 0.1 mg to 2 mg per cm of longitudinal length of the disease site in the blood vessel. The longitudinal length of the disease site in the blood vessel, also known as the longitudinal length of the lesion, is about 1 cm, 5 cm, 10 cm, 20 cm, 30 cm, 40 cm, or 50 cm.

A glucocorticoid administered in combination with paclitaxel comprises a range of dosages that are therapeutically effective for treating the vascular disease. In some instances, the glucocorticoid is dexamethasone. In some instances, the therapeutically effective amount of dexamethasone is about 1 μg to 50 mg, about 10 μg to 20 mg, about 25 μg to 10 mg, about 1 μg to 2 mg, about 10 μg to 500 μg, about 100 μg to 50 mg, about 100 μg to 20 mg, about 100 μg to 10 mg, about 100 μg to 1 mg, or about 100 μg to 500 μg. In some instances, the therapeutically effective amount of dexamethasone is about 10 μg, about 25 μg, about 50 μg, about 100 μg, about 500 μg, about 1.0 mg, about 5.0 mg, about 10.0 mg, about 20.0 mg, about 30.0 mg, about 40.0 mg, or about 50.0 mg. In some instances, the therapeutically effective volume of dexamethasone is about 0.01 mL to about 50 mL, about 0.5 mL to about 20 mL, about 0.5 mL to about 25 mL, about 0.5 mL to about 5 mL, 1 mL to 10 mL, or about 1 mL to about 5 mL. In some instances, the therapeutically effective concentration of dexamethasone is about 0.1 mg/mL to about 0.4 mg/mL, about 0.1 mg/mL to about 0.5 mg/mL, about 0.01 mg/mL to about 2.0 mg/mL, or about 1.0 mg/mL to about 10.0 mg/mL. In some instances, the therapeutically effective concentration of dexamethasone is about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, about 3.0 mg/ml, about 4.0 mg/mL, about 6.0 mg/mL, about 8.0 mg/mL or about 10.0 mg/mL. In some instances, the therapeutically effective amount of dexamethasone is about 0.05 mg to 10 mg per cm of longitudinal length of the disease site in the blood vessel, about 0.05 mg to 7 mg per cm of longitudinal length of the disease site in the blood vessel, about 0.1 mg to 4 mg per cm of longitudinal length of the disease site in the blood vessel, or about 0.1 mg to 2 mg per cm of longitudinal length of the disease site in the blood vessel. In some instances, the therapeutically effective amount of dexamethasone is about 0.8 mg to 8 mg per cm of longitudinal length of the disease site in the blood vessel. In some instances, the therapeutically effective amount of dexamethasone is about 0.1 mg to 2 mg per cm of longitudinal length of the disease site in the blood vessel. The longitudinal length of the disease site in the blood vessel, also known as the longitudinal length of the lesion, is about 1 cm, 5 cm, 10 cm, 20 cm, 30 cm, 40 cm, or 50 cm.

A pharmaceutical composition of temsirolimus administered in combination with a glucocorticoid comprises a range of dosages that are therapeutically effective for treating the vascular disease. In some instances, the therapeutically effective amount of temsirolimus is about 1 µg to 50 mg, about 10 µg to 20 mg, about 25 µg to 10 mg, about 1 µg to 2 mg, about 10 µg to 500 µg, about 100 µg to about 2 mg or about 100 µg to 500 µg. In some instances, the therapeutically effective amount of temsirolimus is about 10 µg, about 25 µg, about 50 µg, about 100 µg, about 500 µg, about 1.0 mg, about 5.0 mg, about 10.0 mg, or about 15.0 mg. In some instances, the therapeutically effective volume of temsirolimus is about 0.01 ml to about 50 ml, about 0.5 ml to about 20 ml, about 0.5 ml to about 25 ml, about 0.5 ml to about 5 ml, or about 1 ml to about 5 ml. In some instances, the therapeutically effective concentration of temsirolimus is about 0.1 mg/mL to about 0.4 mg/mL, about 0.1 mg/mL to about 0.5 mg/mL, or about 0.01 mg/mL to about 2.0 mg/mL. In some instances, the therapeutically effective concentration of temsirolimus is about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, or 3.0 mg/ml. In some instances, the therapeutically effective amount of temsirolimus is about 0.005 mg to 5 mg per cm of longitudinal length of the disease site in the blood vessel, about 0.025 mg to 1 mg per cm of longitudinal length of the disease site in the blood vessel, about 0.05 mg to 2 mg per cm of longitudinal length of the disease site in the blood vessel, or about 0.1 mg to 1 mg per cm of longitudinal length of the disease site in the blood vessel. In some instances, the therapeutically effective amount of temsirolimus is about 0.025 mg to 1 mg per cm of longitudinal length of the blood vessel. The longitudinal length of the disease site in the blood vessel, also known as the longitudinal length of the lesion, is about 1 cm, 5 cm, 10 cm, 20 cm, 30 cm, 40 cm, or 50 cm.

Alternatively, a pharmaceutical composition of paclitaxel administered in combination with a glucocorticoid comprises a range of dosages that are therapeutically effective for treating the vascular disease. In some instances, the therapeutically effective amount of paclitaxel is about 1 µg to 50 mg, about 10 µg to 20 mg, about 25 µg to 10 mg, about 1 µg to 2 mg, about 10 µg to 500 µg, about 100 µg to about 2 mg or about 100 µg to 500 µg. In some instances, the therapeutically effective amount of paclitaxel is about 10 µg, about 25 µg, about 50 µg, about 100 µg, about 500 µg, about 1.0 mg, about 5.0 mg, about 10.0 mg, or about 15.0 mg. In some instances, the therapeutically effective volume of paclitaxel is about 0.01 ml to about 50 ml, about 0.5 ml to about 20 ml, about 0.5 ml to about 25 ml, about 0.5 ml to about 5 ml, or about 1 ml to about 5 ml. In some instances, the therapeutically effective concentration of paclitaxel is about 0.1 mg/mL to about 0.4 mg/mL, about 0.1 mg/mL to about 0.5 mg/mL, or about 0.01 mg/mL to about 2.0 mg/mL. In some instances, the therapeutically effective concentration of paclitaxel is about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, or 3.0 mg/ml. In some instances, the therapeutically effective amount of paclitaxel is about 0.005 mg to 5 mg per cm of longitudinal length of the disease site in the blood vessel, about 0.025 mg to 1 mg per cm of longitudinal length of the disease site in the blood vessel, about 0.05 mg to 2 mg per cm of longitudinal length of the disease site in the blood vessel, or about 0.1 mg to 1 mg per cm of longitudinal length of the disease site in the blood vessel. In some instances, the therapeutically effective amount of paclitaxel is about 0.025 mg to 1 mg per cm of longitudinal length of the blood vessel. The longitudinal length of the disease site in the blood vessel, also known as the longitudinal length of the lesion, is about 1 cm, 5 cm, 10 cm, 20 cm, 30 cm, 40 cm, or 50 cm.

A pharmaceutical composition of a glucocorticoid administered in combination with temsirolimus comprises a range of dosages that are therapeutically effective for treating the vascular disease. In some instances, the glucocorticoid is dexamethasone. In some instances, the therapeutically effective amount of dexamethasone is about 1 µg to 50 mg, about 10 µg to 20 mg, about 25 µg to 10 mg, about 1 µg to 2 mg, about 10 µg to 500 µg, about 100 µg to 50 mg, about 100 µg to 20 mg, about 100 µg to 10 mg, about 100 µg to 1 mg, or about 100 µg to 500 µg. In some instances, the therapeutically effective amount of dexamethasone is about 10 µg, about 25 µg, about 50 µg, about 100 µg, about 500 µg, about 1.0 mg, about 5.0 mg, about 10.0 mg, about 20.0 mg, about 30.0 mg, about 40.0 mg, or about 50.0 mg. In some instances, the therapeutically effective volume of dexamethasone is about 0.01 mL to about 50 mL, about 0.5 mL to about 20 mL, about 0.5 mL to about 25 mL, about 0.5 mL to about 5 mL, 1 mL to 10 mL, or about 1 mL to about 5 mL. In some instances, the therapeutically effective concentration of dexamethasone is about 0.1 mg/mL to about 0.4 mg/mL, about 0.1 mg/mL to about 0.5 mg/mL, about 0.01 mg/mL to about 2.0 mg/mL, or about 1.0 mg/mL to about 10.0 mg/mL. In some instances, the therapeutically effective concentration of dexamethasone is about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, about 3.0 mg/ml, about 4.0 mg/mL, about 6.0 mg/mL, about 8.0 mg/mL or about 10.0 mg/mL. In some instances, the therapeutically effective amount of dexamethasone is about 0.05 mg to 10 mg per cm of longitudinal length of the disease site in the blood vessel, about 0.05 mg to 7 mg per cm of longitudinal length of the disease site in the blood vessel, about 0.1 mg to 4 mg per cm of longitudinal length of the disease site in the blood vessel, or about 0.1 mg to 2 mg per cm of longitudinal length of the disease site in the blood vessel. In some instances, the therapeutically effective amount of dexamethasone is about 0.1 mg to 2 mg per cm of longitudinal length of the disease site in the blood vessel. The longitudinal length of the disease site in the blood vessel, also known as the longitudinal length of the lesion, is about 1 cm, 5 cm, 10 cm, 20 cm, 30 cm, 40 cm, or 50 cm.

The dose of the composition comprising temsirolimus and a glucocorticoid as described herein differ, depending upon the patient's condition, that is, stage of the disease, general health status, age, and other factors.

The dose of the composition comprising paclitaxel and a glucocorticoid as described herein differ, depending upon the patient's condition, that is, stage of the disease, general health status, age, and other factors.

Pharmaceutical compositions described herein are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

In one embodiment, the pharmaceutical compositions of temsirolimus and a glucocorticoid described herein, or pharmaceutically acceptable salts thereof, are used in the preparation of medicaments for the treatment of diseases or conditions in a mammal that would benefit from administration of any one of the compounds disclosed. In one embodiment, the pharmaceutical compositions of paclitaxel and a glucocorticoid described herein, or pharmaceutically acceptable salts thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the pharmaceutical compositions of temsirolimus and a glucocorticoid described herein are administered for prophylactic and/or therapeutic treatments. In certain embodiments, the pharmaceutical compositions of paclitaxel and a glucocorticoid described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, the pharmaceutical composition of temsirolimus and a glucocorticoid described herein are administered to a patient susceptible to or otherwise at risk of a particular disease, disorder or condition. In prophylactic applications, the pharmaceutical composition of paclitaxel and a glucocorticoid described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, in which the mammal previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of a pharmaceutical composition of temsirolimus and a glucocorticoid are administered chronically, that is, for an extended period of time, including throughout the duration of the patient's life in order to ameliorate or otherwise control or limit the symptoms of the patient's disease or condition. In certain embodiments wherein the patient's condition does not improve, upon the doctor's discretion the administration of a pharmaceutical composition of paclitaxel and a glucocorticoid are administered chronically, that is, for an extended period of time, including throughout the duration of the patient's life in order to ameliorate or otherwise control or limit the symptoms of the patient's disease or condition.

Once improvement of the patient's conditions has occurred, a maintenance injection is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the dosage amount of the compounds described herein lies within a range of circulating concentrations that include the ED50 with minimal toxicity. In certain embodiments, the dosage range and/or the unit dosage amount varies within this range depending upon the dosage form employed and the route of administration utilized.

In any of the aforementioned aspects are further embodiments comprising single administrations of the effective amount of the pharmaceutical composition of temsirolimus and a glucocorticoid described herein, including further embodiments in which the composition is administered once a month, twice a month, 3 times a month, once every 2 months, once every 3 months, once every 4 months, once every 5 months, or once every 6 months.

In any of the aforementioned aspects are further embodiments comprising single administrations of the effective amount of the pharmaceutical composition of paclitaxel and a glucocorticoid described herein, including further embodiments in which the composition is administered once a month, twice a month, 3 times a month, once every 2 months, once every 3 months, once every 4 months, once every 5 months, or once every 6 months.

In certain embodiments wherein a patient's status does improve, the dose of drug being administered is temporarily reduced or temporarily suspended for a certain length of time (e.g., a "drug holiday"). In specific embodiments, the length of the drug holiday is between 1 month and 5 years, including by way of example only, 2 months, 3 months, 4 months, 5 months, 6 months, 7 months, 1 year, 2 years, 3 years, 4 years, 5 years, or more than 5 years. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 6 months to 2 years. In one embodiment, the length of the drug holiday is 1 year. In one embodiment, the length of the drug holiday is 2 years. In one embodiment, the length of the drug holiday is 3 years.

Devices for Administration

Described herein are devices and methods for administration of pharmaceutical compositions. As an alternative to stent-based luminal drug delivery, the direct delivery of drug into vascular and other luminal walls in some instances enhances the therapeutic concentrations of pharmaceutical agents in targeted tissues. For example, it is in some cases particularly desirable to provide for an extended volumetric distribution of the delivered pharmaceutical agent including both longitudinal and radial spreading from the injection site(s) in order to provide therapeutic dosage levels of the agent within the targeted tissue region. In some instances, devices efficiently deliver the drugs into the targeted tissue and limit or avoid the loss of drugs into the luminal blood flow. In some instances, the persistence of such therapeutic concentrations of the pharmaceutical agent in the tissue were also increased, particularly in targeted tissues away from the blood vessel wall, including the adventitial tissue surrounding the blood vessel wall. In some instances, the uniformity and extent of pharmaceutical agent delivery over remote, extended, and distributed regions of the adventitia and other tissues surrounding the blood vessels is increased. In some instances, pharmaceutical agents are delivered through the blood vessel walls at non-diseased sites within the blood vessel, where the agent then migrate through the adventitia or other tissues to the diseased site(s). In some instances, intravascular delivery of pharmaceutical agents treats diseases and conditions of the tissues and organs in addition to those directly related to the vasculature.

In some cases, drug injection or infusion catheters and devices are suitable for use with the methods described herein to inject pharmaceutical compositions into blood vessels the treat restenosis. An example of a device includes the Mercator Bullfrog® Micro-Infusion Device available from Mercator MedSystems of Emeryville, Calif. Other examples include the devices described in U.S. patent application Ser. Nos. 14/605,865 and 15/691,138, the entire disclosures of which are incorporated herein by reference. Examples of suitable devices and their use are described as follows. In some instances, injections are performed using needles or microneedles.

Figure 1B:
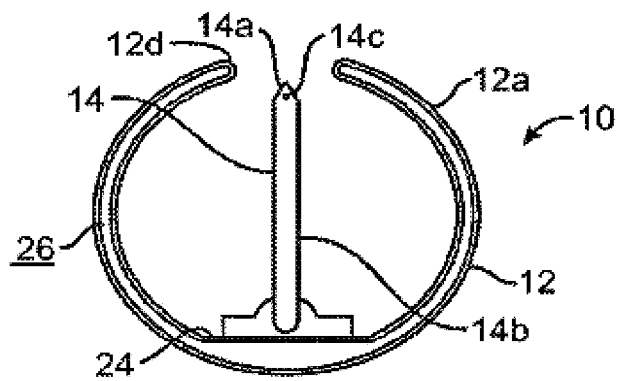
FIG. 1B is a cross-sectional view along line 1B-1B of FIG. 1A.
Figure 1C:
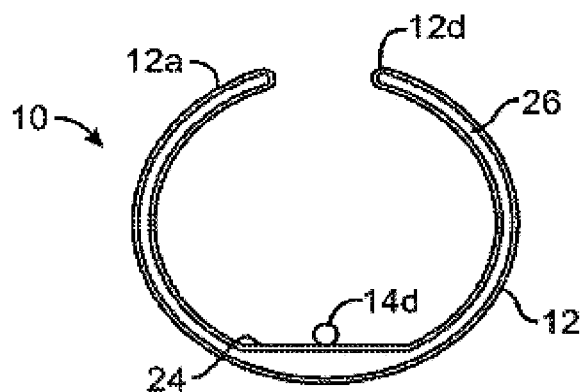
FIG. 1C is a cross-sectional view along line 1C-1C of FIG. 1A.
Figure 2A:
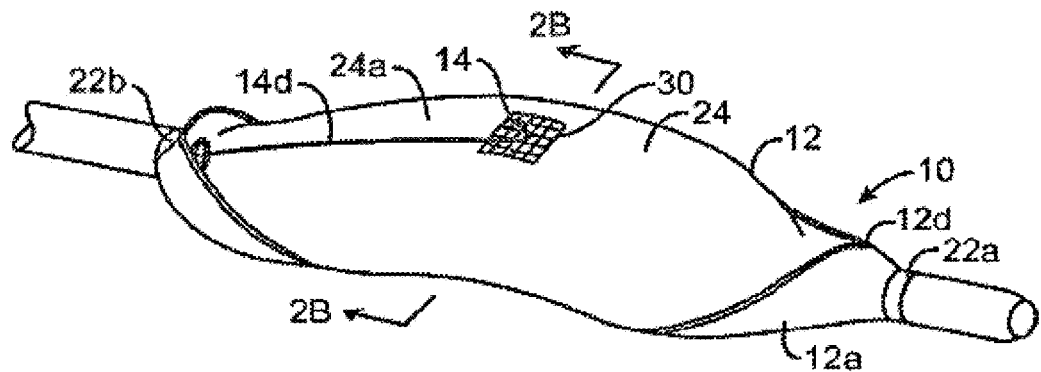
FIG. 2A is a schematic, perspective view of the catheter of FIGS. 1A-1C shown with the injection needle deployed.
Figure 2B:
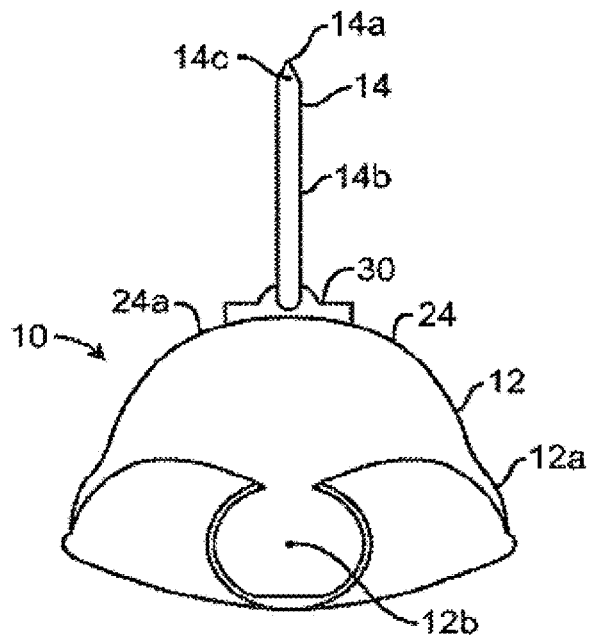
FIG. 2B is a cross-sectional view along line 2B-2B of FIG. 2A.

In some cases, a pharmaceutical composition to treat the vascular disease is delivered to the tissue surrounding a blood vessel using a drug injection or infusion catheter. In one example of a drug injection or infusion catheter as shown in FIGS. 1A-2B, a microfabricated intraluminal catheter 10 includes an actuator 12 having an actuator body 12a and central longitudinal axis 12b. The actuator body more or less forms a C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B). In some instances, the actuator is capped at its proximal end 12e and distal end 12f by a lead end 16 and a tip end 18, respectively, of a therapeutic catheter 20. The catheter tip end serves as a means of locating the actuator inside a body lumen by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (µm), substantially flexible but relatively non-distensible material, such as Parylene (types C, D or N), or a metal, for example, aluminum, stainless steel, gold, titanium or tungsten. The retaining rings form a flexible but relatively non-distensible substantially "C"-shaped structure at each end of the actuator. In some cases the catheter is joined to the retaining rings by, for example, a butt-weld, an ultra-sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-flexible but relatively non-distensible or flexible but relatively non-distensible, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 200 psi upon application of the activating fluid to the open area 26. The material from which the central section is made of is flexible but relatively non-distensible or semi-flexible but relatively non-distensible in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube often is constructed of Teflon® or other inert plastics. The activating fluid often is a saline solution or a radio-opaque dye.

In some instances, the microneedle 14 is located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle often is joined to the surface 24a by a metallic or polymer mesh-like structure 30 (See FIG. 4), which is itself affixed to the surface 24a by an adhesive. The mesh-like structure often is-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it often is configured like a neural probe to accomplish other tasks.

As shown, the microneedle extends approximately perpendicularly from surface 24a. Thus, as described, the microneedle will move substantially perpendicularly to an axis of a lumen into which has been inserted, to allow direct puncture or breach of body lumen walls.

The microneedle further includes a pharmaceutical or drug supply conduit, tube or fluid pathway 14d which places the microneedle in fluid communication with the appropriate fluid interconnect at the catheter lead end. This supply tube often is formed integrally with the shaft 14b, or it often is formed as a separate piece that is later joined to the shaft by, for example, an adhesive such as an epoxy.

In some instances, the needle 14 is a 30-gauge, or smaller, steel needle. Alternatively, the microneedle is microfabricated from polymers, other metals, metal alloys or semiconductor materials. The needle, for example, is made of Parylene, silicon or glass. Microneedles and methods of fabrication are described in U.S. application Ser. No. 09/877,653, filed Jun. 8, 2001, entitled "Microfabricated Surgical Device", assigned to the assignee of the subject application, the entire disclosure of which is incorporated herein by reference.

Figure 3:
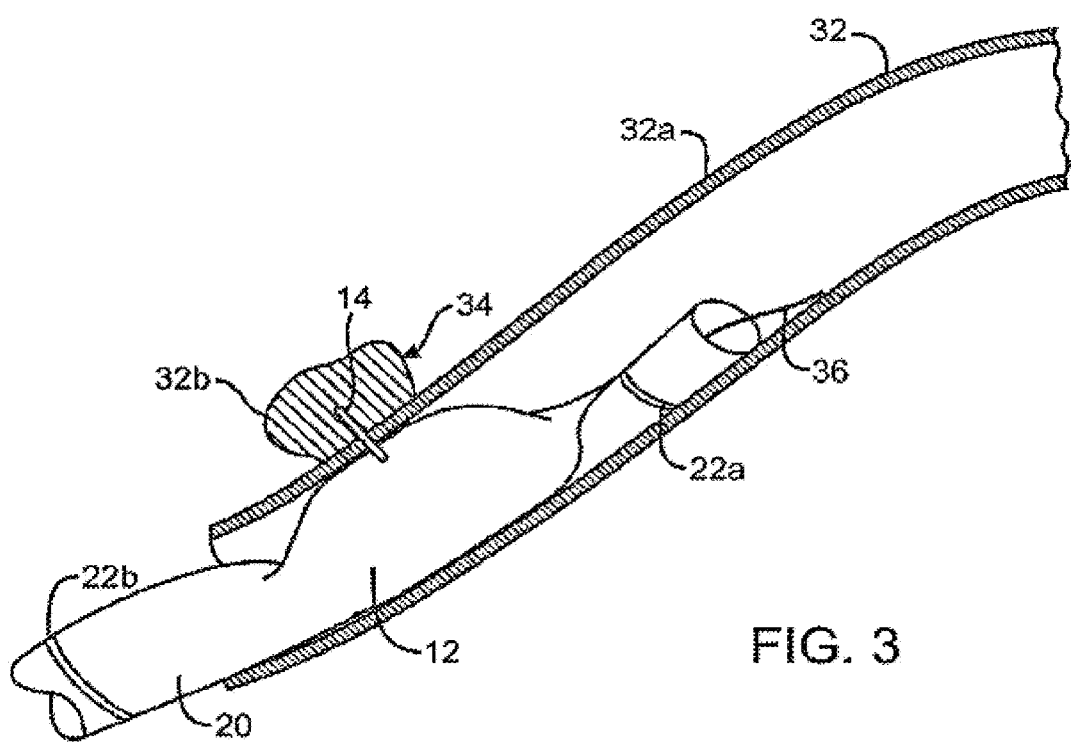
FIG. 3 is a schematic, perspective view of the intraluminal catheter of FIGS. 1A-1C injecting therapeutic agents into an adventitial space surrounding a body lumen in accordance with the methods of the present disclosure.

The catheter 20, in use, is inserted through an opening in the body (e.g. for bronchial or sinus treatment) or through a percutaneous puncture site (e.g. for artery or venous treatment) and moved within a patient's body passageways 32, until a specific, targeted region 34 is reached (see FIG. 3). The targeted region 34 is the site of tissue damage or more usually will be adjacent the sites typically being within 100 mm or less to allow migration of the therapeutic or diagnostic agent. As is well known in catheter-based interventional procedures, the catheter 20 follows a guide wire 36 that has previously been inserted into the patient. Optionally, the catheter 20 also follows the path of a previously-inserted guide catheter (not shown) that encompasses the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains unfurled or held inside the actuator body so that no trauma is caused to the body lumen walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a body lumen wall 32a. In some instances, it takes only between approximately 100 milliseconds and five seconds for the microneedle to move from its furled state to its unfurled state.

The ends of the actuator at the retaining rings 22a and 22b remain fixed to the catheter 20. Thus, they do not deform during actuation. Since the actuator begins as a furled structure, its so-called pregnant shape exists as an unstable buckling mode. This instability, upon actuation, in some cases produces a large-scale motion of the microneedle approximately perpendicular to the central axis of the actuator body, causing a rapid puncture of the body lumen wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle aperture, in fact, travels with such force that it can enter body lumen tissue 32b as well as the adventitia, media, or intima surrounding body lumens. Additionally, since the actuator is "parked" or stopped prior to actuation, more precise placement and control over penetration of the body lumen wall are obtained.

After actuation of the microneedle and delivery of the agents to the target region via the microneedle, the activating fluid is exhausted from the open area 26 of the actuator, causing the expandable section 24 to return to its original, furled state. This also causes the microneedle to be withdrawn from the body lumen wall. The microneedle, being withdrawn, is once again sheathed by the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the pharmaceutical being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and pharmaceuticals or biological agents with reliability.

By way of example, the microneedle has have an overall length of between about 200 and 3,000 microns (μm). The interior cross-sectional dimension of the shaft 14b and supply tube 14d often is on the order of 20 to 250 um, while the tube's and shaft's exterior cross-sectional dimension often is between about 100 and 500 μm. The overall length of the actuator body often is between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls has in some instances a length of about 4-40 mm, and a cross-sectional dimension of about 50-500 μm. The diameter of the delivery tube for the activating fluid often is about 100 μm. The catheter size often is between 1.5 and 15 French (Fr).

Variations of the present disclosure include a multiple-buckling actuator with a single supply tube for the activating fluid. The multiple-buckling actuator includes multiple needles that can be inserted into or through a lumen wall for providing injection at different locations or times.

Figure 4:
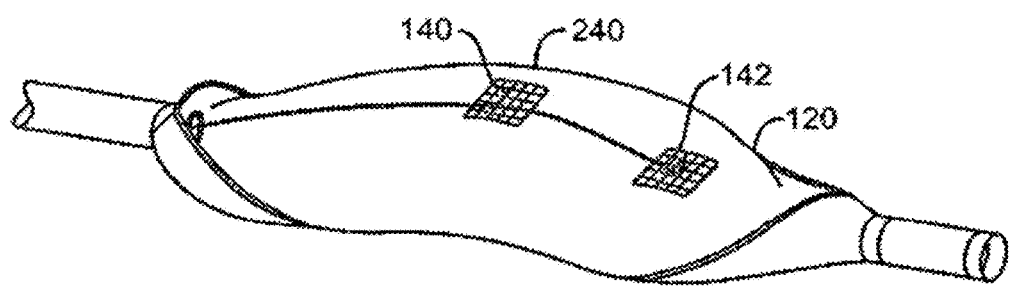
FIG. 4 is a schematic, perspective view of another embodiment of an intraluminal injection catheter useful in the methods of the present disclosure.

For instance, as shown in FIG. 4, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid is selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time $t_1$, and pressure $p_1$, and the microneedle 142 moving at time $t_2$ and $p_2$, with $t_1$, and $p_1$, being less than $t_2$ and $p_2$, respectively.

This sort of staged buckling can also be provided with different pneumatic or hydraulic connections at different parts of the central section 240 in which each part includes an individual microneedle.

Figure 5:
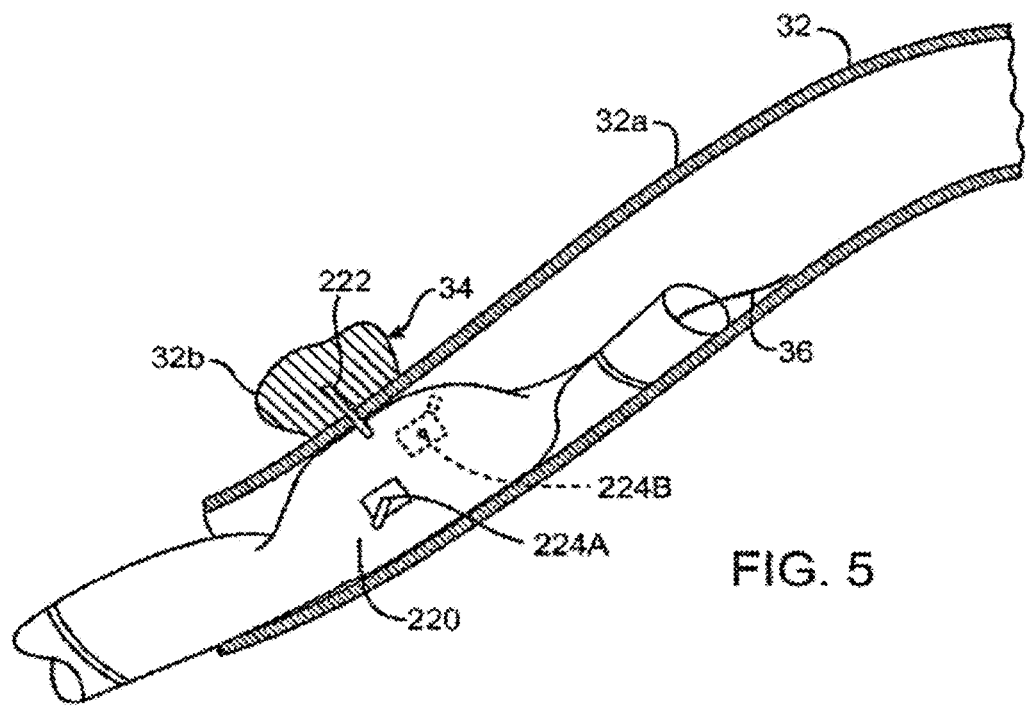
FIG. 5 is a schematic, perspective view of still another embodiment of an intraluminal injection catheter useful in the methods of the present disclosure, as inserted into one of a patient's body lumens.

Also, as shown in FIG. 5, an actuator 220 could be constructed such that its needles 222 and 224A move in different directions. As shown, upon actuation, the needles move at angle of approximately 90° to each other to puncture different parts of a lumen wall. A needle 224B (as shown in phantom) could alternatively be arranged to move at angle of about 180° to the needle 224A.

Figure 6:
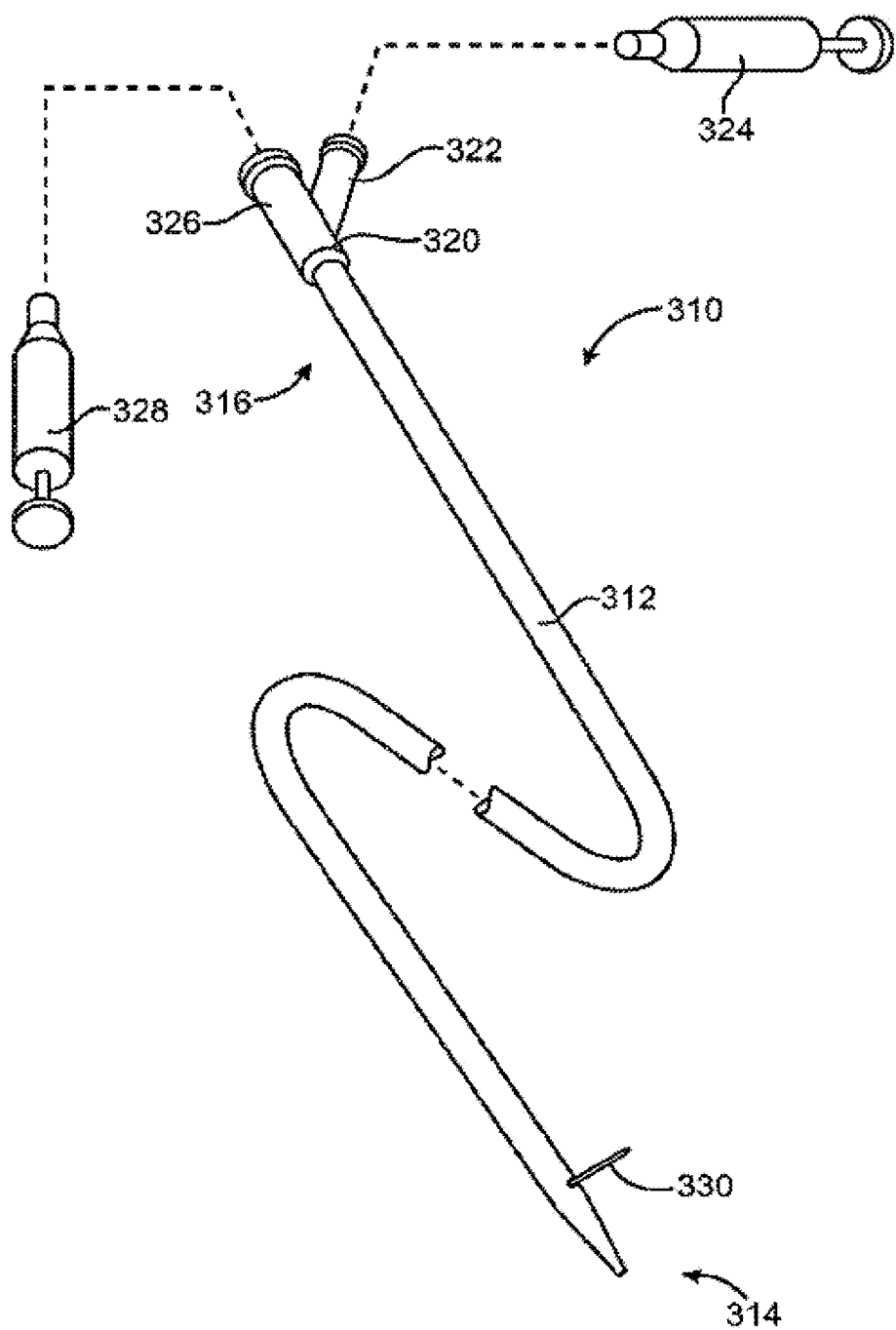
FIG. 6 is a perspective view of a needle injection catheter useful in the methods and systems of the present disclosure.

Referring now to FIG. 6, a needle injection catheter 310 constructed in accordance with the principles of the present disclosure comprises a catheter body 312 having a distal end 314 and a proximal 316. Usually, a guide wire lumen 313 will be provided in a distal nose 352 of the catheter, although over-the-wire and embodiments which do not require guide wire placement will also be within the scope of the present disclosure. A two-port hub 320 is attached to the proximal end 316 of the catheter body 312 and includes a first port 322 for delivery of a hydraulic fluid, e.g., using a syringe 324, and a second port 326 for delivering the pharmaceutical agent, e.g., using a syringe 328. A reciprocatable, deflectable needle 330 is mounted near the distal end of the catheter body 312 and is shown in its laterally advanced configuration in FIG. 6.

Figure 7:
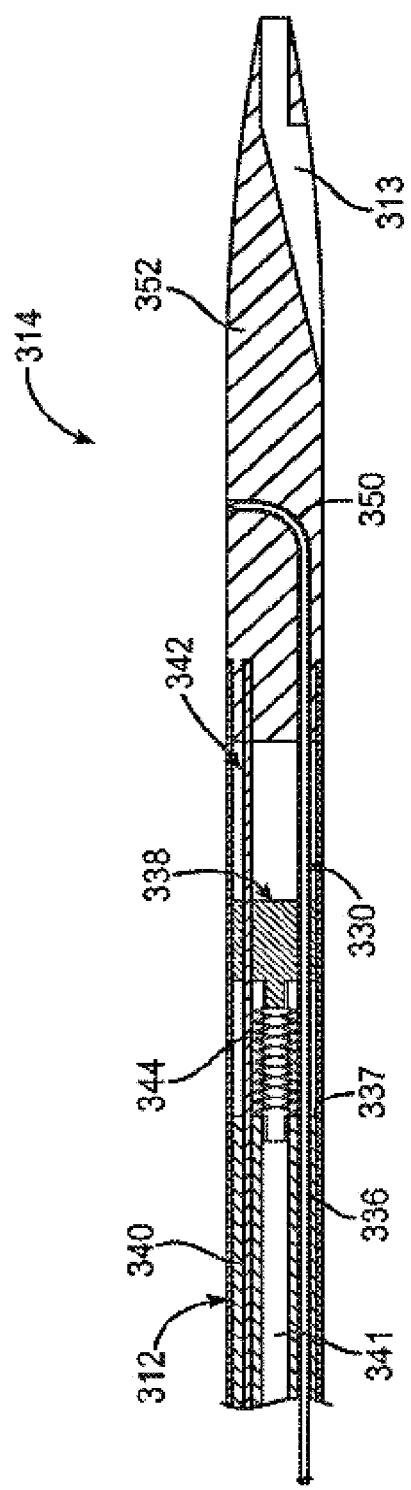
FIG. 7 is a cross-sectional view of the catheter FIG. 6 shown with the injection needle in a retracted configuration.

Referring now to FIG. 7, the proximal end 314 of the catheter body 312 has a main lumen 336 which holds the needle 330, a reciprocatable piston 338, and a hydraulic fluid delivery tube 340. The piston 338 is mounted to slide over a rail 342 and is fixedly attached to the needle 330. Thus, by delivering a pressurized hydraulic fluid through a lumen 341 tube 340 into a bellows structure 344, the piston 338 often is advanced axially toward the distal tip in order to cause the needle to pass through a deflection path 350 formed in a catheter nose 352.

Figure 8:
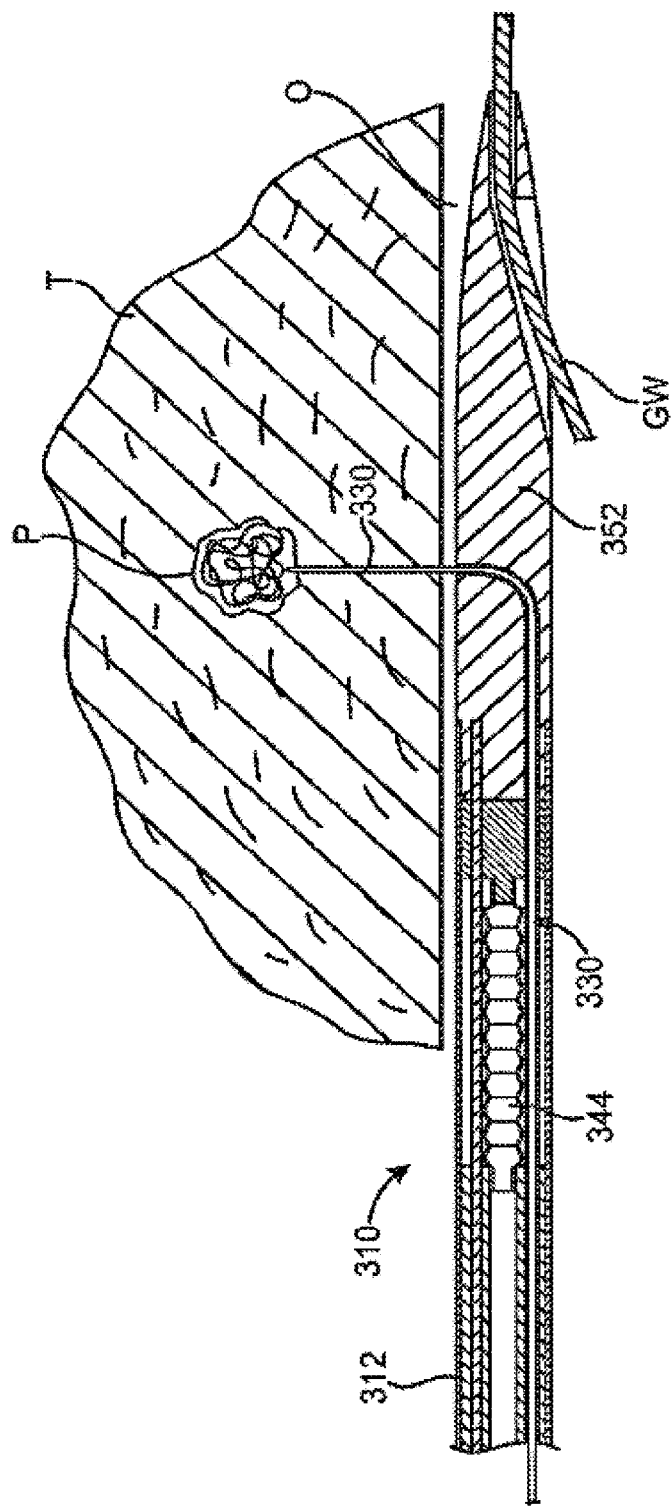
FIG. 8 is a cross-sectional view similar to FIG. 7, shown with the injection needle laterally advanced into luminal tissue for the delivery of therapeutic or diagnostic agents according to the present disclosure.

As can be seen in FIG. 8, the catheter 310 often is positioned in a coronary blood vessel BV, over a guide wire GW in a conventional manner. Distal advancement of the piston 338 causes the needle 330 to advance into luminal tissue T adjacent to the catheter when it is present in the blood vessel. The therapeutic or diagnostic agents often are introduced through the port 326 using syringe 328 in order to introduce a plume P of agent in the cardiac tissue, as illustrated in FIG. 8. The plume P will be within or adjacent to the region of tissue damage as described above.

The needle 330 in some cases extends the entire length of the catheter body 312 or, more usually, will extend only partially into the therapeutic or diagnostic agents delivery lumen 337 in the tube 340. A proximal end of the needle can form a sliding seal with the lumen 337 to permit pressurized delivery of the agent through the needle.

The needle 330 will be composed of an elastic material, typically an elastic or super elastic metal, typically being nitinol or other super elastic metal. Alternatively, the needle 330 could be formed from a non-elastically deformable or malleable metal which is shaped as it passes through a deflection path. The use of non-elastically deformable metals, however, is less preferred since such metals will generally not retain their straightened configuration after they pass through the deflection path.

In some cases, the bellows structure 344 is made by depositing parylene or another conformal polymer layer onto a mandrel and then dissolving the mandrel from within the polymer shell structure. Alternatively, the bellows 344 could be made from an elastomeric material to form a balloon structure. In a still further alternative, a spring structure can be utilized in, on, or over the bellows in order to drive the bellows to a closed position in the absence of pressurized hydraulic fluid therein.

After the therapeutic material is delivered through the needle 330, as shown in FIG. 8, the needle is retracted and the catheter either repositioned for further agent delivery or withdrawn. In some embodiments, the needle will be retracted simply by aspirating the hydraulic fluid from the bellows 344. In other embodiments, needle retraction is assisted by a return spring, e.g., locked between a distal face of the piston 338 and a proximal wall of the distal tip 352 (not shown) and/or by a pull wire attached to the piston and running through lumen 341.

Figure 9A:
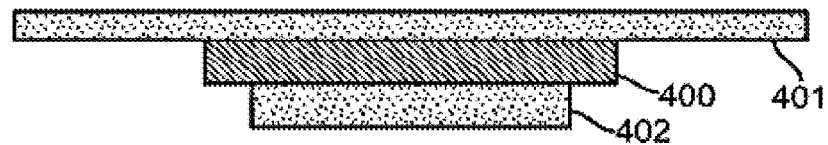
FIG. 9A is a cross-sectional view of a step in an exemplary fabrication process employed to create a free-standing low-modulus patch within a higher modulus anchor, framework or substrate.

FIGS. 9A-9E illustrate an exemplary process for fabricating a dual modulus balloon structure or anchored membrane structure in accordance with the principles of the present disclosure. The first step of the fabrication process is seen in FIG. 9A, in which a low modulus "patch", or membrane, material 400 is layered between removable (e.g. dissolvable) substrates 401 and 402. The substrate 401 covers one entire face of the patch 400, while the substrate 402 covers only a portion of the opposite face, leaving an exposed edge or border region about the periphery.

Figure 9B:
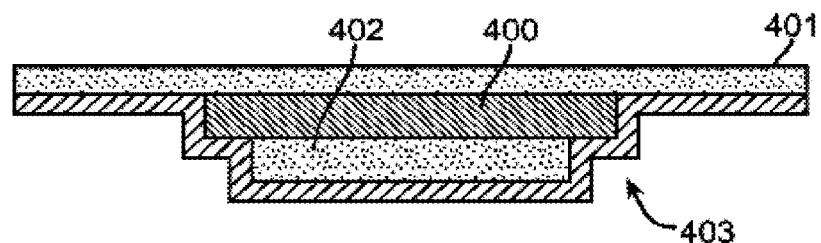
FIG. 9B is a cross-sectional view of a step in an exemplary fabrication process employed to create a free-standing low-modulus patch within a higher modulus anchor, framework or substrate.

In FIG. 9B, a layer of a "flexible but relatively non-distensible" material 403 is deposited onto one side of the sandwich structure from FIG. 9A to provide a frame to which the low-modulus patch is attached. This material is, for example, parylene N, C, or D, though it can be one of many other polymers or metals. When the flexible but relatively non-distensible material is parylene and the patch material is a silicone or siloxane polymer, a chemomechanical bond is formed between the layers, creating a strong and leak-free joint between the two materials. The joint formed between the two materials usually has a peel strength or interfacial strength of at least 0.05 N/mm$^2$, typically at least 0.1 N/mm$^2$, and often at least 0.2 N/mm$^2$.

Figure 9C:
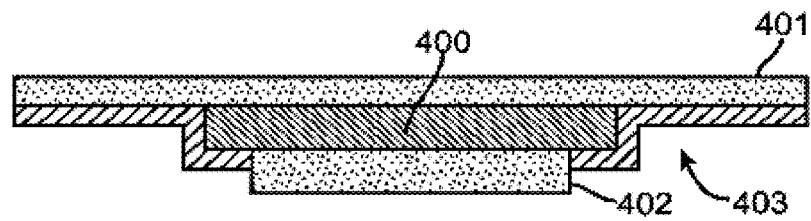
FIG. 9C is a cross-sectional view of a step in an exemplary fabrication process employed to create a free-standing low-modulus patch within a higher modulus anchor, framework or substrate.
Figure 9D:
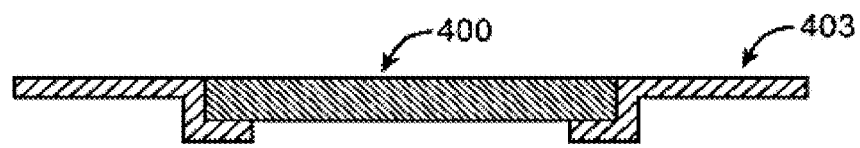
FIG. 9D is a cross-sectional view of a step in an exemplary fabrication process employed to create a free-standing low-modulus patch within a higher modulus anchor, framework or substrate.

In FIG. 9C, the "flexible but relatively non-distensible" frame or anchor material 403 has been trimmed or etched to expose the substrate material 402 so that it can be removed. Materials 401 and 402 is dissolvable polymers that can be removed by one of many chemical solvents. In FIG. 9D, the materials 401 and 402 have been removed by dissolution, leaving materials 400 and 403 joined edge-to-edge to form the low modulus, or elastomeric, patch 400 within a frame of generally flexible but relatively non-distensible material 403.

Figure 9E:
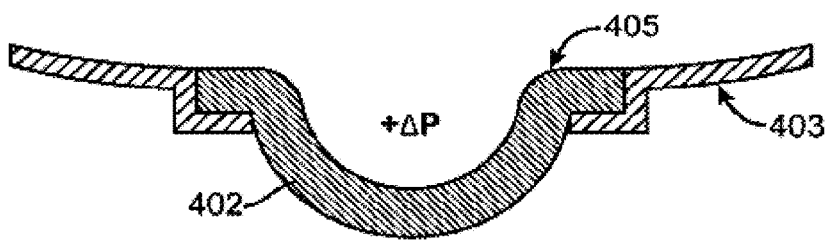
FIG. 9E is a cross-sectional view of a step in an exemplary fabrication process employed to create a free-standing low-modulus patch within a higher modulus anchor, framework or substrate.

As shown in FIG. 9E, when positive pressure+ΔP is applied to one side 405 of the structure, the non-distensible frame 403 deforms only slightly, while the elastomeric patch 400 deforms much more. The low modulus material in some instances has a material modulus which is always lower than that of the high modulus material and is typically in the range from 0.1 to 1,000 MPa, more typically in the range from 1 to 250 MPa. The high modulus material in some instances has a material modulus in the range from 1 to 50,000 MPa, more typically in the range from 10 to 10,000 MPa. The material thicknesses often ranges in both cases from approximately 1 micron to several millimeters, depending on the ultimate size of the intended product. For the treatment of most body lumens, the thicknesses of both material layers 402 and 403 are in the range from 10 microns to 2 mm.

Referring to FIGS. 10A-10D, the elastomeric patch of FIGS. 9A-9D is integrated into the intraluminal catheter of FIG. 1-5. In FIG. 10A-D, the progressive pressurization of such a structure is displayed in order of increasing pressure. In FIG. 10A, the balloon is placed within a body lumen L. The lumen wall W divides the lumen from periluminal tissue T, or adventitia A*, depending on the anatomy of the particular lumen. The pressure is neutral, and the non-distensible structure forms a U-shaped involuted balloon 12 similar to that in FIG. 1 in which a needle 14 is sheathed. While a needle is displayed in this diagram, other working elements including cutting blades, laser or fiber optic tips, radiofrequency transmitters, or other structures could be substituted for the needle. For all such structures, however, the elastomeric patch 400 will usually be disposed on the opposite side of the involuted balloon 12 from the needle 14.

Actuation of the balloon 12 occurs with positive pressurization. In FIG. 10B, pressure (+$\Delta P_1$) is added, which begins to deform the flexible but relatively non-distensible structure, causing the balloon involution to begin its reversal toward the lower energy state of a round pressure vessel. At higher pressure+$\Delta P_2$ in FIG. 10C, the flexible but relatively non-distensible balloon material has reached its rounded shape and the elastomeric patch has begun to stretch. Finally, in FIG. 10D at still higher pressure+$\Delta P_3$, the elastomeric patch has stretched out to accommodate the full lumen diameter, providing an opposing force to the needle tip and sliding the needle through the lumen wall and into the adventitia. Typical dimensions for the body lumens contemplated in this figure are between 0.1 mm and 50 mm, more often between 0.5 mm and 20 mm, and most often between 1 mm and 10 mm. The thickness of the tissue between the lumen and adventitia is typically between 0.001 mm and 5 mm, more often between 0.01 mm and 2 mm and most often between 0.05 mm and 1 mm. The pressure+$\Delta P$ useful to cause actuation of the balloon is typically in the range from 0.1 atmospheres to 20 atmospheres, more typically in the range from 0.5 to 20 atmospheres, and often in the range from 1 to 10 atmospheres.

As illustrated in FIGS. 11A-11C, the dual modulus structure formed herein provides for low-pressure (i.e., below pressures that may damage body tissues) actuation of an intraluminal medical device to place working elements such as needles in contact with or through lumen walls. By inflation of a constant pressure, and the elastomeric material will conform to the lumen diameter to provide full apposition. Dual modulus balloon 12 is inflated to a pressure +$\Delta P_3$ in three different lumen diameters in FIGS. 11A, 11B, and 11C. for the progressively larger inflation of patch 400 provides optimal apposition of the needle through the vessel wall regardless of diameter. Thus, a variable diameter system is created in which the same catheter often is employed in lumens throughout the body that are within a range of diameters. This is useful because most medical products are limited to very tight constraints (typically within 0.5 mm) in which lumens may be used. A system as described in this disclosure in some cases accommodates several millimeters of variability in the luminal diameters for which they are useful.

Figure 12A:
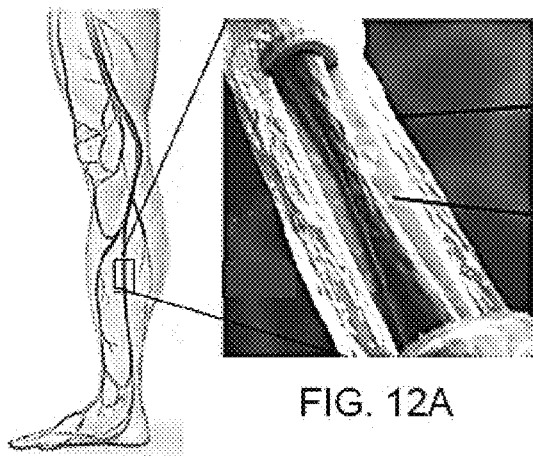
FIG. 12A shows a schematic view of a step in treating a blood vessel affected by atherosclerosis with delivery of a pharmaceutical composition by injection by a needle through a catheter.
Figure 12B:
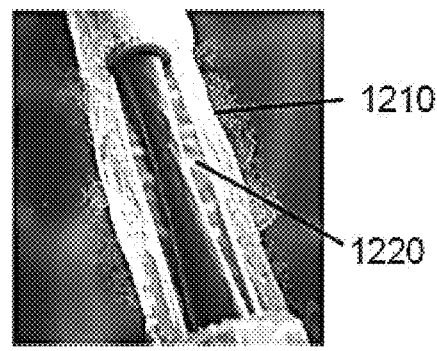
FIG. 12B shows schematic views of a step in treating a blood vessel affected by atherosclerosis with delivery of a pharmaceutical composition by injection by a needle through a catheter.
Figure 12C:
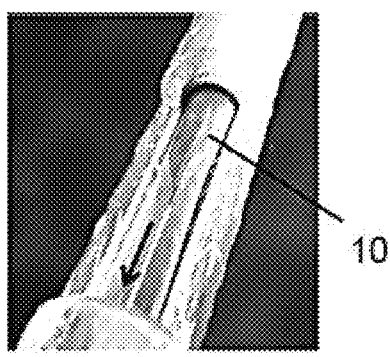
FIG. 12C shows schematic views of a step in treating a blood vessel affected by atherosclerosis with delivery of a pharmaceutical composition by injection by a needle through a catheter.
Figure 12D:
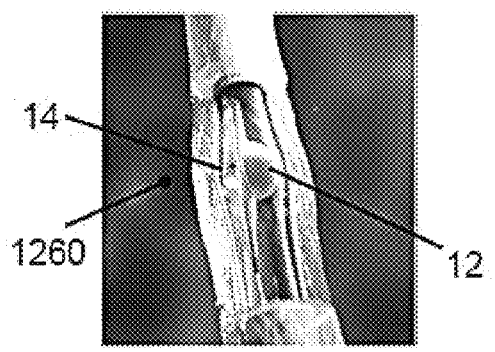
FIG. 12D shows schematic views of a step in treating a blood vessel affected by atherosclerosis with delivery of a pharmaceutical composition by injection by a needle through a catheter.
Figure 12E:
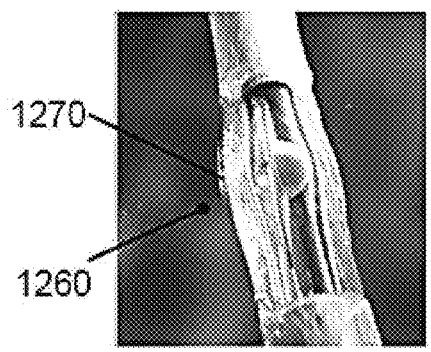
FIG. 12E shows schematic views of a step in treating a blood vessel affected by atherosclerosis with delivery of a pharmaceutical composition by injection by a needle through a catheter.
Figure 12F:
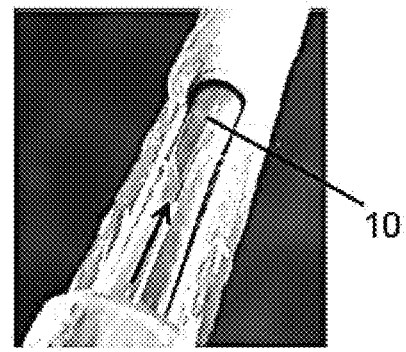
FIG. 12F shows schematic views of treating a blood vessel affected by atherosclerosis with delivery of a pharmaceutical composition by a step in injection by a needle through a catheter.

FIGS. 12A-12F show schematics of an exemplary treating of vascular disease in a subject. FIG. 12A shows a blood vessel 1210 in the lower limb that is affected by atherosclerosis or a plaque 1220 of lumen of the blood vessel. FIG. 12B shows the affected blood vessel 1210 after a revascularization procedure such as angioplasty or atherectomy to increase the lumen diameter of the blood vessel. The target region of the tissue surrounding the affected blood vessel in some cases has had a revascularization procedure previously. FIG. 12C shows the delivery of the treatment catheter 10 into the target region through the vasculature of the subject. FIG. 12D shows the expansion of the expandable element 12 of the treatment catheter to puncture into the target tissue 1260 surrounding the blood vessel with the needle 14 of the treatment catheter. The expandable element 12 often is also known as an actuator. FIG. 12E shows the delivery of the pharmaceutical composition comprising temsirolimus, dexamethasone, paclitaxel, or a combination thereof 1270 into the target tissue surrounding the blood vessel 1260. FIG. 12F shows the withdrawal of the treatment catheter 10 after the collapse of the expandable element 12 and withdrawal of the needle 14 from the target tissue 1260 surrounding the blood vessel.

Figure 13:
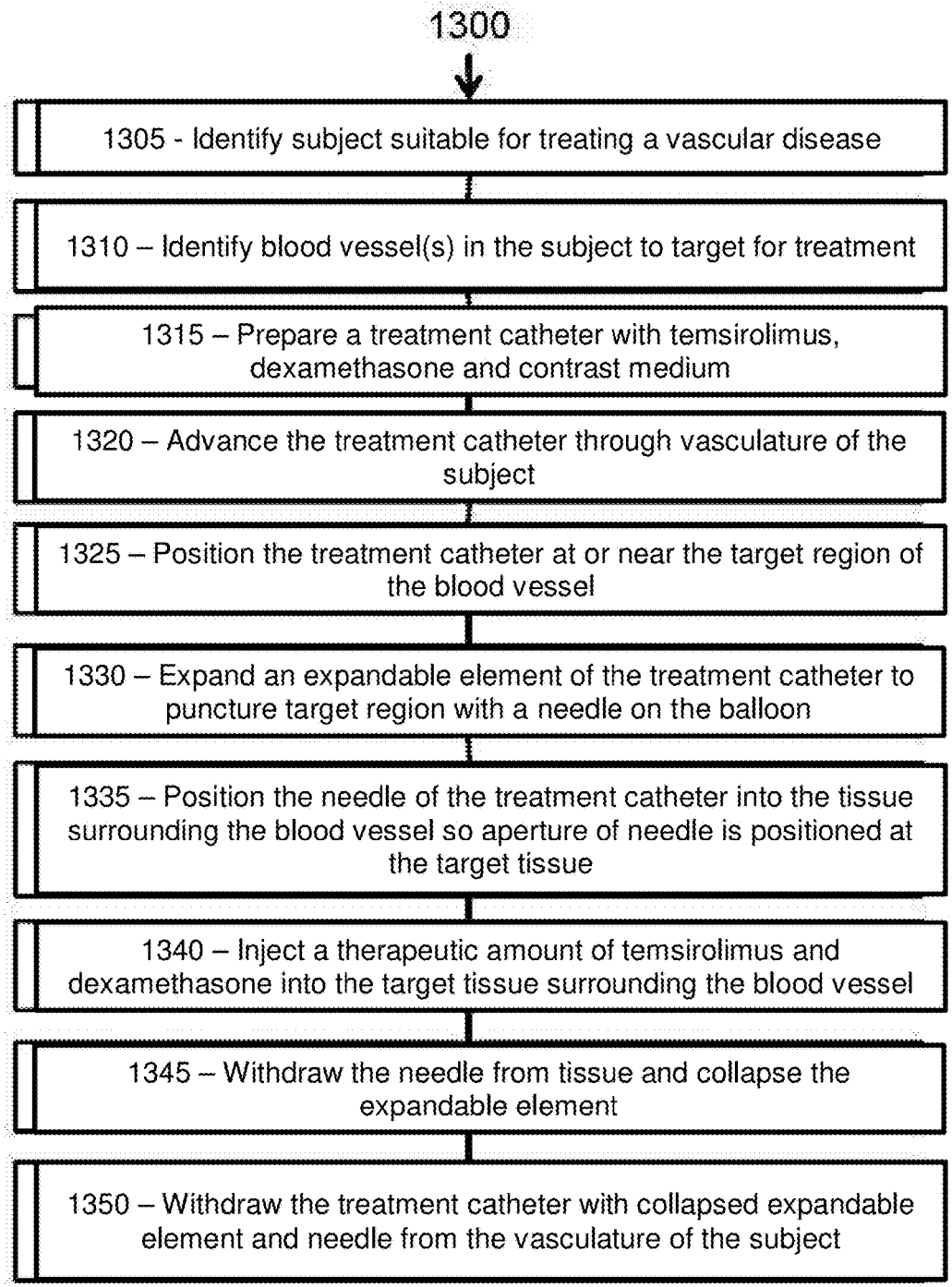
FIG. 13 shows a flow chart of a method of treating vascular disease in a subject.

FIG. 13 shows a flow chart of a method 1300 of treating vascular disease in a subject. In a step 1305, a subject suitable for treating a vascular disease is identified. The vascular disease in some instances is any vascular disease described above and herein. In exemplary embodiments, the vascular disease is post-angioplasty restenosis. In a step 1310, a blood vessel or blood vessels in the subject to target for treatment often is identified. In some instances, the blood vessel is any blood vessel described above and herein, such as a femoral artery. In a step 1315, a treatment catheter often is prepared with a pharmaceutical composition comprising temsirolimus and dexamethasone, although temsirolimus, dexamethasone, paclitaxel, contrast media or combinations thereof may be used as the therapeutic agent of choice. Alternative pharmaceutical compositions often are used as well, and the treatment catheter often comprises any of the drug injection and infusion devices described herein and above. In a step 1320, the catheter often is advanced through the vasculature of the subject to the target region(s), such as target region(s) in the blood vessel where plaque has been compressed by angioplasty. In a step 1325, the catheter often is positioned at or near the target region(s) of the blood vessel. In a step 1330, an expandable element of the catheter often is expanded to puncture the target region with a needle on the balloon. The expandable element often is an expandable segment, an expandable section, or a balloon of the treatment catheter. The needle often is a microneedle. In a step 1335, the needle of the treatment catheter often is positioned into the tissue surrounding the blood vessel so that the aperture of the needle often is positioned at the target tissue. In a step 1340, a therapeutic amount of the pharmaceutical composition comprising temsirolimus and dexamethasone (or other combinations of agents as previously described) often is injected into the target tissue surrounding the blood vessel. The target tissue often is adventitial tissue, perivascular tissue, or connective tissue surrounding a blood vessel. In a step 1345, the needle often is withdrawn from the tissue and the expandable element often is collapsed. In a step 1350, the treatment catheter with the collapsed expandable element and the needle often is removed from the vasculature of the subject.

Although the above steps show FIG. 12 and method 1300 of treating a vascular disease in FIG. 13 in accordance with embodiments, a person of ordinary skill in the art will recognize many variations based on the teaching described herein. The steps in some cases, are completed in a different order. Steps often are added or deleted. Some of the steps in some instances comprise sub-steps. Many of the steps often are repeated as often as beneficial to the treatment.

EXAMPLES

In-Vitro Protocols and Methods

To assess the ability of a range of drug or drug combinations and their effects on cell activation, pro-inflammatory cytokine production and cytotoxicity in PDGF-stimulated aortic smooth muscle cells in vitro was examined A range of concentrations of the mTOR inhibitors sirolimus and temsirolimus and the glucocorticoid dexamethasone were screened, in addition to combinations thereof, in comparison to the mitotic inhibitor paclitaxel.

Example 1: Metabolic Activity of VSMCs in the Presence of Select Drugs

Figure 14A:
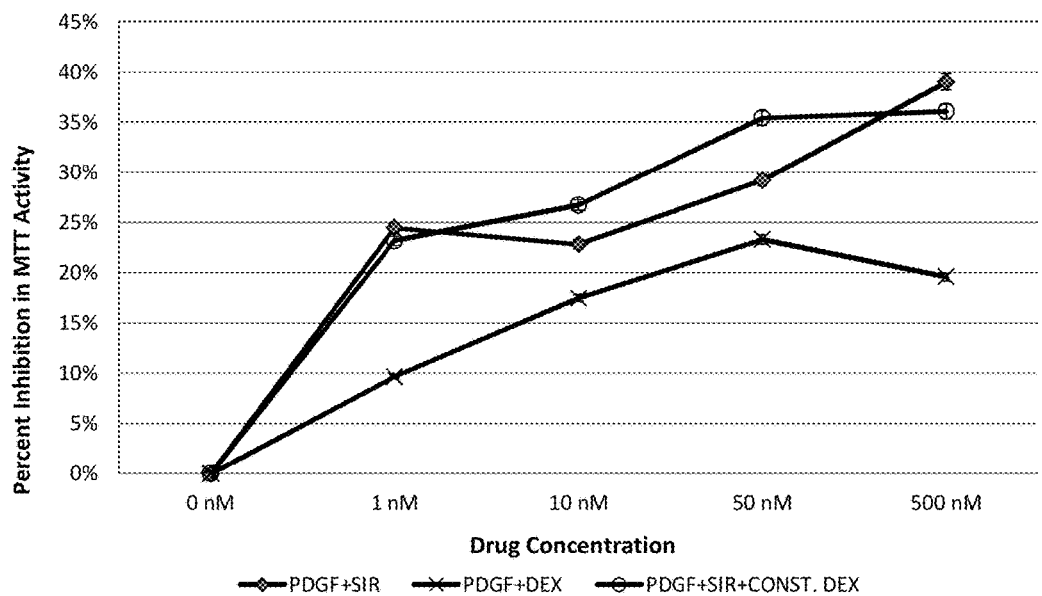
FIG. 14A illustrates the percent inhibition of metabolic activity and proliferation in the presence of sirolimus (SIR), dexamethasone (DEX) or sirolimus+dexamethasone (SIR+CONST. DEX) in an experiment measuring metabolic activity of human aortic vascular smooth muscle cells (VSMCs) in the presence of platelet-derived growth factor (PDGF).
Figure 14B:
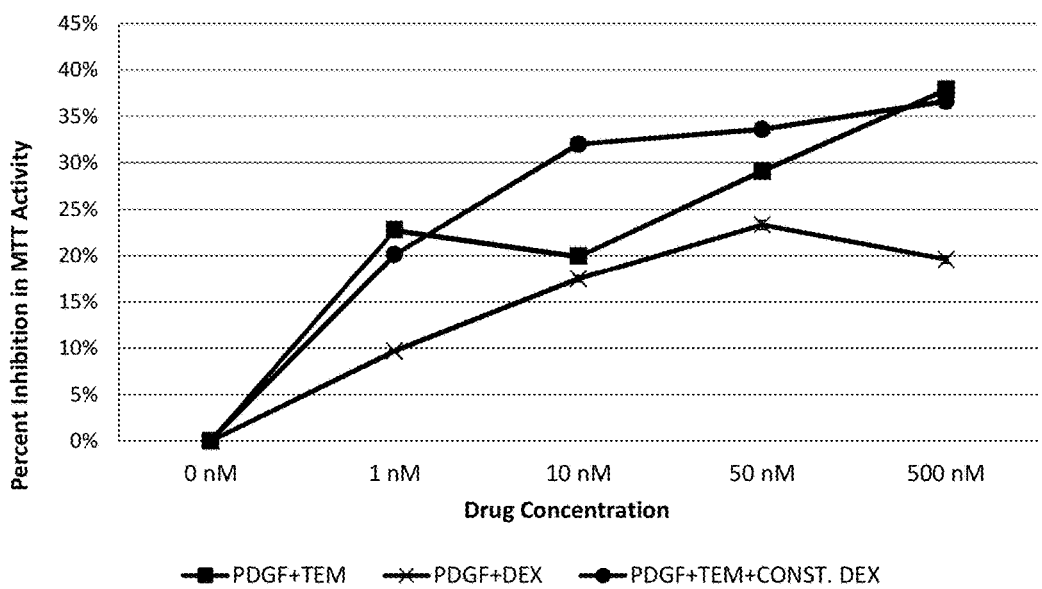
FIG. 14B illustrates the percent inhibition of metabolic activity and proliferation in the presence of temsirolimus (TEM), dexamethasone (DEX) or temsirolimus+dexamethasone (TEM+CONST. DEX) in an experiment measuring metabolic activity of human aortic VSMCs in the presence of platelet-derived growth factor (PDGF).
Figure 14C:
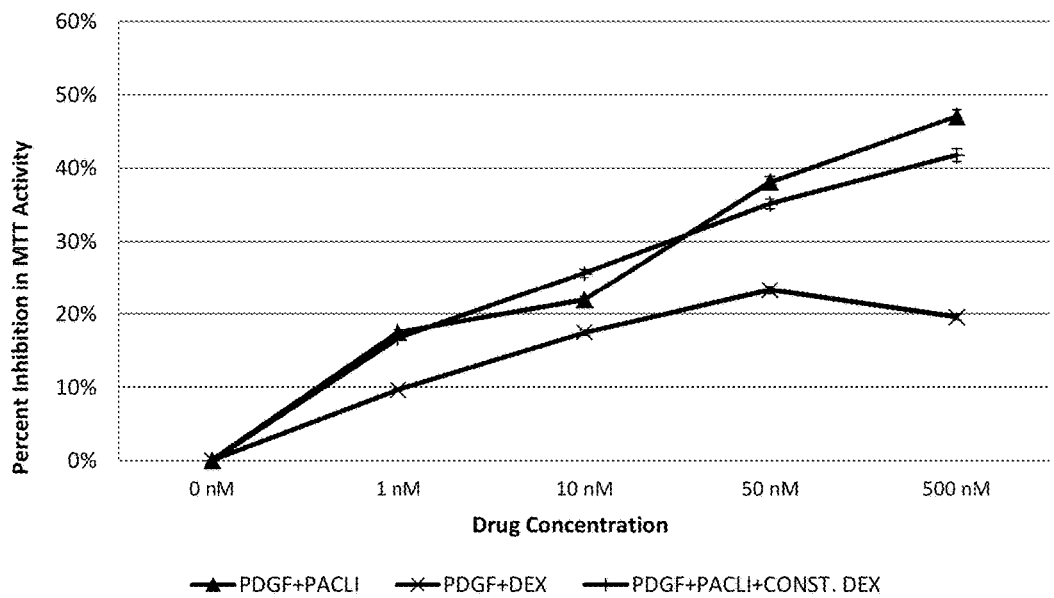
FIG. 14C depicts the percent inhibition of metabolic activity and proliferation in the presence of paclitaxel (PACLI), dexamethasone (DEX) or paclitaxel+dexamethasone (PACLI+CONST. DEX) in an experiment measuring metabolic activity of human aortic VSMCs in the presence of platelet-derived growth factor (PDGF).

Cultured human aortic VSMCs ($4\times10^5$ cells/mL) were grown in complete DMEM in 96 well plates (Corning) and stimulated with PDGF at 10 ng/mL (Peprotech) O/N. Utilizing established protocols for VSMC stimulation mediated by the growth factor, PDGF, drug was incubated at concentration ranges from 0, 1, 10, 100, 500 nanomolar (nM), in the presence or absence of 50 nM dexamethasone, for 12 or 48 hours. Drug-specific effects on cellular metabolic activity, pro-inflammatory cytokine production and cytotoxicity were examined. As a cytotoxic control for disruption of metabolic activity, we used actinomycin D (100 ng/mL or 398 nM). As a negative control, vehicle (5% (v/v) sterile DMSO in saline) was used. Following an 8 hour incubation in the presence of drug and stim (PDGF), MTT substrate was added and incubated for an additional 4 hrs prior to measurement. Absorbance readings were taken using a microtiter plate reader (Tecan). Data represent the average absorbance readings. Error bars represent the standard deviation amongst replicates. FIG. 14A shows the percent inhibition of metabolic activity and proliferation in the presence of sirolimus or sirolimus+dexamethasone. FIG. 14B shows the percent inhibition of metabolic activity and proliferation in the presence of temsirolimus or temsirolimus+dexamethasone. FIG. 14C shows the percent inhibition of metabolic activity and proliferation in the presence of paclitaxel or paclitaxel+ dexamethasone. Data represent the average of 9 replicate wells per condition and error bars represent the standard deviation of the 9 replicates.

In the presence of PDGF, conversion of MTT substrate into colorimetric product should occur to a significantly higher degree, as compared to media controls. Indeed, in FIG. 14A VSMCs stimulated with 10 ng/mL PDGF showed increased accumulation of metabolite compared to vehicle control (5% DMSO (v/v) in saline) and cytotoxic control (the transcription inhibitor actinomycin D at 100 ng/mL). Drug, specifically, temsirolimus, sirolimus and paclitaxel at higher concentrations had inhibitory activity in the MTT assay (FIGS. 14A-C).

Figure 19A:
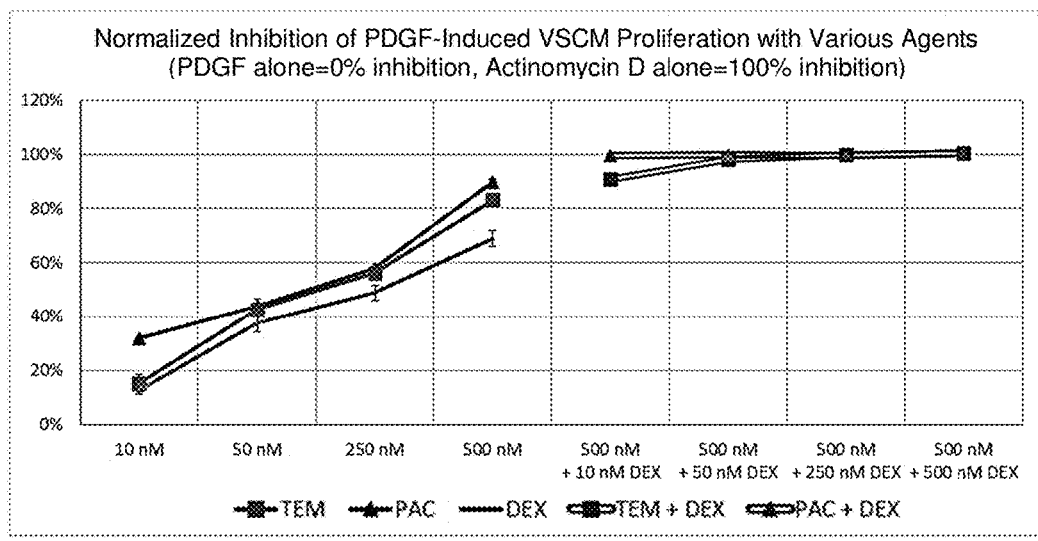
FIG. 19A depicts inhibition of PDGF-induced VSMC proliferation in the presence of increasing concentrations of temsirolimus (TEM), paclitaxel (PAC), or dexamethasone (DEX), and then with 500 nanomolar (nM) concentrations of either TEM or PAC as combined with increasing concentrations of DEX.

In yet a further experiment (FIG. 19A), cultured human aortic VSMCs ($4 \times 10^5$ cells/mL) were grown in complete DMEM in 96 well plates and stimulated with PDGF at 10 ng/mL (Peprotech). Single drug titrations of temsirolimus (TEM), paclitaxel (PAC) or dexamethasone (DEX) were administered (0, 10, 50, 500 nM), or fixed high-dose paclitaxel or temsirolimus were administered in combination with dexamethasone titrations (10, 50, 500 nM). After 8 h incubation, MTT substrate was added and incubated for an additional 4 hrs prior to measurement (T=12 hours). Absorbance readings were taken using a microtiter plate reader (Tecan). Data represent the average absorbance readings. Error bars represent the standard deviation amongst replicates. The anti-proliferative concentrations of temsirolimus, paclitaxel and dexamethasone were further analyzed in this study for their ability to abrogate PDGF-mediated proliferation at doses (dose range 1, 10, 50 500 nM). FIG. 19A presents the percent of inhibition that was identified in the presence of single or combination drugs. Low doses of all drugs, administered individually, had minimal inhibitory properties, as compared to high dose of each drug. Addition of dexamethasone to high-dose paclitaxel or temsirolimus increased the anti-proliferative effect in each case.

Example 2: VSMC TNFα Cytokine Production in the Presence of Select Drugs

Figure 15A:
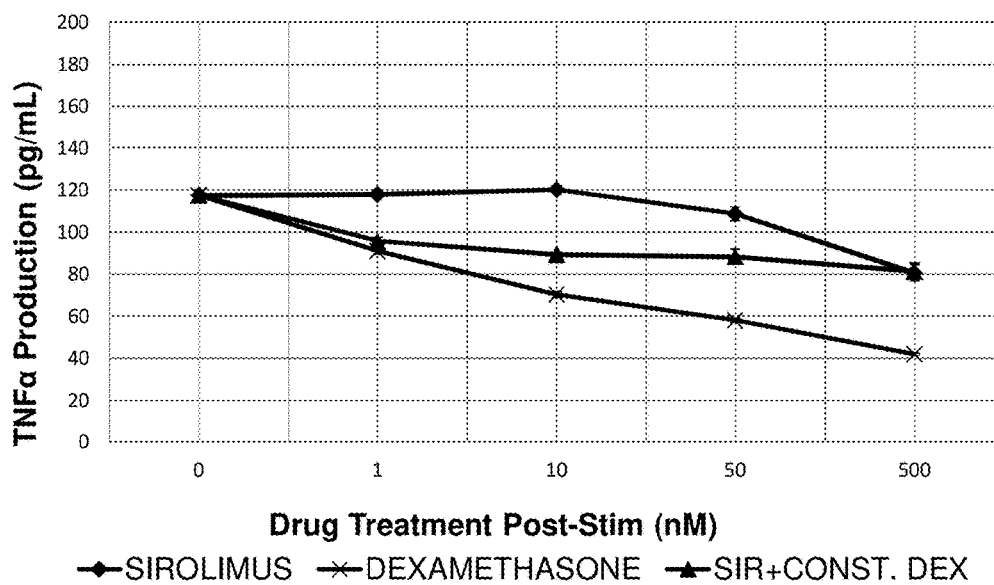
FIG. 15A depicts tissue necrosis factor α (TNFα) production in the presence of increasing concentrations of sirolimus, dexamethasone or sirolimus+50 nM dexamethasone in an experiment measuring TNFα production of human aortic VSMCs.
Figure 15B:
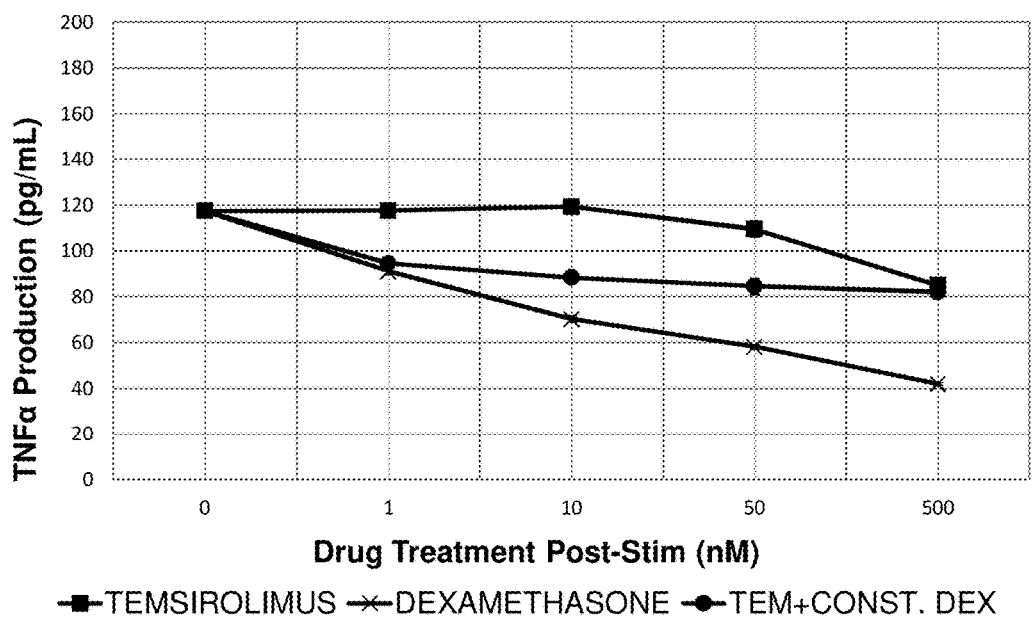
FIG. 15B depicts TNFα production in the presence of increasing concentrations of temsirolimus, dexamethasone or temsirolimus+50 nM dexamethasone in an experiment measuring TNFα production of human aortic VSMCs.
Figure 15C:
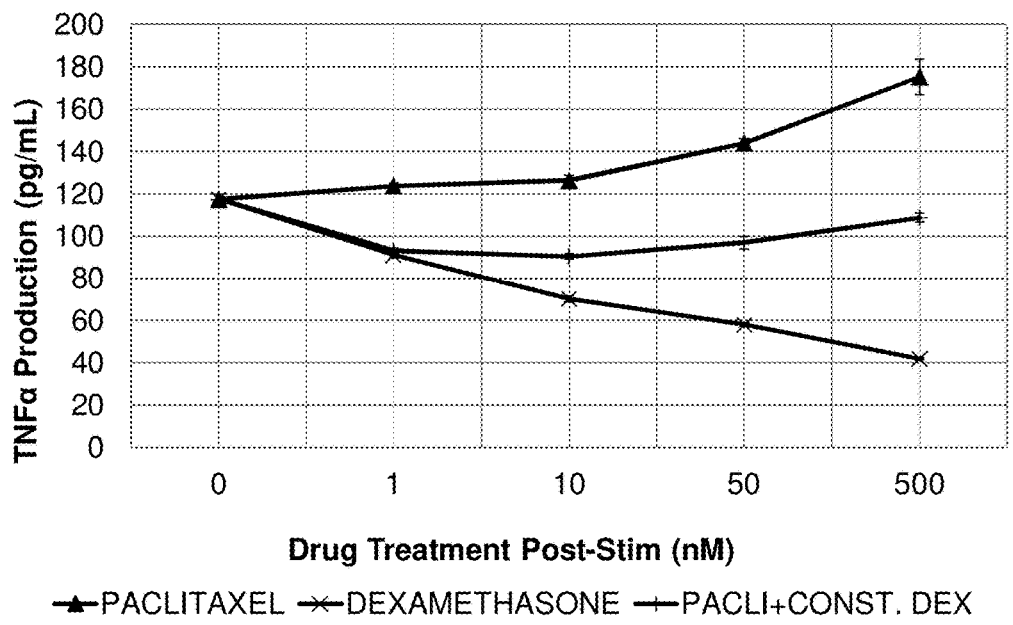
FIG. 15C depicts TNFα production in the presence of increasing concentrations of paclitaxel, dexamethasone or paclitaxel+50 nM dexamethasone in an experiment measuring TNFα production of human aortic VSMCs.

Cultured human aortic VSMCs ($4 \times 10^5$ cells/mL) were grown in complete DMEM in 96 well plates (Corning) and stimulated with PDGF at 10 ng/mL (Peprotech) O/N. As a negative control (0 nM Drug)), vehicle (5% (v/v) sterile DMSO in saline) was used. Following a 48 hour incubation in the presence of drug and stimulant (PDGF), 50 uL of supernatant from each well was collected and ELISAs were performed to measure TNFα levels. Pro-inflammatory cytokine expression was examined under these conditions by measuring TNFα levels in cell supernatant after 48 h by enzyme-linked immunoassay (ELISA; Peprotech #900-T16, #900-T25). Absorbance readings were taken using a microtiter plate reader (Tecan). FIG. 15A shows TNFα production in the presence of increasing concentrations of sirolimus or sirolimus+50 nM dexamethasone. FIG. 15B shows TNFα production in the presence of increasing concentrations of temsirolimus or temsirolimus+50 nM dexamethasone. FIG. 15C shows TNFα production in the presence of increasing concentrations of paclitaxel or paclitaxel+50 nM dexamethasone. Data represent the average of 9 replicate wells per condition and error bars represent the standard deviation of the 9 replicates. mTOR inhibitors decreased TNFα production at higher doses and the presence of dexamethasone decreased TNFα production when combined with mTOR inhibitors. Dexamethasone alone strongly decreased TNFα production in a dose-dependent manner Conversely, paclitaxel activated pro-inflammatory cytokine expression, which was ameliorated by the addition of 50 nM dexamethasone.

In yet a further experiment (FIG. 19E) cultured human aortic VSMCs ($4 \times 10^5$ cells/mL) were grown in complete DMEM in 96 well plates (Corning) and stimulated with PDGF at 10 ng/mL (Peprotech). Single drug titrations of temsirolimus (TEM), paclitaxel (PAC) or dexamethasone (DEX) were administered (0, 10, 50, 500 nM), or fixed high-dose paclitaxel or temsirolimus were administered in combination with dexamethasone titrations (10, 50, 500 nM). Cells were incubated for 48 h and TNFα levels were measured by ELISA (Peprotech). Absorbance readings were taken using a microtiter plate reader (Tecan). Data represent the average absorbance readings. Error bars represent the standard deviation amongst triplicate wells of triplicate plates. In this experiment, paclitaxel induced a dose-dependent upregulation of the pro-inflammatory cytokines TNFα, while temsirolimus and dexamethasone, administered individually, induced a dose-dependent reduction in the same cytokine. Dexamethasone similarly demonstrated anti-inflammatory effects in this study. Furthermore, at high dose (500 nM) paclitaxel, TNFα expression levels are highest; addition of dexamethasone at any dose (10, 50, 500 nM) significantly reduced pro-inflammatory cytokine production of paclitaxel.

Example 3: VSMC IL6 Cytokine Production in the Presence of Select Drugs

Figure 16A:
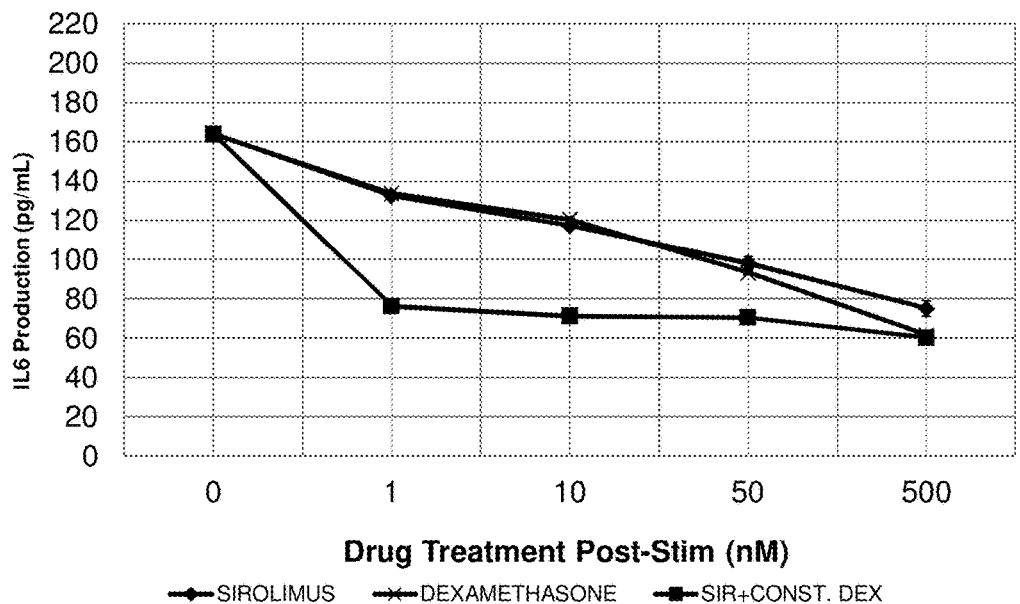
FIG. 16A depicts interleukin 6 (IL6) production in the presence of increasing concentrations of sirolimus, dexamethasone or sirolimus+50 nM dexamethasone in an experiment measuring IL6 cytokine production of human aortic VSMCs.
Figure 16B:
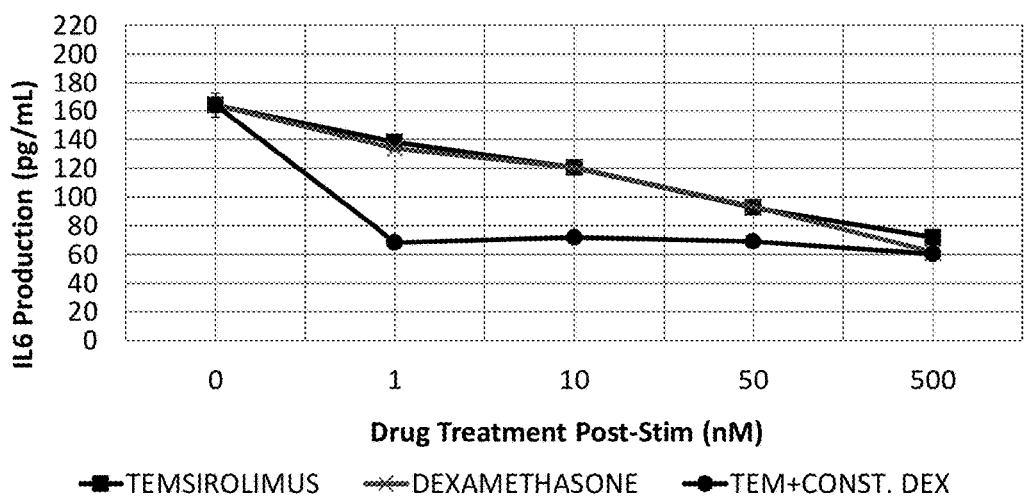
FIG. 16B depicts IL6 production in the presence of increasing concentrations of temsirolimus, dexamethasone or temsirolimus+50 nM dexamethasone in an experiment measuring IL6 cytokine production of human aortic VSMCs.
Figure 16C:
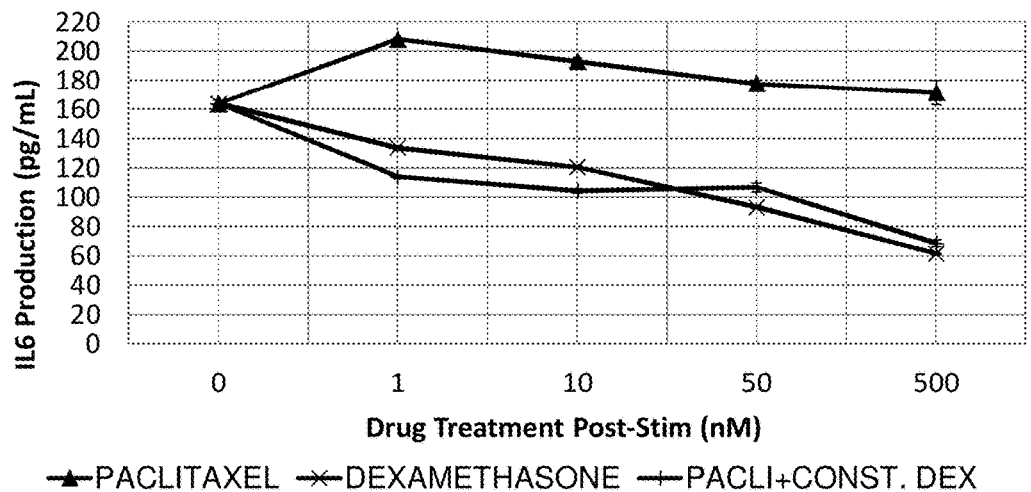
FIG. 16C depicts IL6 production in the presence of increasing concentrations of paclitaxel or paclitaxel, dexamethasone+50 nM dexamethasone in an experiment measuring IL6 cytokine production of human aortic VSMCs.

Cultured human aortic VSMCs ($4 \times 10^5$ cells/mL) were grown in complete DMEM in 96 well plates (Corning) and stimulated with PDGF at 10 ng/mL (Peprotech) O/N. As a negative control (0 nM Drug), vehicle (5% (v/v) sterile DMSO in saline) was used. Following a 48 hour incubation in the presence of drug and stimulant (PDGF), 50 uL of supernatant from each well was collected and ELISAs were performed to measure IL6 levels. Pro-inflammatory cytokine expression was examined under these conditions by measuring IL6 levels in cell supernatant after 48 h by enzyme-linked immunoassay (ELISA; Peprotech #900-T16, #900-T25). Absorbance readings were taken using a microtiter plate reader (Tecan). FIG. 16A shows IL6 production in the presence of increasing concentrations of sirolimus or sirolimus+50 nM dexamethasone. FIG. 16B shows IL6 production in the presence of increasing concentrations of temsirolimus or temsirolimus+50 nM dexamethasone. FIG. 16C shows IL6 production in the presence of increasing concentrations of paclitaxel or paclitaxel+50 nM dexamethasone. Data represent the average of 9 replicate wells per condition and error bars represent the standard deviation of the 9 replicates. With the exception of paclitaxel, the mTOR inhibitors and the glucocorticoid inhibited IL6 production in a dose-dependent manner (FIGS. 16A-C).

The percent change in TNFα and IL6 levels compared to vehicle control levels (set as baseline) were also analyzed and are presented in FIGS. 15A-C and FIGS. 16A-C, respectively. The mTOR inhibitors each decreased TNFα levels when present at 50-500 nM. Paclitaxel induced IL6 and TNFα production by SMCs at all doses tested. Moreover, TNFα levels increased steadily as paclitaxel concentrations increased with no significant change in IL6 levels between 50 and 500 nM drug. Dexamethasone ameliorated paclitaxel-induced TNFα and IL6 production in VSMCs. Also very noteworthy was the unexpected finding that mTOR inhibitors alone decreased IL6 production in a dose-dependent manner and similar to dexamethasone. mTOR inhibitor+dexamethasone showed an enhanced ability to inhibit IL6 production by VSMCs.

In yet a further experiment (FIG. 19D) cultured human aortic VSMCs ($4 \times 10^5$ cells/mL) were grown in complete DMEM in 96 well plates (Corning) and stimulated with PDGF at 10 ng/mL (Peprotech). Single drug titrations of temsirolimus (TEM), paclitaxel (PAC) or dexamethasone (DEX) were administered (0, 10, 50, 500 nM), or fixed high-dose paclitaxel or temsirolimus were administered in combination with dexamethasone titrations (10, 50, 500 nM). Cells were incubated for 48 h and IL6 levels were measured by ELISA (Peprotech). Absorbance readings were taken using a microtiter plate reader (Tecan). Data represent the average absorbance readings. Error bars represent the standard deviation amongst triplicate wells of triplicate plates. In this experiment, paclitaxel induced a dose-dependent upregulation of the pro-inflammatory cytokines IL6, while temsirolimus and dexamethasone, administered individually, induced a dose-dependent reduction in the same cytokine. Dexamethasone similarly demonstrated anti-inflammatory effects in this study. Furthermore, at high dose (500 nM) paclitaxel, IL6 expression levels are highest; addition of dexamethasone at any dose (10, 50, 500 nM) significantly reduced pro-inflammatory cytokine production of paclitaxel.

Example 4: Apoptosis in Drug-Treated VSMCs

Figure 17A:
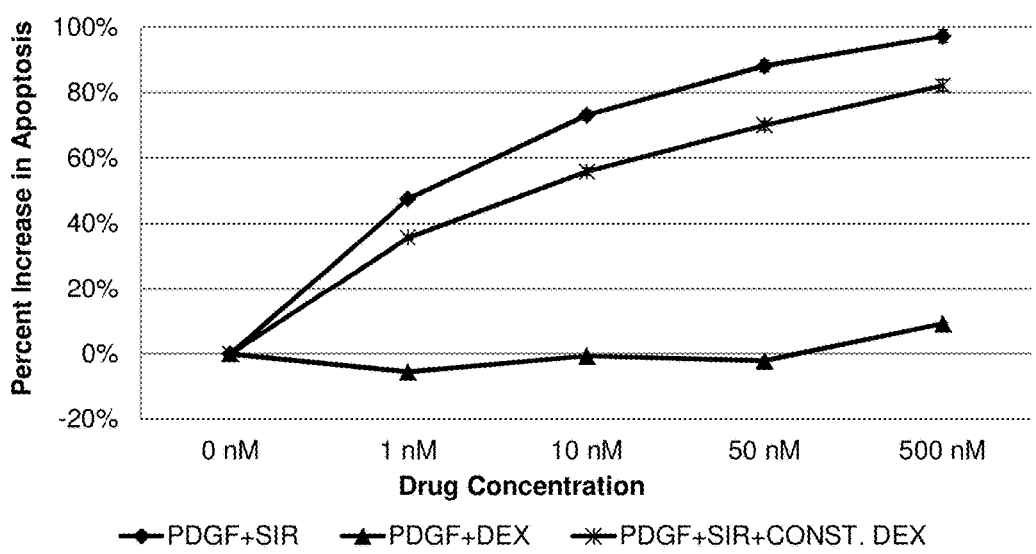
FIG. 17A depicts apoptosis by the measurement of Caspase 3 activation in the presence of increasing concentrations of sirolimus, dexamethasone or sirolimus+50 nM dexamethasone in an experiment measuring apoptosis in human aortic VSMCs.
Figure 17B:
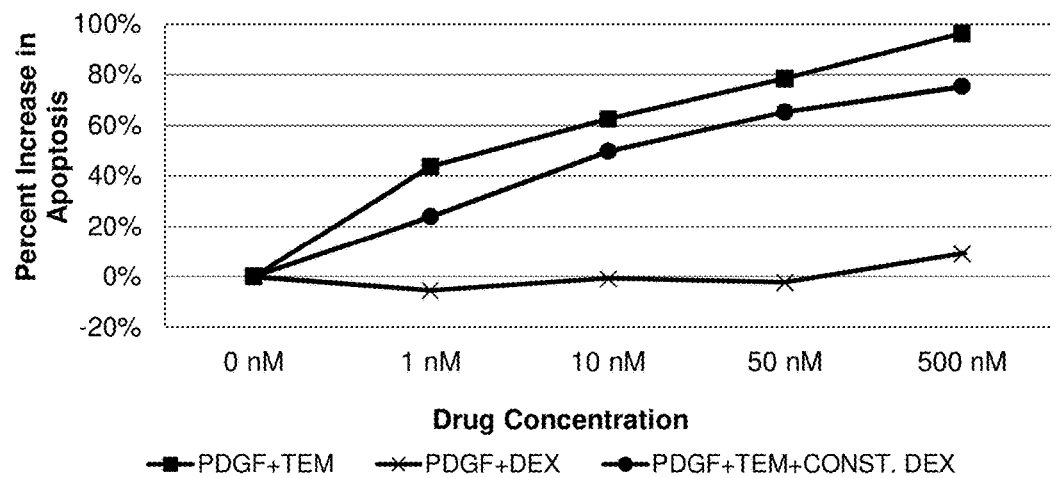
FIG. 17B depicts apoptosis by the measurement of Caspase 3 activation in the presence of increasing concentrations of temsirolimus, dexamethasone or temsirolimus+50 nM dexamethasone in an experiment measuring apoptosis in human aortic VSMCs.
Figure 17C:
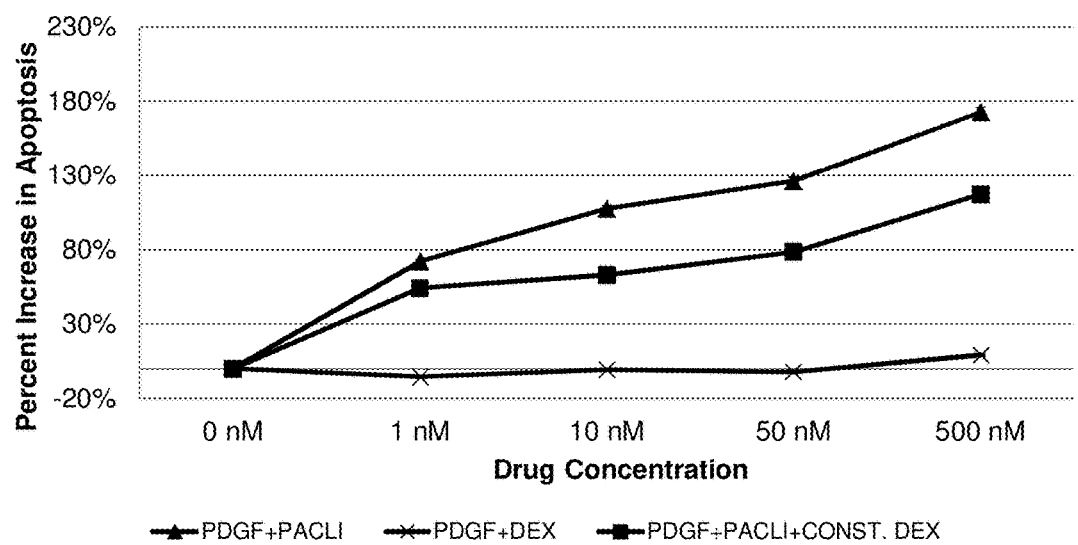
FIG. 17C depicts apoptosis by the measurement of Caspase 3 activation in the presence of increasing concentrations of paclitaxel, dexamethasone or paclitaxel+50 nM dexamethasone in an experiment measuring apoptosis in human aortic VSMCs.

Cultured human aortic VSMCs ($4 \times 10^5$ cells/mL) were grown in complete DMEM in 96 well plates (Corning) and stimulated with PDGF at 10 ng/mL (Peprotech). Drug (sirolimus; temsirolimus; paclitaxel; dexamethasone) or vehicle control was incubated for 12 hours. At harvest, cells were gently lysed and a Caspase 3 ELISA was performed (Cell Signaling Technologies, Cat #7190). Absorbance readings were taken using a microtiter plate reader (Tecan). FIG. 17A shows Caspase 3 activation in the presence of increasing concentrations of sirolimus or sirolimus+50 nM dexamethasone. FIG. 17B shows Caspase 3 activation in the presence of increasing concentrations of temsirolimus or temsirolimus+50 nM dexamethasone. FIG. 17C shows Caspase 3 activation in the presence of increasing concentrations of paclitaxel or paclitaxel+50 nM dexamethasone. Data represent the average of 9 replicate wells per condition and error bars represent the standard deviation of the 9 replicates. Baseline levels of VSMC apoptosis were obtained using vehicle controls and values were set to zero. The percent change in apoptosis in the presence of drug was determined from baseline (FIG. 17A-C). Apoptosis was observed to be induced in a dose-dependent manner for all mTOR inhibitors and paclitaxel, with paclitaxel inducing up to a 173% average increase in apoptosis under the test conditions. Interestingly, dexamethasone did not induce significant apoptosis. Data also showed that low dose dexamethasone decreased the mTOR inhibitor-induced effects.

Figure 19B:
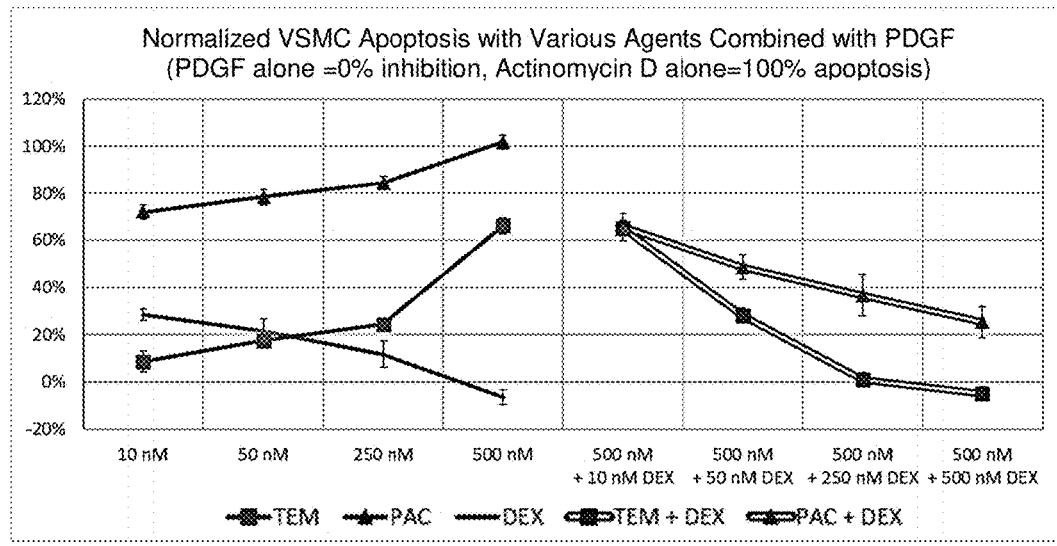
FIG. 19B depicts normalized VSMC apoptosis in the presence of PDGF and increasing concentrations of temsirolimus (TEM), paclitaxel (PAC), or dexamethasone (DEX), and then with 500 nanomolar (nM) concentrations of either TEM or PAC as combined with increasing concentrations of DEX.

In yet another experiment (FIG. 19B) cultured human aortic VSMCs ($4 \times 10^5$ cells/mL) were grown in complete DMEM in 96 well plates (Corning) and stimulated with PDGF at 10 ng/mL (Peprotech). Single drug titrations of temsirolimus (TEM), paclitaxel (PAC) or dexamethasone (DEX) were administered (0, 10, 50, 500 nM), or fixed high-dose paclitaxel or temsirolimus were administered in combination with dexamethasone titrations (10, 50, 500 nM). Cells were then incubated for 12 hours. At harvest, plates were centrifuged at 800 rpm in a clinical centrifuge, and supernatant was carefully removed. Cells were then fixed and permeabilized and assayed for cytoplasmic caspase 3 levels by ELISA, according to manufacturer instructions (Cell Signaling Technologies). Absorbance readings were taken using a microtiter plate reader (Tecan). Data represent the average absorbance readings. Error bars represent the standard deviation amongst replicates. With this experiment, we revisited whether paclitaxel, temsirolimus or dexamethasone could induce cytotoxicity through an apoptotic mechanism at lower doses (1, 10, 50, 500 nM) by measuring the amount of activated Caspase 3 enzyme present under various treatment conditions. FIG. 19B presents the amount of apoptosis inhibited compared to vehicle control. Briefly, paclitaxel, at all doses tested, was shown to promote apoptosis (lack of inhibition), which was rescued by the addition of dexamethasone. The same rescue effect of dexamethasone at increasing concentrations was also observed when used in conjunction with high dose temsirolimus.

Example 5: Necrotic LDH Measurements in Drug-Treated VSMCs

Figure 18A:
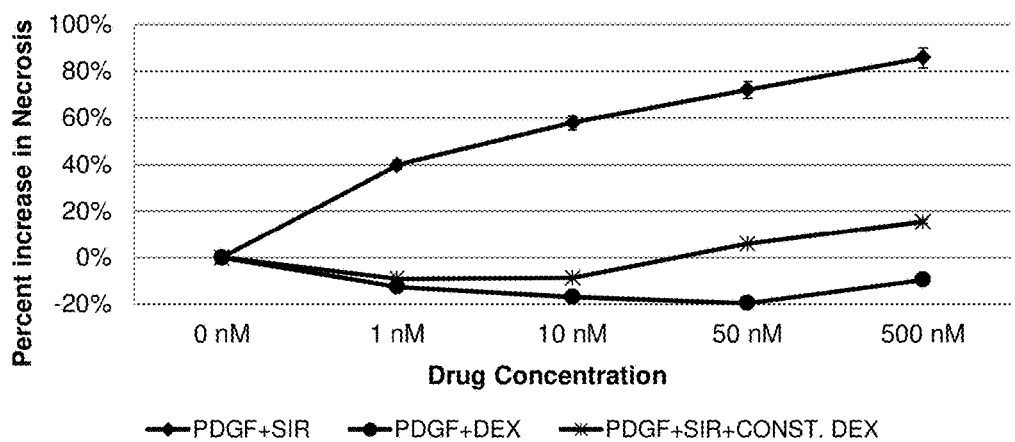
FIG. 18A depicts necrosis by the measurement of LDH release in the presence of increasing concentrations of sirolimus, dexamethasone or sirolimus+50 nM dexamethasone in an experiment measuring necrosis in human aortic VSMCs.
Figure 18B:
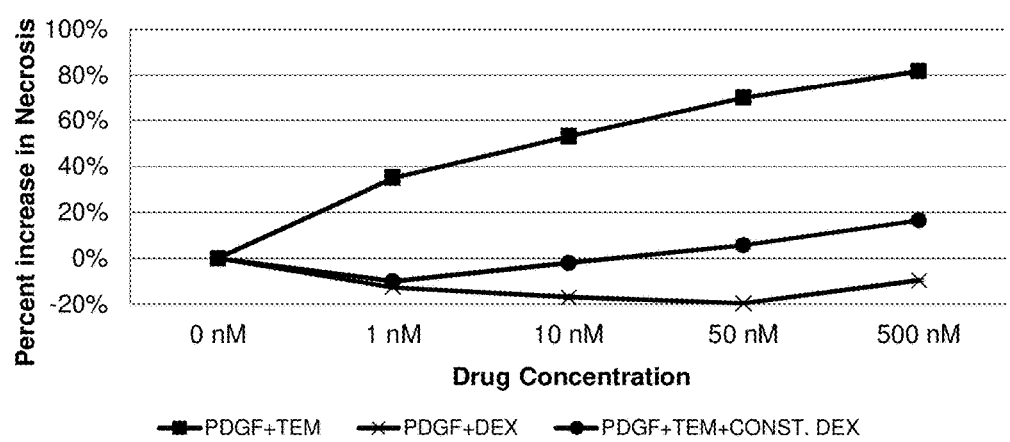
FIG. 18B depicts necrosis by the measurement of LDH release in the presence of increasing concentrations of temsirolimus, dexamethasone or temsirolimus+50 nM dexamethasone in an experiment measuring necrosis in human aortic VSMCs.
Figure 18C:
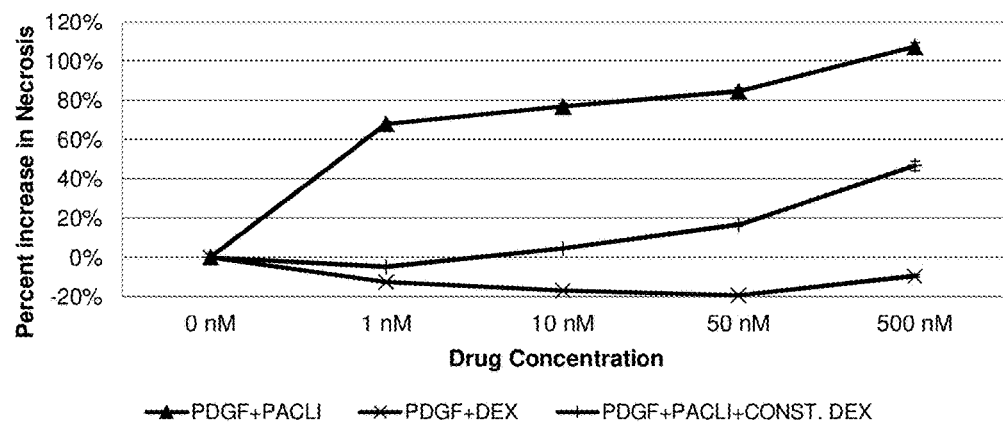
FIG. 18C depicts necrosis by the measurement of LDH release in the presence of increasing concentrations of paclitaxel, dexamethasone or paclitaxel+50 nM dexamethasone in an experiment measuring necrosis in human aortic VSMCs.

Cultured human aortic VSMCs ($4 \times 10^5$ cells/mL) were grown in complete DMEM in 96 well plates (Corning) and stimulated with PDGF at 10 ng/mL (Peprotech). Drug (sirolimus; temsirolimus; paclitaxel; dexamethasone) or vehicle control was incubated for 12 hours. At harvest, plates were centrifuged at 800 rpm in a clinical centrifuge, and supernatant was carefully removed and assayed for lysed cells by measuring the LDH released into the culture media by ELISA, according to manufacturer instructions. Absorbance readings were taken using a microtiter plate reader (Tecan). Temsirolimus, sirolimus, paclitaxel and dexamethasone were also assessed for toxicity using the LDH release assay to measure necrosis and cytolysis in PDGF-treated VSMCs (FIG. 18A-C). Data in FIG. 18A represent the LDH release in the presence of increasing concentrations of sirolimus or sirolimus+50 nM dexamethasone. FIG. 18B shows LDH release in the presence of increasing concentrations of temsirolimus or temsirolimus+50 nM dexamethasone. FIG. 18C shows LDH release in the presence of increasing concentrations of paclitaxel or paclitaxel+50 nM dexamethasone. Data represent the average of 9 replicate wells per condition and error bars represent the standard deviation of the 9 replicates. A dose-dependent relationship was observed with mTOR inhibitors and paclitaxel. Dexamethasone did not induce LDH release at any dose and suppressed LDH release compared to vehicle. A 50 nM concentration of dexamethasone also decreased mTOR and paclitaxel-mediated LDH release in these studies.

Figure 19C:
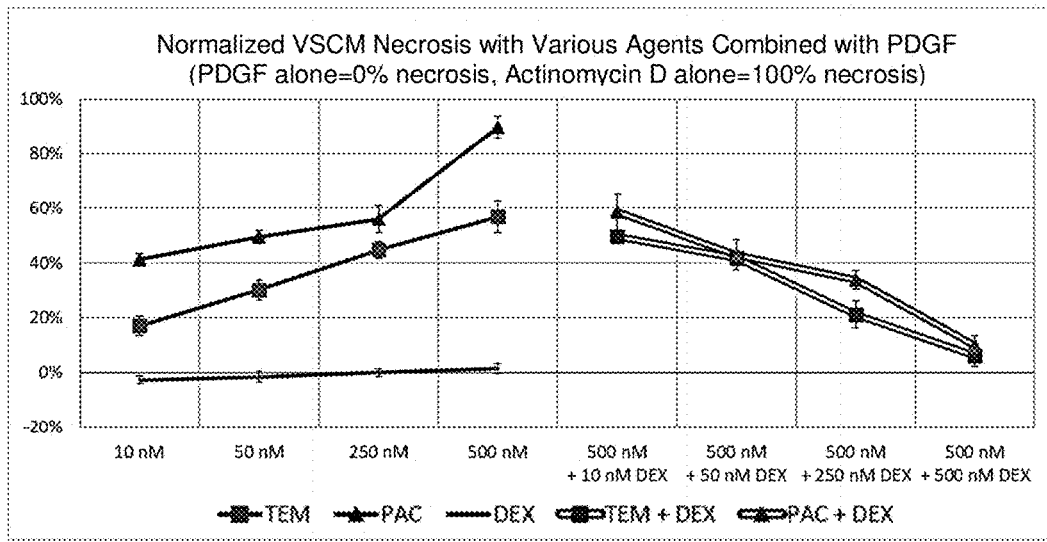
FIG. 19C depicts normalized VSMC necrosis in the presence of PDGF and increasing concentrations of temsirolimus (TEM), paclitaxel (PAC), or dexamethasone (DEX), and then with 500 nanomolar (nM) concentrations of either TEM or PAC as combined with increasing concentrations of DEX.
Figure 19D:
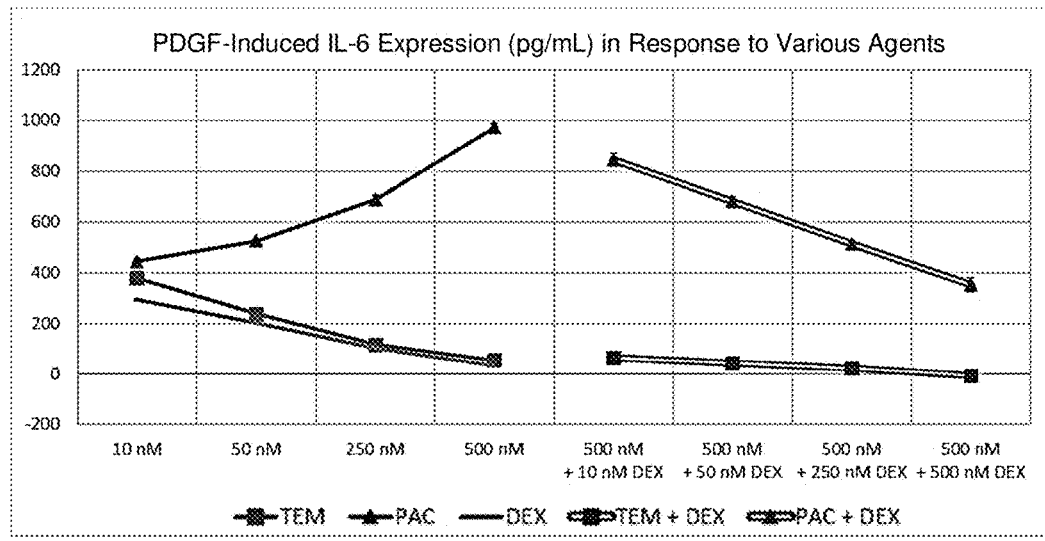
FIG. 19D depicts PDGF-induced interleukin-6 (IL6) expression in the presence of increasing concentrations of temsirolimus (TEM), paclitaxel (PAC), or dexamethasone (DEX), and then with 500 nanomolar (nM) concentrations of either TEM or PAC as combined with increasing concentrations of DEX.
Figure 19E:
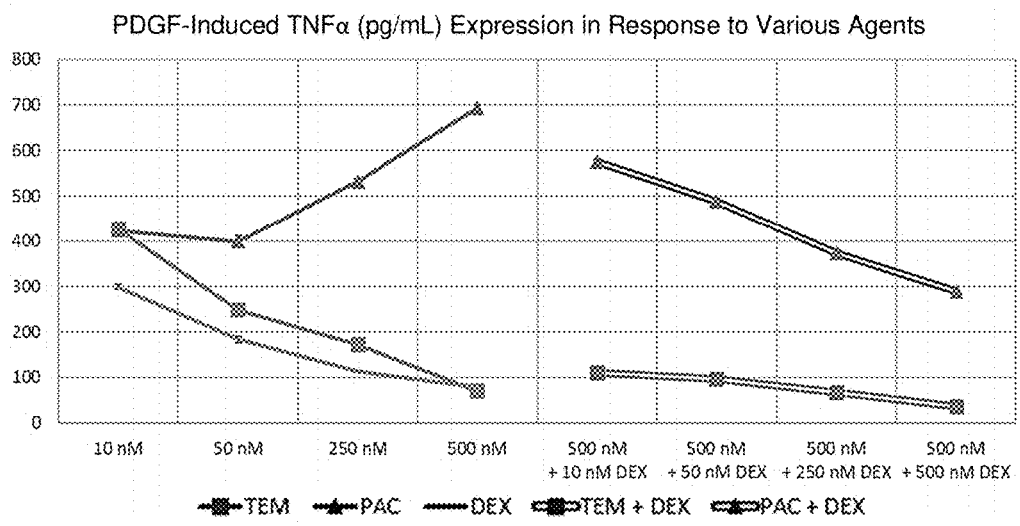
FIG. 19E depicts PDGF-induced tissue necrosis factor α (TNFα) in the presence of increasing concentrations of temsirolimus (TEM), paclitaxel (PAC), or dexamethasone (DEX), and then with 500 nanomolar (nM) concentrations of either TEM or PAC as combined with increasing concentrations of DEX.

In yet a further experiment (FIG. 19C), cultured human aortic VSMCs ($4 \times 10^5$ cells/mL) were grown in complete DMEM in 96 well plates (Corning) and stimulated with PDGF at 10 ng/mL (Peprotech). Single drug titrations of temsirolimus (TEM), paclitaxel (PAC) or dexamethasone (DEX) were administered (0, 10, 50, 500 nM), or fixed high-dose paclitaxel or temsirolimus were administered in combination with dexamethasone titrations (10, 50, 500 nM). Treated cells were then incubated for 12 hours. At harvest, plates were centrifuged at 800 rpm in a clinical centrifuge, and supernatant was carefully removed and assayed for LDH by ELISA according to manufacturer instructions. Absorbance readings were taken using a microtiter plate reader (Tecan). Data represent the average absorbance readings. Error bars represent the standard deviation amongst replicates. Toxicity of paclitaxel, through a necrotic mechanism, has been shown in our previous studies. In this study we assessed lower concentrations of drug 1, 10, 50, 500 nM to see if we could identify a drug range that was safer more well-tolerated by VSMCs. FIG. 19C presents data showing that all concentrations of paclitaxel tested demonstrated necrotic cytotoxicity. Additionally, drug combinations containing paclitaxel similarly demonstrated necrotic activity, however the presence of dexamethasone rescued this activity. On the contrary, toxicity of a necrotic nature was not observed for dexamethasone at any concentration tested.

Example 6: Porcine Model of Femoral Vessel Injury

In a porcine model of femoral artery injury, a dose of temsirolimus, dexamethasone, or a combination thereof is administered directly into the tissue around an injured artery through a catheter with a needle. Porcine vascular anatomy is similar to human anatomy, allowing the study of medical equipment intended for use in humans. Porcine vascular pathology allows for the development of stenotic arteries for the study of anti-stenotic or anti-restenotic therapies intended for use in humans.

In twenty-four Yorkshire pigs, the femoral artery in each leg (hind leg) is injured by angioplasty overstretch and followed with either temsirolimus, dexamethasone, combination of both drugs, or control saline injection, for bilateral injury and injection. The angioplasty balloon is selected to be 40-60% larger than the reference diameter of the artery to be injured and is delivered by a catheter to the target injury site by carotid artery access. The angioplasty balloon is inflated to 10-20 atmosphere of pressure three times for 30 seconds each inflation at the target injury site. After the balloon is removed, the Mercator MedSystems Bullfrog® Micro-Infusion Device microneedle catheter is used to deliver either temsirolimus, dexamethasone, combination of both drugs, or control saline by injection into the adventitia and perivascular tissue around the injured artery at the center of each target injury site. The injections are administered under and verified by fluoroscopy. The animals are monitored before, during, and after the procedure, ensuring that all animals survive without adverse incidents until sacrifice.

Temsirolimus Preparation.

The 25 mg/mL of Torisel® (temsirolimus) is diluted to 10 mg/ml with the supplied diluent and further diluted to 1.0 mg/mL in 0.9% sodium chloride solution. Then, the 1.0 mg/mL temsirolimus is diluted in a ratio of 4 parts temsirolimus to 2 parts contrast medium, IsoVUE 370, and 4 parts 0.9% sodium chloride solution, for a final temsirolimus concentration of 400 µg/ml. This temsirolimus preparation is subsequently administered in temsirolimus-treated group pigs. Similarly, a control solution is prepared by mixing 0.9% sodium chloride solution at 4:1 ratio with a contrast medium, Isovue-370. This control solution is administered in control group pigs.

Dexamethasone Preparation.

A 10 mg/mL solution of dexamethasone is diluted to 5 mg/mL in 0.9% sodium chloride solution. Then, the 5 mg/mL dexamethasone is mixed at 4:1 ratio with a contrast medium, Isovue-370, for a final dexamethasone concentration of 4 mg/mL. This dexamethasone preparation is subsequently administered in dexamethasone-treated group pigs.

Temsirolimus/Dexamethasone Combination Preparation.

The 1.0 mg/mL temsirolimus and the 10 mg/mL dexamethasone solutions are mixed at a 2:2:1 ratio with a contrast medium, Isovue-370, for a final temsirolimus concentration of 0.4 mg/mL, and a final dexamethasone concentration of 4.0 mg/mL. This temsirolimus/dexamethasone preparation is subsequently administered in temsirolimus/dexamethasone-treated group pigs.

Temsirolimus-Treated Group.

Six pigs receive a single dose of temsirolimus (1.5 mL of 400 µg/mL temsirolimus) in the tissue around each 3-cm injured femoral artery segment, for a total of two doses per animal. In each case, all temsirolimus treated animals undergo perivascular infusion into the femoral artery adventitia. Two pigs are sacrificed at each time point of 3 days, 7 days, and 28 days post-procedure, and each pig is analyzed for histopathology, pharmacokinetics, and safety evaluation.

Dexamethasone-Treated Group.

Six pigs receive a single dose of dexamethasone (1.5 mL of 4.0 mg/mL dexamethasone) in the tissue around each injured femoral artery, for a total of two doses per animal. In each case, all dexamethasone treated animals undergo perivascular infusion into the femoral artery adventitia. Two pigs are sacrificed at each time point of 3 days, 7 days, and 28 days post-procedure, and each pig is analyzed for histopathology, pharmacokinetics, and safety evaluation.

Temsirolimus/Dexamethasone Combination-Treated Group.

Six pigs receive a single dose of the temsirolimus/dexamethasone composition (1.5 ml of 400 µg/mL temsirolimus/4.0 mg/mL dexamethasone) in the tissue around each injured femoral artery, for a total of two doses per animal. In each case, all temsirolimus treated animals undergo perivascular infusion into the femoral artery adventitia. Two pigs are sacrificed at each time point of 3 days, 7 days, and 28 days post-procedure, and each pig is analyzed for histopathology, pharmacokinetics, and safety evaluation.

Control Group.

Six pigs serve as control animals. Each pig receives 2 injury sites in femoral arteries, for a total of 12 injury sites among the 6 pigs. Each injury site receives 1.5 ml of 0.9% sodium chloride (saline) diluted 4:1 ratio with contrast medium (Isovue-370). Two pigs are sacrificed at each time point of 3 days, 7 days, and 28 days post-procedure, and each pig is analyzed for histopathology, pharmacokinetics, and safety evaluation.

All treatment and control group animals will successfully receive their respective injection administered directly to the adventitia and perivascular tissues of the femoral arteries. All injection sites except the two control sites will have complete or partial circumferential and longitudinal coverage of the target site by the injection.

Safety Evaluation.

Local and systemic toxicity is assessed by clinical observations and clinical pathology either during the survival duration or by analysis of tissues post mortem.

Outcomes.

Cellular proliferation as measured by Ki-67 expression, BrdU expression, histopathology, pharmacokinetics, and safety evaluation will be compared for treatment and control groups to ascertain the effect of combination therapy on restenosis in a porcine model.

Example 8: Porcine Model of Femoral Vessel Injury with Sequential Combination Therapy The general method of Example 7 is followed, with the modification that the researcher wants to study the effects of sequential treatment with both drugs. The combination temsirolimus/dexamethasone-treatment group is removed, the temsirolimus group receives a dexamethasone injection 24 hours after treatment, and the dexamethasone group receives a temsirolimus injection 24 hours after treatment. Outcomes are evaluated in a similar manner, and the effect of sequential treatment is ascertained.

Example 9: Porcine Model of Femoral Vessel Injury with Paclitaxel

The general method of Example 7 is followed, with the modification that the researcher replaces temsirolimus with paclitaxel, in dosages described herein. Outcomes are evaluated in a similar manner.

Example 10: Porcine Model of Femoral Vessel Injury with Sequential Paclitaxel Combination Therapy The general method of Example 8 is followed, with the modification that the researcher replaces temsirolimus with paclitaxel, in dosages described herein. Outcomes are evaluated in a similar manner, and the effect of sequential treatment is ascertained.

Example 11: In-Vitro Cytoxicity Study

Figure 20:
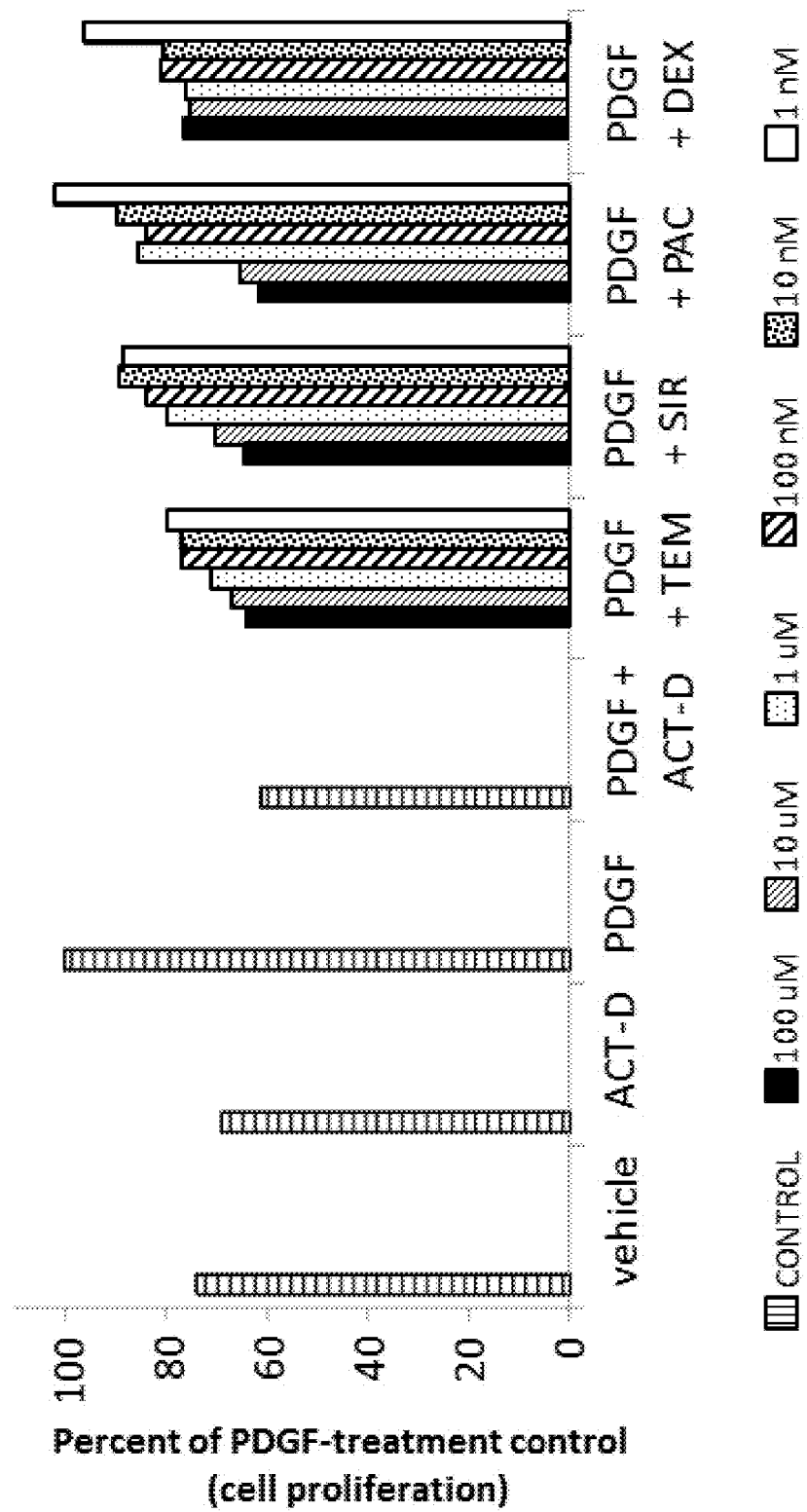
FIG. 20 depicts PDGF-induced cell proliferation in the presence of decreasing concentrations (100 uM to 1 nM) of temsirolimus (TEM), sirolimus (SIR), paclitaxel (PAC), or dexamethasone (DEX), vehicle control, or cytotoxic control actinomycin D (ACT-D).

A study was performed to assess the ability of a range of drug or drug combinations to induce cytotoxicity in PDGF-stimulated aortic smooth muscle and endothelial cells in vitro. Cultured human aortic VSMCs ($4 \times 10^5$ cells/mL) were grown in complete DMEM in 96 well plates and stimulated with PDGF at 10 ng/mL (Peprotech). A range of concentrations of drug (SIR, sirolimus; TEM, temsirolimus; PAC, paclitaxel; DEX, dexamethasone) and vehicle control or cytotoxic control (ACT D, actinomycin D) were screened (FIG. 20). Utilizing protocols for EC and VSMC stimulation mediated by the growth factor, PDGF, cells were incubated in drug at concentration ranges from 0, 1, 10, 100 nM, 1, 10, 100 μM for 12 hours prior to assessment for cellular activation and cytotoxicity. Prior to harvest, BrdU was added to each well for 6 hours for DNA incorporation. Absorbance readings were taken using a microtiter plate reader (Tecan). Data represent the average absorbance readings. Error bars represent the standard deviation amongst replicates. Cellular activation was monitored by metabolic activity and cellular proliferation. Metabolic activity was measured using the MTT assay to monitor enzyme-dependent metabolite production while proliferation was measured using 5-bromo-2'-deoxyuridine (BrdU) ELISA to monitor DNA synthesis.

In the presence of sufficient nutrients and growth factors such as PDGF, cells expressing PDGF receptors, such as VSMCs and ECs up-regulate their cellular metabolism to support growth and proliferation. VSMCs stimulated with 10 ng/mL PDGF showed increased accumulation of metabolite compared to media control and cytotoxic control (the transcription inhibitor actinomycin D at 100 ng/mL). Vehicle control (5% DMSO (v/v) in saline) did not interfere with metabolic activity. Temsirolimus, sirolimus and paclitaxel at higher concentrations had inhibitory activity in the MTT assay. Cellular proliferation in the presence of PDGF showed dose-dependent inhibition of BrdU incorporation compared to vehicle control, and concentrations of temsirolimus, sirolimus and paclitaxel were identified that approached the degree of inhibition of actinomycin D.

Example 12: Porcine Study of Temsirolimus

Overview. The purpose of the first study was to assess the pharmacokinetic profile of temsirolimus administered directly to the adventitia and perivascular tissues of femoral arteries via the Mercator MedSystems Bullfrog® Micro-Infusion Device. Specific histopathology and histomorphometry endpoints were used to determine efficacy of the temsirolimus therapy.

Design.

The study design included a total of eleven (11) animals; 8 of which received angioplasty overstretch followed by single dose of test article in bilateral superficial femoral arteries administered for a total in-life phase of 1 hour (n=2), 3 days (n=2), 7 days (n=2) and 28 days (n=2) and three additional animals that served as control by undergoing angioplasty overstretch followed by infusion of saline and surviving for 3 days (n=1), 7 days (n=1) and 28 days (n=1). A carotid artery access was utilized for all interventional procedures. In each case, all temsirolimus-treated animals underwent perivascular infusion into the femoral artery adventitia. Animals survived to 1 hour (n=2), 3 days (n=2), 7 days (n=2) and 28 days (n=2), for detailed histopathology and safety evaluation. Following survival to the designated endpoint, animals underwent blood collection, then were euthanized and necropsied followed by histological examination.

A prospective study of a single dose (357 μg in 1.5 ml) of adventitially delivered study drug (Torisel®) was conducted. All doses contained 50% contrast medium for distribution tracking. Each pig received bilateral injections in the mid femoral region. 2 pigs each were sacrificed at 1 hour, 3 days, 7 days and 28 days, for a total of 8 pigs. This was done in two phases: The first phase used to confirm the presence and concentrations of temsirolimus and sirolimus and utilized 3 animals, one each at 1 hour, 3 days and 7 days. The second phase, after confirmation of drug concentrations in the first phase, included the remaining 5 pigs (1 each at 1 hour, 3 days and 7 days and 2 at 28 days). 3 pigs were used as control in which treatment sites were subjected to overstretch injury followed by infusion of saline via the Mercator Bullfrog® catheter and sacrificed at 3 days, 7 days or 28 days (1 pig at each time point).

The injury model was angioplasty overstretch 40-60%, at least 10 atm, 3 inflations of 30 sec each and 30 sec flow. Adventitial delivery was made directly after overstretch injuries. Whole blood samples were taken following each infusion at 5 minutes, 20 minutes, 1 hour, and then 24 hours and upon sacrifice. Whole blood samples were analyzed for circulating temsirolimus and sirolimus concentrations. Arteries were perfused with Lactated Ringers Solution (LRS), extracted, and cut into serial 5 mm sections with every other section fixed in formalin (not perfusion fixed) for immunohistochemical analysis and every other section was frozen for LC/MS/MS analysis of both temsirolimus and sirolimus levels. Histopathology and histomorphometry endpoints were used to determine efficacy of the rapamycin therapy.

Results.

All animals successfully received overstretch injury to the superficial femoral arteries followed by administration of the test article or control. All animals in both the test and control groups successfully received the test or control article through the Mercator MedSystems Bullfrog® Micro-Infusion device without any complications and survived to the designated endpoint. The survival period was devoid of any test article/device or procedure related events. The concentration of temsirolimus in the mixture (comprised of 50% temsirolimus and 50% Isovue-370) was 357 µg per 1.5 mL (238 µg/mL), which represents the concentration that the treatment animals received. As all treatment animals received dosages into both femoral arteries, the total dose given to each treatment animal was 714 µg. The mean whole blood baseline temsirolimus levels were below the limits of quantitation (0.200 ng/ml for sirolimus and 0.500 ng/ml for temsirolimus) in all swine prior to dosing. Following dosing, the mean temsirolimus levels were highest at 1 hour after the first injection (32.1±11.0 ng/mL) and decreased to 2.4±1.0 ng/mL within 24 hours. Concentrations continued to decrease to almost non-detectable levels by the third day and by day 7 onwards, all blood analyzed for sirolimus and temsirolimus was found to be below the limits of quantitation.

Similar trends were observed in the sirolimus concentration in the local vascular tissue, but presence of temsirolimus was much more persistent and measured in the tissue up to 28 days post-dosing. Clinical pathology over the course of the survival duration revealed that there were no test device/drug-related effects in hematology. Changes observed in clinical chemistry were considered within expected ranges for biological and/or procedure-related variation. There was no evidence of local toxicity to the treated vessels and no evidence of local vascular irritation upon Torisel® injection with the Mercator MedSystems Micro-Infusion Device. Overall injection of Torisel® with the Mercator MedSystems Bullfrog® Micro-Infusion Device appeared safe in this model. The injection procedure produced no mural injury that could be detectable microscopically. There was no or minor structural injury ascribable to the overstretch angioplasty procedure at 0, 3 and 7 days. There was some evidence of compressive injury in the form of single cell necrosis in the media and/or media hypocellularity. There was no evidence of thrombosis or stenosis. At 28 days two treated vessels showed visible balloon overstretch injury with optimal secondary healing. Mural inflammation was absent or very minimal at all time periods and was associated with the slight mural compressive or overstretch injury noted above.

The treated vessels were fully or nearly fully healed as early as Day 7, generally showing a normal wall and occasionally displaying minimal to mild perivascular or adventitial fibrosis and low severity nonspecific and localized mural inflammation considered to be of no pathological significance. There was complete or near complete re-endothelialization and no or minimal to mild and non-stenosing neointima formation. Ki67 staining indicated cellular proliferation in the control vessel wall peaking on Day 7. Quantitative analysis of Ki67 positive nuclei showed a treatment-related decrease in average proliferation values at Day 3, Day 7 and Day 28. The decrease was substantial and consistent along the vessel length. Staining for smooth muscle actin (SMA) showed SMA positive cells in the adventitia on Day 3 that increased slightly through Day 7 and Day 28 and was primarily associated with myofibroblasts and to a lesser degree with neovascularization. This variation reflected adventitial healing response to vessel injury.

Conclusion.

Following temsirolimus administration via the Mercator MedSystems Bullfrog® Micro-Infusion Device, the mean temsirolimus sodium phosphate levels in whole blood were highest at 1 hour post-dose and decreased at 24 hours post-dose. By 3 days post dose, whole blood temsirolimus concentration had fallen to almost non-detectable levels. At 7 and 28 days post-dose, whole blood temsirolimus levels were below the limit of quantitation. At the time of necropsy on study day 28, there were persistent detectable levels of temsirolimus present in the local vascular tissues in the treated swine.

Evaluation of tissues from eleven (11) swine administered either the Torisel® treatment or the control in the adventitia of the peripheral femoral arteries with the Micro-Infusion Catheter (Mercator MedSystems) and euthanized at Day 0 (1 hour post treatment), Day 3, Day 7, and Day 28 post treatment showed no adverse or toxicologically meaningful changes in the treated vessels. There was no or minimal to mild procedural injury that was healed at the end of the study (Day 28) and produced no adverse consequences on the patency or healing of treated vessels. Cellular proliferation was increased on Day 3 in the vessel wall and adventitia and peaked on Day 7 decreasing slightly thereafter. Notably there was a moderate to marked decrease in proliferation indices in Torisel®-treated vessels throughout the vessel wall at all time periods (Day 3, 7 and 28) compared to the respective controls. This decrease was considered to be treatment-related.

The data from the current study indicate that infusion of Torisel® directly into the adventitia of femoral arteries of swine via the Mercator MedSystems Bullfrog® Micro-Infusion device does not produce evidence of local or systemic toxicity assessed by clinical observations and clinical pathology either during the survival duration or by histopathology in the analysis of tissues post mortem.

Example 13: Porcine Study of Temsirolimus

Overview.

The purpose of the second preclinical study was two-fold: (1) Confirm the safety of up to 52 mg Torisel® (temsirolimus) (10 mg per peripheral artery×4 arteries and 4 mg per coronary artery×3 arteries), and 5.2 mg Torisel® (1 mg per peripheral artery×4 arteries and 0.4 mg per coronary artery×3 arteries), as compared to saline; all agents contained 20% contrast medium and were delivered to the perivascular tissues around the coronary and peripheral arteries, and (2) Determine pharmacokinetic profile of temsirolimus and sirolimus in tissue and blood samples after Torisel® (temsirolimus) was delivered to the adventitia and perivascular tissue around femoral and coronary arteries in a porcine model of balloon overstretch artery stenosis.

Methods.

Twelve animals were evaluated for tissue safety and pharmacokinetic blood and tissue profiles. The animals received vessel injury induced via oversizing a balloon at ~20-30% overstretch, then receiving subsequent Bullfrog® catheter delivery of 4 mg/mL Torisel® or saline placebo control into the adventitia and perivascular tissue around the coronary and femoral arteries. Blood samples for pharmacokinetic analysis were taken at 5 minutes, 30 minutes, 1 hour, 24 hours, 72 hours, 7 Days, 28 Days, and termination. Animals were terminated at 90 days. Gross examination of all treated tissues and surrounding structures was performed. One coronary and one femoral artery and surrounding tissues were collected en bloc and flash frozen from each animal (note: one animal did not have a coronary vessel harvested) for pharmacokinetic analysis. Histological analysis was performed on all other collected arterial tissues.

Results.

Endpoint 1: Overall Animal Health.

All animals were generally healthy and gained weight for the duration of the study. No adverse treatment related clinical observations were noted. All physical exams were normal throughout the study duration.

Endpoint 2: Tissue Response to the Drug.

There was no mortality or significant abnormalities noted in the treated arteries at necropsy. Histologically, all arteries were patent and there were no luminal thrombi or occlusions present in any of the sections examined in the test groups. There were no histological remarkable differences in all graded parameters in the treated vessels between the test groups and the control group at either treatment location. There were thin neointimal formation, medial SMC loss, and medial fibrosis present in the treated coronary and femoral arteries in the control and test groups which most likely were caused by balloon overstretching injury in this animal model. The morphometric measured and calculated parameters were comparable between the control and test groups. The treatment did not create any clinically significant findings in the low and high test groups and therefore, did not raise a safety concern in this animal model. Taken together these findings suggest the safety of the treatments used in this animal model at the 90-day time point.

Endpoint 3: Whole Blood Temsirolimus and Sirolimus Levels.

The blood levels for all treated animals peaked at early time points, declined over time to Day 7, and were below LLOQ at 28 days and at termination. In general, observed concentrations were proportional to dose.

Endpoint 4: Homogenized Vascular Tissue Temsirolimus and Sirolimus Levels.

The tissue levels for all animals were all below LLOQ.

Conclusion.

All animals survived the treatment procedure to 90 days with no related deficiencies. There was no observed vascular toxicity of Torisel® in comparison to saline as assessed with histopathological analysis.

Example 14: Porcine Study of Temsirolimus and Dexamethasone in Combination

Overview:

The purpose of this study was to evaluate the safety and pharmokinetic profile of Torisel® and dexamethasone when delivered in an exaggerated dose to peripheral vasculature in a porcine model of balloon overstretch artery stenosis.

Methods:

Four juvenile porcine subjects were used on this study to assess tissue safety and pharmacokinetic profile. The animals received femoral artery injury induced via oversizing a balloon (~20-30% overstretch). Three animals received subsequent treatment with the Bullfrog® catheter of Torisel® (2 mg/mL) with dexamethasone (6 mg/mL) and contrast medium (20%) into the adventitia and perivascular tissue around the peripheral arteries. The fourth animal received subsequent treatment with the Bullfrog® catheter of saline and contrast medium (20%) into the adventitia and perivascular tissue around the peripheral arteries. Blood samples were taken at baseline, and post-implant 20 minutes, 1 hour, 4 hours, 24 hours, 3 days, 7 days, and just prior to termination for pharmacokinetic assessment. One animal had an early death at day 4 post-implant. The other three animals were survived for 14 days. At day 14, blood was collected, animals were euthanized and a necropsy was performed.

Results.

Endpoint 1: Overall Animal Health.

Three of four animals survived for the study duration and were generally healthy throughout. A fourth animal was found deceased. All surviving animals showed a positive weight gain over the course of the study. The deceased animal was lethargic on day 1. Lethargy continued until the animal was found deceased on day 4. On day 2, blood samples were drawn for analysis, though no conclusive results were obtained. Fever and tachycardia were noted on day 3 prior to the animal being found deceased on day 4. No antemortem diagnosis was made. No significant findings in clinical pathology were noted.

Endpoint 2: Tissue Response to the Device.

Both test and control animals exhibit none to moderate changes in the vessel wall. Perivascular and skeletal muscle changes also ranged from none to moderate in both test and control animals. Mineralization was not noted in control animal tissues examined. However, as mineralization was not previously seen with a dosage of 4 mg/mL temsirolimus, it is considered likely due to the high ethanol concentration in the solution at this dose.

Endpoint 3: Blood Temsirolimus and Dexamethasone Levels (pK Assessment).

Temsirolimus levels in the blood for all test animals peaked at early time points, declined over time to 7 days and were below the lower limit of quantitation (LLOQ) at termination. The dexamethasone levels in plasma also peaked at early time points and were below LLOQ at the 24-hour time point and after. At 14 days, dexamethasone tissue levels were all <LLOQ, and low levels of temsirolimus were found in both test animals.

Endpoint 4: Homogenized Vascular Tissue Temsirolimus and Dexamethasone Levels.

Levels of temsirolimus (50.3 and 97.5 ng/g, equivalent to 48.8 nM and 94.7 nM, respectively) were found in vascular tissue at term for the two animals treated with the test solution; no temsirolimus was found in the control animal vessels. Dexamethasone levels were <LLOQ (10.0 ng/mL homogenate, equivalent to 100 ng/g in tissue, or 255 nM) in vascular tissue at term for all animals.

Example 15: Rabbit Study of Temsirolimus and Dexamethasone in Combination

Overview.

A rabbit study was performed to evaluate the tissue effect of Torisel® (Tem) and dexamethasone (Dex) when delivered as combined or alone to peripheral vasculature in a Watanabe heritable hyperlipidemic (WHHL) rabbit model of balloon overstretch artery stenosis. Each animal was subject to balloon angioplasty and treatment in each of the two (2) external iliac arteries. Four subjects were assigned to each of three groups: Torisel®, dexamethasone, or combination.

Three subjects were assigned to each of two groups: control (vehicle delivery) or balloon only. Two New Zealand white rabbits were assigned to treatment with balloon only in one iliac and were naïve to any treatment in the other iliac.

Methods.

Twenty animals were evaluated for tissue effect of peri-vascular injection of test and control articles. Twenty-two animals underwent procedure on this study, as two animals died early and were replaced. The animals received vessel injury induced via oversizing a balloon (~20-30% overstretch). Animals were divided into the six groups with varying balloon injury targets and various combinations of test and control articles. The test and control articles were injected into the peri-vascular tissue using the Bullfrog® catheter. Animals were recovered and survived for ~28 days. At ~28 days, animals were sacrificed, a gross pathology performed and tissue harvested for histopathology analysis.

Results.

Endpoint 1: Overall Animal Health (Moribundity).

A total of 22 animals were utilized on this study. Two animals either died or were euthanized early. The reason for death or euthanasia in these animals were likely due to anesthesia and surgical intervention, but not test/control article related. While there were some instances of inappetance, no animals were noted to experience clinically significant weight loss. Many rabbits were noted as hyperglycemic and hyperlipidemic, however this is consistent with what would be expected from the genetic model of the WHHL rabbits. No other significant health issues were identified throughout the course of the study.

Endpoint 2: Tissue Response to the Device.

The combination therapy (Tem+Dex) group showed less neointimal thickness (47.40±14.84 um) and area (0.19±0.06 mm$^2$) versus temsirolimus, dexamethasone, and vehicle group. The % HHF-35 positive intimal/medial area, as a marker of vascular smooth muscle cell viability, was smaller with combination therapy or temsirolimus alone relative to dexamethasone alone or vehicle group. The number of BrdU and TUNEL positive cells including intima and media showed no statistical difference among these groups.

Twenty of 22 animals survived until 28-day term and 1 of the 20 animals was euthanized per vet orders on day 28 due to acute collapse. For the early death animals, death was related to anesthesia and surgical intervention, not test/control article. All other animals had normal in-life experiences based on the animal model and procedures performed. No vascular toxicity was noted by histopathology for any sample.

The combination therapy (Tem+Dex) group showed less neointimal thickness (47.40±14.84 μm) and area (0.19±0.06 mm$^2$) versus temsirolimus, dexamethasone, and vehicle group. The % HHF-35 positive intimal/medial area, as a marker of vascular smooth muscle cell viability, was smaller with combination therapy or temsirolimus alone relative to dexamethasone alone or vehicle group. The number of BrdU and TUNEL positive cells including intima and media showed no statistical difference among these groups. However, the balloon-only group did not exhibit significant neointima or stenosis, and therefore none of the therapies showed specific benefit over the balloon-only group. The balloon-only group also did not exhibit similar proliferative markers to any of the other groups, suggesting a lack of proliferative injury induction or a different stage of disease in that group of rabbits.

Conclusion.

The delivery of Torisel® and dexamethasone to a peripheral vasculature in a Watanabe heritable hyperlipidemic (WHHL) rabbit model of balloon overstretch artery stenosis was found to be safe and effective. Animals survived the study duration of ~28 days without significant deficiencies related to the test article. Histopathology evaluation of the various groups showed less neointimal thickness and area in animals treated with Torisel and dexamethasone when compared to the Torisel only, dexamethasone only, and vehicle groups.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. An injectable composition comprising a therapeutically effective amount of temsirolimus or a pharmaceutically acceptable salt thereof, a therapeutically effective amount of dexamethasone or a pharmaceutically acceptable salt thereof, and a pharmaceutically acceptable excipient, wherein the composition is suitable for perivascular injection adjacent a blood vessel with minimal to no local toxicity to the blood vessel.

2. The injectable composition of claim 1, wherein the therapeutically effective amount of temsirolimus is about 1 μg to 50 mg.

3. The injectable composition of claim 1, wherein the therapeutically effective amount of dexamethasone is about 0.8 mg to 8 mg per cm of longitudinal length of a disease site in a blood vessel.

4. The injectable composition claim 1, wherein the therapeutically effective amount of dexamethasone is about 0.05 mg to 10 mg per cm of longitudinal length of a disease site in a blood vessel and the therapeutically effective amount of temsirolimus is about 0.005 mg to 5 mg per cm of longitudinal length of the disease site in the blood vessel.

5. The injectable composition of claim 1, wherein the injection volume of the composition is about 0.01 mL to about 50 mL.

6. The injectable composition of claim 1 wherein the pharmaceutically acceptable excipient comprises 0.9% sodium chloride injection USP, dehydrated alcohol, dl-alpha tocopherol, anhydrous citric acid, polysorbate 80, polyethylene glycol 400, propylene glycol, or a combination thereof.

7. The injectable composition of claim 1, wherein the composition is suitable for delivery.

8. The injectable composition of claim 1, wherein the composition is suitable for delivery below the knee.

9. The injectable composition of claim 1, wherein the composition is suitable for delivery above the knee.

10. The injectable composition of claim 1, wherein the composition is suitable for adventitial delivery to a below-knee popliteal or tibial vessel.

11. The injectable composition of claim 1, wherein the composition is suitable for delivery to a femoral vessel.

12. The injectable composition of claim 1, wherein the composition is suitable for adventitial delivery to a coronary vessel.

13. The injectable composition of claim 1, wherein the composition is suitable for delivery to a coronary artery.

14. The injectable composition of claim 1, wherein the therapeutically effective amount is determined by a longitudinal length of a target diseased artery.

15. The injectable composition of claim 1, wherein the therapeutically effective amount of dexamethasone is about 0.1 mg to 2 mg per cm of longitudinal length of a disease site in a blood vessel and the therapeutically effective amount of temsirolimus is about 0.025 mg to 1 mg per cm of longitudinal length of the disease site in the blood vessel.

16. The injectable composition of claim 1 for use in treating restenosis.

17. The injectable composition of claim 16 for use in treating restenosis below the knee.

18. The injectable composition of claim 16 for use in treating restenosis above the knee.

19. The injectable composition of claim 16 for use in treating restenosis in a below-knee popliteal vessel or tibial vessel.

20. The injectable composition of claim 1, wherein the composition further comprises a contrast medium for visualizing the injection.

21. The injectable composition of claim 1, wherein the composition results in no adverse or toxicologically meaningful change to the blood vessel at least 1 hour after the perivascular injection.

22. The injectable composition of claim 1, wherein the composition results in no adverse or toxicologically meaningful change to the blood vessel at least 3 days after the perivascular injection.

23. The injectable composition of claim 1, wherein the composition results in no adverse or toxicologically meaningful change to the blood vessel at least 7 days after the perivascular injection.

24. The injectable composition of claim 1, wherein the composition results in no adverse or toxicologically meaningful change to the blood vessel at least 28 days after the perivascular injection.

25. The injectable composition of claim 1, wherein the therapeutically effective amounts of temsirolimus and dexamethasone or the pharmaceutically acceptable salts thereof are at concentrations insufficient to lead to local toxicity to the blood vessel after the perivascular injection.

26. The injectable composition of claim 16, wherein the composition reduces neointimal thickness and area after the perivascular injection as compared to a perivascular injection of (i) a composition of temsirolimus or a pharmaceutically acceptable salt thereof alone or (ii) a composition of dexamethasone or a pharmaceutically acceptable salt thereof alone.

* * * * *